(12) United States Patent
Walker et al.

(10) Patent No.: US 8,148,559 B1
(45) Date of Patent: Apr. 3, 2012

(54) SUPERCRITICAL FLUID EXPLOSION PROCESS TO AID FRACTIONATION OF LIPIDS FROM BIOMASS

(75) Inventors: Terry H. Walker, Townville, SC (US); Meidui Dong, Newark, DE (US); Keri B. Cantrell, Florence, SC (US); Mark C. Thies, Clemson, SC (US)

(73) Assignee: Clemson University Research Foundation, Clemson, SC (US)

( * ) Notice: Subject to any disclaimer, the term of this patent is extended or adjusted under 35 U.S.C. 154(b) by 770 days.

(21) Appl. No.: 12/200,212

(22) Filed: Aug. 28, 2008

Related U.S. Application Data

(60) Provisional application No. 60/969,276, filed on Aug. 31, 2007.

(51) Int. Cl.
*C07F 9/02* (2006.01)
(52) U.S. Cl. ....... 554/82; 424/1.65; 424/1.77; 424/1.85; 554/80; 554/84; 558/166; 558/169
(58) Field of Classification Search ............... 554/80, 554/82, 84; 558/166, 169; 424/1.65, 1.77, 424/1.85
See application file for complete search history.

(56) References Cited

U.S. PATENT DOCUMENTS

| | | |
|---|---|---|
| 4,695,411 A | 9/1987 | Stern et al. |
| 5,130,242 A | 7/1992 | Barclay |
| 5,306,637 A | 4/1994 | Lin et al. |
| 5,338,471 A | 8/1994 | Lal |
| 5,380,826 A | 1/1995 | Castor et al. |
| 5,550,156 A | 8/1996 | Kyle |
| 5,591,343 A | 1/1997 | Kitaoka et al. |
| 5,620,730 A | 4/1997 | van Noort |
| 5,730,029 A | 3/1998 | Stoldt et al. |
| 5,854,064 A | 12/1998 | Castor et al. |

(Continued)

FOREIGN PATENT DOCUMENTS

WO    WO 2006/047445 A2    5/2006

OTHER PUBLICATIONS

Gaspar et al., "Disruption of glandular trichomes with compressed $CO_2$: alternative matrix pre-treatment for $CO_2$ extraction of essential oils", Journal of Supercritical Fluids 21 (2001) 11-22.

*Primary Examiner* — Deborah D Carr
(74) *Attorney, Agent, or Firm* — Dority & Manning, P.A.

(57) ABSTRACT

Disclosed are processes for development and recovery of lipids from biomass. A plant or microorganism-based biomass can be developed to encourage a desired lipid profile. Following development, ecologically friendly normally gaseous fluids such as carbon dioxide can be pressurized to a supercritical state followed by rapid expansion. The fluid is first contacted with a biomass source including oil-containing microorganisms and/or agricultural products. For instance, fungi or algae can be bioconverted from another biomass sources such as canola seed or corn syrup and then contacted with the high pressure fluid. During a contact period, the fluid can diffuse into the biomass, and in particular through the cell walls of the biomass. The fluid undergoes rapid release of pressure and opens the cell structure for improved release of oil. The fluid can optionally be utilized for extraction following the explosion process. For instance, the fluid can be re-pressurized in the same vessel for extraction processes.

37 Claims, 24 Drawing Sheets

U.S. PATENT DOCUMENTS

| | | | |
|---|---|---|---|
| 6,015,440 | A | 1/2000 | Noureddini |
| 6,166,231 | A * | 12/2000 | Hoeksema ............ 554/12 |
| 6,174,501 | B1 | 1/2001 | Noureddini |
| 6,479,277 | B2 | 11/2002 | Duncan |
| 6,538,146 | B2 | 3/2003 | Turck |
| 6,569,640 | B1 * | 5/2003 | Castor et al. ............ 435/41 |
| 6,884,900 | B2 | 4/2005 | Maeda et al. |
| 6,960,672 | B2 | 11/2005 | Nakayama et al. |
| 7,001,610 | B2 | 2/2006 | Stewart |
| 7,029,707 | B2 | 4/2006 | Gow et al. |
| 2004/0074760 | A1 | 4/2004 | Portnoff et al. |
| 2007/0248739 | A1 | 10/2007 | Abril et al. |
| 2008/0096964 | A1 | 4/2008 | Subramanian et al. |
| 2008/0107791 | A1 | 5/2008 | Fichtali et al. |

* cited by examiner

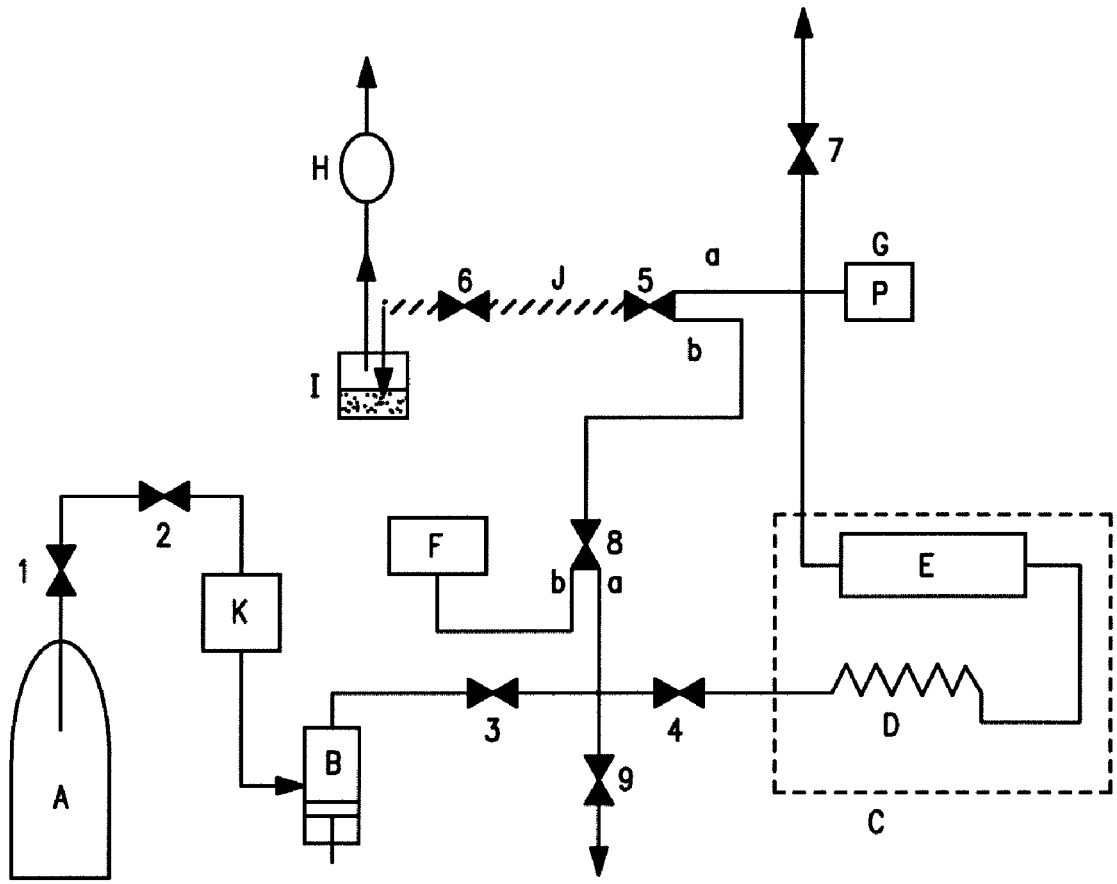

| INSTRUMENTATION | | VALVES | |
|---|---|---|---|
| A | CO2 Cylinder | 1 | CO2 Cylinder Supply (from A) |
| B | CO2 Syringe Pump | 2 | CO2 Pump Supply |
| C | Water Bath | 3 | CO2 Syringe Pump Isolation |
| D | Preheating Coil for CO2 | 4 | Vessel Isolation |
| E | Explosion/Extraction Vessel | 5a | CO2 Flow Control |
| F | Hexane Reservoir | 5b | Hexane Rinse Control |
| G | Vessel Pressure Transducer | 6 | CO2 Micrometering |
| H | Gas Flow Meter | 7 | Explosion High Pressure Release |
| I | Hexane Cold Trap | 8a | CO2 By-Pass |
| J | Flow Control Section Heating Tape | 8b | Hexane Reservoir Outlet |
| K | CO2 Feed Ice Bath | 9 | CO2 Pressure Release |

FIG. 4

\* = not significantly different from control ($\alpha = 0.05$)

* = significantly different from the control at the 95% level;  # = significantly different from (10.3 MPa, 20 min) at the 95% level

SUPERCRITICAL FLUID EXPLOSION PROCESS TO AID FRACTIONATION OF LIPIDS FROM BIOMASS

CROSS REFERENCE TO RELATED APPLICATION

The present application claims filing benefit of U.S. Provisional Patent Application Ser. No. 60/969,276 having a filing date of Aug. 31, 2007, which is incorporated herein in its entirety.

BACKGROUND

Natural plant and microorganism-based oils possess excellent potential for health benefits through ingestion. For example, beneficial health effects of consuming polyunsaturated fatty acids (PUFAs), which include eicosapentaenoic acid (C20:5, $\omega$3) (EPA), docosahexaenoic acid (C22:6, $\omega$3) (DHA), and arachidonic acid (C20:4 $\omega$-6) (ARA), have been well documented for many years. These fatty acids have been linked to visual and mental health as well as regulation of critical biological functions. PUFAs are associated with the prevention and treatment of coronary heart disease and abnormal cholesterol levels, in addition to alleviating inflammatory conditions and even retarding growth of tumor cells. PUFAs are also precursors to a variety of metabolites, including prostaglandins and leukotrienes that regulate critical biological functions.

High ratios of $\omega$-6 to $\omega$-3 PUFAs typical of the Western diet (e.g., 15:1-17:1) have been linked to common maladies like heart disease, cancer and other metabolic disorders. Lowering this ratio is considered to be essential for lowering the risk of many chronic diseases. Accordingly, it is generally held that the $\omega$-6: $\omega$-3 ratio should be taken into consideration when producing a supplement. For instance, U.S. Pat. No. 5,550,156 to Kyle discloses a 2:1 blending of ARA and DHA for supplementing infant formula for the purpose of increasing the PUFA amounts and ratios to simulate the natural blend found in human breast milk.

Fish oil supplements dominate the current PUFA-rich oil market. Unfortunately, however, fish oil can possess objectionable tastes and odors and may contain cholesterol as well as pollutants such as mercury. Microorganisms as well as agricultural sources are promising producers of PUFA-rich oils that can serve as an alternative to fish oils. For instance, microorganisms including algal and fungal sources are capable of year-round oil production on a variety of cheap substrates. For example, the fungi *Pythium irregulare* is capable of high production of intracellular oil containing the PUFAs EPA and ARA as well as other long chain fatty acids such as linoleic acid (C18:2, $\omega$-6). Submerged culture studies investigating oil production over a broad temperature range (14° C., 21° C., and 28° C.) have found maximum oil production, 0.893 mg/ml, occurring at 21° C. and 4 days of fermentation. Commercially feasible technology to produce EPA and DHA from microalgae and fungi is being investigated on many fronts.

Plant and microorganism-based oils are also becoming attractive as replacements for non-renewable petroleum. For instance, algae are the highest yield feedstock found to date for production of oils as may be utilized in formation of biodiesel, lubricants, and the like. Biodiesel, a biodegradable, non-toxic fuel formed from transesterification of any of a variety of vegetable oils or animal fats, has long been considered a viable option to petroleum-based diesel (petrodiesel). Biodiesel can be utilized as formed in unmodified diesel engine vehicles and furnaces, can be easily blended with petrodiesel, and typically produces about 60% less net carbon dioxide emissions than petrodiesel. It is estimated that between 250 and 300 billion gallons of diesel oil is used annually in the United States for transportation fuels and home heating oil. Of this amount, only about 8% comes from renewable resources. Moreover, while relatively few automobiles in the U.S. utilize diesel fuel, the opposite trend exists in Europe, with total diesel consumption in the U.S. from trucks, buses and other transportation estimated to be about 80% of Europe's consumption level.

Between 1978 and 1996, the U.S. National Renewable Energy Laboratory (NREL) examined the possibility of using algae as a biodiesel source. These studies resulted in a collection of approximately 300 different species of algae, both fresh-water and salt-water, and made them available to researchers from around the world. This initial work on algal biodiesel development was curtailed in the mid-90's, due primarily to a drop in crude oil prices and government budget cuts. Interest in biodiesel from algal oils has revived due to both increasing crude oil prices and increasing interest in energy independence from fossil fuels.

Unfortunately, problems exist with conventional methods utilized for oil recovery from biomass. These conventional methods include organic solvent extraction, vacuum distillation, and maceration, all of which can present ecological problems both during production and with regard to waste disposal. Other problems concern product recovery, as natural oils such as PUFAs are susceptible to thermal and oxidative degradation under the harsh conditions these techniques employ. In addition, oils for human consumption should be obtained using methods that employ solvents that are acceptable in terms of toxicity, handling, safety and cost.

What is needed in the art are improved methods for obtaining high value lipids from biomass.

SUMMARY

According to one embodiment, disclosed herein is a method for recovering lipids from a biomass. A biomass can be a plant-based or a microorganism-based biomass. For example, a microorganism-based biomass can be a fungal or an algal biomass. A method can include developing a biomass on an oleaginous substrate that can provide one or both of carbon and nitrogen to the biomass. Upon development of the biomass, the biomass can bioconvert lipids of the substrate. Through the bioconversion process, the biomass can exhibit an alteration in the lipid profile of the biomass.

Following development of the biomass, lipids can be extracted from the biomass. For instance, lipids can be extracted according to a supercritical fluid extraction process, and in one embodiment, a carbon dioxide supercritical fluid extraction process.

Methods as disclosed herein can also include disrupting the cellular structure of one or both of the substrate and the biomass developed on the substrate. For example, a carbon dioxide explosion process can be utilized to disrupt the cellular structure of the substrate upon which the biomass can be developed and/or the developed biomass prior to the lipid extraction process.

Lipids obtained from disclosed processes can exhibit a desired lipid profile. For instance, an extracted lipid product can describe a lipid profile that is high in polyunsaturated fatty acids, or alternatively an extracted product can describe a lipid profile that is low in PUFAs and high in long chain mono and/or unsaturated fatty acids.

In one preferred embodiment, both a biomass cellular disruption process and a lipid extraction process can be carried out in a single reaction vessel and can utilize recyclable carbon dioxide a solvent, providing cost benefits to disclosed methods.

BRIEF DESCRIPTION OF THE FIGURES

The presently disclosed subject matter may be better understood with reference to the following figures, in which:

FIG. 4 is a schematic representation of a supercritical carbon dioxide extraction process as described herein;

DETAILED DESCRIPTION

Figure 1A:
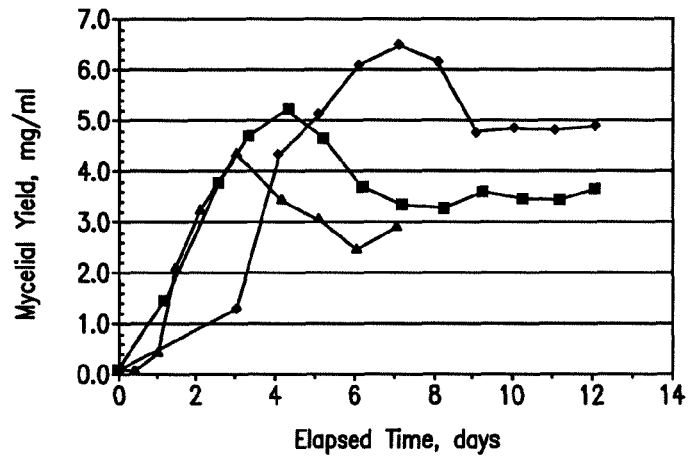
FIG. 1 illustrates the effect of temperature on growth of *P. irregulare* in submerged culture including mycelial yield, mg/mL (FIG. 1A), lipid production, mg/mL (FIG. 1B), and glucose utilization mg/mL (FIG. 1C)

Reference will now be made in detail to various embodiments of the disclosed subject matter, one or more examples of which are set forth below. Each embodiment is provided by way of explanation of the subject matter, not limitation thereof. In fact, it will be apparent to those skilled in the art that various modifications and variations may be made to the disclosed subject matter without departing from the scope or spirit of the disclosure. For instance, features illustrated or described as part of one embodiment, may be used with another embodiment to yield a still further embodiment.

Disclosed herein are methods and systems as may be used to recover lipids from a biomass. For instance, disclosed methods can be utilized to recover lipids from plant-based or microorganism-based biomass. Moreover, disclosed methods can be utilized to develop a desirable lipid profile in a biomass prior to recovery of the lipids. For example, a biomass can be developed so as to provide a high PUFA profile as may be utilized in producing nutraceutical products. In another embodiment, a biomass can be developed so as to provide a lipid profile that is lower in PUFAs and higher in medium and long-chain monounsaturated fatty acids as may be utilized in producing industrial materials such as biodiesel, lubricants, and the like. In general, medium-chain fatty acids are those having a chain length of between about 6 and about 12 carbons, while long chain fatty acids are those having longer chain length. For example, a long chain fatty acid can have a chain length of between about 14 and about 18 carbons, and a very long chain fatty acid can have a chain length greater than that, for instance greater than about 20 carbons.

Lipid recovery processes disclosed herein can obtain desirable lipids from a biomass in extremely high yields and with improved recovery rates. In one embodiment, a recovery process can include a cellular disruption step in conjunction with one or more solvent extraction steps that can thereby improve lipid yield as compared to previously known lipid recovery processes.

Disclosed methods can be environmentally friendly. For example, disclosed methods can utilize green extraction solvents such as super critical carbon dioxide or water, rather than organic solvents such as hexane and benzene, as are commonly utilized in other lipid extraction methodologies. Environmentally friendly materials such as carbon dioxide can also be utilized in disclosed cellular disruption processes. Accordingly, in one preferred embodiment, a lipid recovery process can take place in a single reactor system and can utilize a minimum number of reagents that can beneficially be recycled for use in both a cellular disruption step and one or more extraction steps many times over.

A suitable biomass can be either plant-based or microorganism-based. In general, a biomass for use as disclosed herein can be a naturally occurring high oil content biomass. The term high oil content biomass as utilized herein generally refers to a plant or microorganism biomass including in its natural state at least about 15 wt. % lipid, for instance between about 15 wt. % and about 40 wt. % lipid, or even higher, in other embodiments.

In general, a preferred starting biomass can be determined based upon the desired lipid profile of the product. For instance, when developing a product biomass to include a relatively low PUFA content, such as may be utilized in forming a biodiesel, the starting biomass of choice can include rapeseed, soybean, corn, sesame, and the like. In an alternative embodiment, for instance when a high PUFA lipid profile is desired in the product, a plant-based starting biomass can include plants that naturally provide PUFAs such as canola, safflower, linseed, and the like.

Microorganism-based biomass encompassed by the present disclosure can generally include fungal and algal biomass. Similar to plant-based biomass, a starting microorganism-based biomass can generally be selected based upon the natural lipid profile of the microorganisms. Preferred microorganism-based biomass can also be highly oleaginous naturally, before any further development of the biomass, so as to better provide a high yield process.

There are thousands of known species of oleaginous microorganisms including both algae and fungi, and possibly as many or more as yet unrecognized species, any of which may be utilized alone or in combination with other species as a biomass as disclosed herein. For instance, both fresh-water and salt-water algae is encompassed within the present disclosure. In one embodiment, the particular species utilized can be selected based upon the environmental conditions of the process. For example, the biomass species or combination of species can be selected based upon the process conditions including season, light characteristics, temperature variations, water conditions (e.g., potable or non-potable water source, pH, salinity, nutrient availability, and the like) as well as based upon the natural oil content of the biomass.

In one embodiment, diatoms (genera *Amphora*, *Cymbella*, *Nitzschia*, and so on), also referred to as *Bacillariophytes*, may be utilized. Species of diatomes naturally exist in both salt water and fresh water and many species of diatoms are extremely rich in oil. Other algal species can include, without limitation, fresh water *Chlorella* sp., *Schizochytrium* spp., *Phaeodactylum* spp. *Cryptecodinium cohnii*, and the like.

Similarly, a wide variety of fungi can be utilized in disclosed processes. For example, filamentous fungi of the *Pythium* species such as *P. irregulare* that can produce health beneficial, valuable PUFA rich oils such as EPA can be utilized in one embodiment. Other fungal species encompassed herein can include, without limitation, those of the species *Mortierella*, such as *M. alpina*, and *M. elongate*, those of the species *Saprolegnia* spp., and the like. Production of the fungus *Mortierella* has been studied previously using glucose as a carbon source and yeast extract as a nitrogen source. ARA and EPA are currently produced by industrial cultivations of *M. alpina* throughout the world.

According to one embodiment, a biomass can be developed so as to improve the specific lipid profile desired. For example, biomass growth parameters can be optimized to develop a desired lipid profile. For instance, growth temperature, pH, and nutrient source can be controlled to improved the desired lipid profile. More specifically, microorganisms and plants for use in the disclosed process can be cultured so as to facilitate concentration of the desired oils in the biomass.

For example, the PUFA content of fungal intracellular oil is variable and can be affected by fermentation temperature. Similarly, algal lipid profile can be affected by feedstock as well as other growth conditions. For instance, depending upon culture conditions, EPA content can range in a submerged fungal biomass culture from about 3.5 to about 10.9 wt % of the total oil extracted, with a lower fermentation temperature (14° C.) promoting greater EPA production. For example, maximum lipid yield of a submerged *P. irregulare* culture, e.g., about 0.893 mg/ml, can be achieved after 4 days of growth at 21° C. Accordingly, when considering a similar fungal culture, culture temperatures between about 10° C. and about 25° C. can be maintained to culture large amounts of biomass with lipids accounting for between about 15% and about 20% of the total biomass weight. Other specific biomass cultures can be similarly optimized through standard processes as are generally known in the art to maximize desired lipid recovery and as described further in the example section, below.

Feedstock substrate for a microorganism-based biomass can be selected and/or processed so as to improve lipid yield in the biomass. More specifically, a microorganism can be developed on a particular substrate so as to develop a desired lipid profile in the biomass. For instance, a high oil content plant-based feedstock substrate as described above can be utilized as both a carbon and nitrogen source for the fermentation of a fungal biomass. Bioconversion of the digested plant oils to fungal oil can increase the level of the desirable plant lipids in the microorganism biomass. Accordingly, a specific feedstock can be selected based upon the lipid profile of the plants utilized to form the feedstock.

In one exemplary embodiment, a microorganism-based biomass can be fermented on a high PUFA content plant feedstock, such as canola. Upon fermentation (one specific example of which is discussed at length below in the example section), the oil profile of the biomass can be enhanced with the addition of desirable lipids, and in one particular embodiment, desirable PUFAs. Moreover, the lipid profile of the developed microorganism biomass can show improvement over that of both the starting feedstock and the starting biomass. For instance, as well as the addition of desirable lipids to the biomass lipid profile, the lipid profile of the developed biomass can also be superior to that of the plant feedstock. For instance, the lipid profile of the developed biomass can exhibit an improved polyunsaturated to saturated fatty acid ratio as compared to either the starting feedstock or the starting biomass.

Selection of feedstock for a microorganism-based biomass can provide additional beneficial characteristics to a process. For instance, carbon sources for a developing microorganism-based feedstock can include glycerol, plant-based oils, glucose, and the like. Glycerol can be preferred in one particular embodiment as glycerol is a byproduct of biodiesel formation processes. Thus, in the particular case of utilizing disclosed lipid recovery processes in the formation of biodiesel, a byproduct of the process can be recycled and utilized within the process, further reducing associated costs of a biodiesel formation process.

Similarly, nitrogen sources for development of a microorganism-based biomass can be selected to further enhance a process. For instance, a nitrogen source can include an ecologically friendly nitrogen source or nitrogen obtained from waste streams, so as limit environmental impact of disclosed methods.

In one embodiment, a feedstock can be preprocessed to improve disclosed methods and products. For instance, a feedstock for a microorganism-based biomass can be subjected to a cellular disruption process, for instance a high pressure carbon dioxide explosion process, that can improve uptake and bioconversion of the plant lipids by the microorganism.

In general, a cellular explosion treatment can rupture cell walls through the rapid change of a solvent, e.g., $CO_2$, from a high pressure, generally supercritical, to a lower pressure, e.g., atmospheric, gaseous state. While not wishing to be bound by any particular theory, it is believed that cellular disruption of a plant feedstock, e.g., a flaked feedstock, can enhance uptake and improve digestibility of plant oils by a microorganism. For instance, subjecting a canola meal feedstock to a $CO_2$ explosion process prior to fermenting a fungal biomass on the feedstock can improve yields of both ARA and EPA PUFAs in the developed biomass.

According to one embodiment, a $CO_2$ explosion process can be carried out by soaking a plant-based feedstock with high pressure $CO_2$ for a given time, for instance between about 10 minutes and about one hour, or about 30 minutes, in one embodiment. This contact time can allow the $CO_2$ molecules to penetrate the cellular structure. Following a soaking time, the pressure can be suddenly released, causing the $CO_2$ to flash violently and break apart the cells. If desired, the $CO_2$ can be captured and re-pressurized for recycle.

Following development of a biomass, for instance on an exploded feedstock, lipids can be recovered from the biomass according to a process that combines a cellular disruption step with one or more lipid extractions. In one embodiment, disclosed methods can utilize nonpolar solvents in both the cellular disruption step as well as the extraction step. In one preferred embodiment, both processes can utilize as solvent a single ecologically favorable compound, such as carbon dioxide or water, for example.

An extraction process that utilizes an ecologically favorably solvent can be preferred as such a solvent, e.g., $CO_2$, can be a non-toxic, non-flammable, inexpensive, and a "green"  solvent. Through utilization of such materials, a lipid recovery process can be carried out that can provide both environmental and cost benefits. For instance, as the same solvent can be utilized in both disruption and extraction steps, the single solvent can be recycled throughout the recovery process. In addition, in one embodiment, a lipid recovery process can utilize a single reaction vessel for explosion, extrusion, extraction, fractionation, and solvent removal in either batch or continuous mode. As such, disclosed methods can be utilized to significantly reduce costs and provide better extraction efficiency as compared to previously known methods.

In one preferred embodiment, one or more supercritical fluid extraction (SFE) processes can be carried out to recover lipids from a biomass. SFE with $CO_2$ is already established as a process for the decaffeination of coffee beans and tea. SFE can be beneficial in disclosed processes, particular in those embodiments in which PUFAs are targeted for recovery, as SFE can limit auto-oxidation, decomposition, and polymerization of PUFAs found in animal, fish, and fungal oils due to its low temperature requirements. Moreover, SFE with $CO_2$ as solvent can also enable complete removal of the non-toxic, inexpensive, inert solvent. Additionally, use of a nontoxic solvent such as $CO_2$ in an extraction process can provide for recovery of desired components from natural materials for eventual use in food, cosmetics, pharmaceutical, and nutraceutical industries.

SFE utilizes the ability of normally gaseous chemicals to become solvents for certain solutes under a combination of tunable properties in terms of temperature and pressure. The solvent becomes supercritical when it is raised above its critical point for both temperature and pressure ($T_c$ and $P_c$, respectively). For $CO_2$, $T_c$ is 31.1° C. and $P_c$ is 7.38 MPa. Only one phase exists in the critical region that possesses both gas and liquid-like properties. A supercritical fluid has liquid-like densities and a viscosity close to that of normal gases. The diffusivity for a supercritical fluid is about two orders of magnitude higher than typical liquids: (e.g., about 0.2 to about $0.7) \times 10^{-3}$ cm$^2$/s compared to (about 0.2 to about $2.0) \times 10^{-5}$ cm$^2$/s. The low viscosity and other "gas-like" properties allow for the solvent to diffuse more readily through the solid matrix. These characteristics facilitate rapid mass transfer and faster completion of extractions over traditional liquid extraction techniques.

An SFE process is based on contact between a solid raw material and the pressurized solvent, which removes the compounds of interest from the solid phase via internal and external mass transfer mechanisms. The first part of extraction, the constant extraction rate (CER) period, is governed by the solubility equilibrium between the solvent and extract. This constant extraction rate (CER) period can be linear with the partition coefficient usually being a part of the constant of proportionality. A process can include one or more CER periods, for example when plant cell walls form an additional barrier to molecular diffusion. Once the easily accessible, surface extracts are depleted, diffusion-controlled mass transfer occurs and a falling extraction rate (FER) period is seen. Eventually, diffusion of the extracts through the bulk material becomes a more integral part of the extraction process and product accumulation with time approaches zero. Once diffusion completely controls the mass-transfer process, the extraction is said to be in a diffusion-controlled (DC) regime. Different mathematical aspects related to SFE have resulted in multiple variables and complex equations derived to model the SFE process. Many models have been proposed; yet, no single model has been universally accepted.

Carbon dioxide ($CO_2$) is preferred as an extraction solvent in one embodiment of the disclosed processes as it can prevent harmful oxidation reactions and can enter a supercritical state at low temperature but relatively high pressure conditions. Supercritical $CO_2$ has additional advantages of low cost, non-toxicity, high diffusivities, and low viscosity. In addition, solvent separation from the extract is easily accomplished by reducing the pressure and returning the $CO_2$ to a gaseous state. However, the present disclosure is not limited to supercritical carbon dioxide as solvent, and other compounds are encompassed herein. For example, supercritical water can be utilized as an extraction solvent in one embodiment.

Disclosed methods can also incorporate a co-solvent according to known methods. In general, a co-solvent employed in the disclosed process can be compatible with the supercritical fluid selected and also be capable of at least partially dissolving lipids being extracted from a biomass. Suitable co-solvents for use in conjunction with a supercritical fluid can include ecologically friendly materials such water; C-1 to C-10 alcohols such as methanol, ethanol, propanol, butanol and isopropanol; or mixtures of any of the above. When included, a co-solvent can be employed in amounts effective to aid in the wetting and/or hydrolysis of the biomass, and can range from zero to about 50% by weight of the total mass of the composition.

According to disclosed subject matter, one or more extraction processes can be combined with a cellular disruption process. For instance, a $CO_2$ explosion process as described above with regard to a feed stock for a biomass can similarly be carried out on a developed biomass.

Integration of $CO_2$-explosion and SFE technologies for treatment of a lipid-containing biomass can lead to higher extraction yields of oils, such as high-value nutraceutical oils. The explosion process can expose the intracellular oil for faster extractions with a longer CER period, thus avoiding diffusion-controlled extraction. While not wishing to be bound by any particular theory, it is believed that cellular disruption can enhance the overall oil extraction by exposing more surface oil to the extraction solvent. Additionally, an explosion step can operate at the same low-temperature, high-pressure conditions as SFE and can use the same nontoxic solvent making it a more attractive than previously known solvents such as steam and ammonia.

A biomass can be pretreated prior to a cellular disruption process. For example, $CO_2$-explosion can be applied to freeze-dried biomass, which can further enhance post-explosion SFE extraction of total oil.

As discussed above, an explosion process can begin with a period of time during which a biomass can be held in contact with the high pressure solvent. A pre-explosion soaking time can be varied (for example between about 20 and about 60 minutes) along with the soaking pressure (e.g., between about 27.6 and about 10.3 MPa). Disclosed methods are not limited to any particular soaking time, however, or even to a single soak period. For instance, in one embodiment, longer and/or multiple soaking times can promote a longer CER period during extraction. In one embodiment, an explosion step can be carried out at constant temperature, for example about 40° C., though this is not a requirement of disclosed subject matter.

A large increase in lipid recovery from a biomass can be obtained with an SFE step following a $CO_2$ explosion process. For example, about a 25 wt. % increase in g oil/g total oil recovered can be obtained through addition of a pre-extraction explosion process. With respect to specific lipids, e.g., targeted PUFAs, an explosion pretreatment can increase desirable PUFAs such as EPA and ARA concentrations in the extracted oil nearly doubling their weights in one embodiment, and suggesting multiple promising applications.

As previously mentioned, disclosed recovery methods can include multiple extraction steps. For instance, in one embodiment, a first extraction process can be carried out prior to an explosion process, and this can be followed by a second post-explosion extraction process to further enhance efficiency of oil removal. According to this embodiment, extraction can begin at high pressure, prior to reduction in pressure to the point of cellular disruption. While not wishing to be bound by any particular theory, it is believed that a pre-explosion extraction process can improve access of a $CO_2$ solvent to the cell walls and hence improve penetration of the cellular structure by the solvent. Moreover, multiple pre-explosion high pressure extraction processes can be carried out to initiate extraction as well as to perturb the system into a more convective diffusion regime.

Recovered oils can be processed and utilized according to any known process and system and for any of a variety of applications. For instance, recovered lipids can be separated, for instance in an oil fractionation process as is generally known in the art, to provide a first oil stream comprised primarily of medium and long chain monounsaturated fatty acids as may be utilized in production of a first product, e.g., biodiesel, and a second oil stream having a high PUFA content that may provide a second product, e.g., high value oils as may be utilized in formation of nutraceutical products, cosmetics, animal or human food supplements, and so forth.

One oil stream obtained at extraction of the biomass product can be utilized to form biodiesel according to a transesterification process. In general, a transesterification process can include a catalyzed reaction between the triglycerides of the feed oil and an alcohol (e.g., methanol) to form lower alkyl esters (i.e., biodiesel) and glycerol. For example, the Connemann process (U.S. Pat. No. 5,354,878, incorporated herein by reference), which is well known to those of ordinary skill in the art, can be utilized to form biodiesel and glycerol from the separated oils. As previously mentioned, according to one embodiment, a glycerol byproduct can then be utilized as a feedstock for a microorganism-based biomass.

In general, the Connemann process utilizes continuous flow of the reaction mixture (triglyceride-containing oil, alcohol, and alkaline catalyst) through reactor columns, in which the flow rate is lower than the sinking rate of glycerol. This results in the continuous separation of glycerol from the biodiesel. The reaction mixture may be processed through further reactor columns to complete the transesterification process. Residual methanol, glycerol, free fatty acids and catalyst may be removed by aqueous extraction.

Biodiesel production from lipid obtained as disclosed herein is not limited to formation via the Connemann process, however. For instance batch reaction methods (e.g., J. Am. Oil Soc. 61:343, 1984) may be preferred in other embodiments. Any method known in the art for producing biodiesel from triglyceride-containing oils may be utilized; for example methods as disclosed in U.S. Pat. Nos. 4,695,411 to Stern, et al.; 5,338,471 to Lal; 5,730,029 to Stoldt, et al.; 6,015,440 to Noureddini; 6,174,501 to Noureddini; 6,538,146 to Turck; 6,884,900 to Maeda, et al.; 6,960,672 to Nakayama, et al., and U.S. Patent Application Publication 2004/0074760 to Portnoff, et al., each of which are incorporated herein by reference. Alternative methods for formation of biodiesel from triglycerides that do not involve transesterification may also be used. For example, by pyrolysis, gasification, or thermochemical liquefaction methods can be used (see, e.g., Dote, 1994, Fuel 73:12; Ginzburg, 1993, Renewable Energy 3:249-52; Benemann and Oswald, 1996, DOE/PC/93204-T5).

The crude biodiesel can be further processed as desired, for instance to provide a biodiesel product having characteristics particular to a specific application. For instance, U.S. Patent Application Publication 2006/0074256 to Alasti, incorporated herein by reference, describes a process including separating salts, alcohols, and glycerol from a feed stream including all of the above in combination with mono-alkyl ester biodiesel to provide a high-grade biodiesel product. U.S. Pat. No. 6,827,841 to Kiser, et al., incorporated herein by reference, describes a low viscosity, high coking value petroleum tar material that contains at least one biodiesel dissolved therein.

Applications for recovered lipids obtained as described herein are not limited to formation of biodiesel. For instance, recovered oils high in PUFAs can be utilized as a food additive or supplement, for instance in infant formulas, parenteral nutrition, in the form of capsules as a nutrition supplement, and the like.

Other uses for recovered lipids can include use as an active ingredient in cosmetic products, as emulsifiers in the food or cosmetics industries, or as lubricants.

The presently disclosed subject matter may be better understood with reference to the Examples, below.

Example 1

The effect of temperature on fungal biomass yield and lipid production was studied. *Pythium irregulare* (ATCC 10951) was maintained on corn meal agar plates and transferred to potato dextrose agar (PDA) plates every three weeks. To transfer the culture, a 1-cm$^2$ plug containing mycelium was placed on the new PDA Petri dish. The culture was grown at 25° C. for 2 days, and then stored at 4° C. until fermentations were conducted.

Once *P. irregulare* was actively growing on PDA, another 1-cm$^2$ plug was added to a 250 mL Erlenmeyer flask containing 50 mL of a sterile modified yeast-malt extract (YM) medium. This liquid medium consisted of yeast extract, 3.0 g/L; malt extract 3.0 g/L; peptone, 5.0 g/L; glucose, 10 g/L; and $K_2HPO_4$, 0.684 g/L, pH to 6.0 (1 N HCl). All reagents were purchased from Fisher Scientific. This inoculated medium was incubated at 150 rpm and 25° C. for 2 days in an orbital shaker (New Brunswick Scientific, model KC-25D, USA). A Kinematica Polytron homogenizer was used to blend this seed culture for 10 seconds at the highest rpm setting. Experimental flasks containing 45-mL of sterile YM media were inoculated with 5-mL portions of blended seed culture and incubated in an orbital shaker at 150 rpm under varying temperatures.

The effect of temperature on biomass yield and lipid production was studied at 14° C., 21° C., and 28° C. Triplicate fermentation flasks were sampled to construct biomass growth and lipid production curves over a period of 7 to 12 days depending on the fermentation temperature.

The mycelial growth of *Pythium irregulare* was expressed as dry cell weight per volume of media: mg/mL. Each daily harvest sample was filtered through Whatman No. 1 filter paper and washed with dionized water. These mycelial cells were transferred to pre-weighed tubes and then freeze dried (Labconco) at −50° C. and 0.15 Mbar vacuum until a constant weight was achieved, typically within 36 hours. Undiluted filtrate was retained and stored at −20° C. until a residual glucose analysis was performed.

The residual glucose concentration of the filtrate was analyzed using an HPLC system (Shimadzu, model VP Series, Japan) equipped with a Prevail C18 column (150 mm×4.6 mm i.d.; Alltech Associates Inc., W.R. Grace & Co., USA) packed with 5 μm spherical particles. The mobile phase was distilled water set to a flow rate of 0.50 mL/min. The filtered samples were 25 μl in volume. Glucose elution was monitored using an ELSD (Shimadzu, model ELSD-LT, Japan) detector with a gain setting of 6 and temperature of 70° C. Filtered house air was the nebulizer gas. Shimadzu EZ Start software version 7.2 was used for integration analysis.

Lipids were extracted from the dried biomass by a modified procedure using a 3:2 hexane isopropanol mixture (v/v; HiP). The dried mycelia (~0.25 g) were suspended in 10 mL of HiP, masticated for 1 min at high speed with a Kinematica Polytron homogenizer, and centrifuged at 3000 rpm for 10 min. The supernatant was decanted and saved. This extraction procedure was repeated twice for the residue, and the three supernatants were combined. The addition of 10 mL of 0.47 M sodium sulfate to the combined supernatants broke the emulsion and removed any extracted non-lipids. The upper hexane-rich phase containing the lipids was filtered with Whatman No. 1 paper and transferred to a pre-weighed tube for complete hexane evaporation under nitrogen at roughly 50° C. The dry weight of this residue was considered the total weight of lipids. The dried lipids were suspended in 2 mL hexane and stored at −80° C.

A rapid micro-scale procedure converted the triglycerides present in the lipid samples to fatty acid methyl esters (FAMEs). An aliquot of lipid/hexane sample was transferred to glass tubes to yield approximately 2 mg of lipid. This aliquot was diluted with hexane to a volume of 0.5 mL. 1M Sodium methoxide in dry methanol (20 μl) was then added, and the mixture vortexed to ensure thorough mixing. The addition of sodium methoxide created a cloudy solution as sodium-glycerol derivatives precipitated. This room temperature reaction was stopped after 5 minutes by the addition of acetic acid (4 μl). The solvents were evaporated using the same heating block design as previously described. Once the sample was dry, hexane (1 mL) was added and the mixture was centrifuged at 1500 g for 2 minutes. The supernatant layer was decanted, and an aliquot was taken directly for GC analysis. A known amount of heptadecanoic acid methyl ester (17:0) (Sigma Chemical) serving as an internal standard was added to the aliquots after derivatization to FAMEs. All FAMEs were identified by the retention index of the standards in a 37-FAME mix purchased from Sigma Chemical. All reagents were provided by Fisher Chemicals unless otherwise noted.

The FAME composition was determined using a gas chromatograph (Shimadzu, model GC-17A, Japan) equipped with a flame ionization detector (FID) and a split injector with a split to splitless ratio of 10 to 1. Shimadzu Class VP software version 5.0 was used for the integration analysis. This apparatus was fitted with a DB-Wax bonded phase capillary column (60 m×0.25 mm×0.25 μM; Agilent Technologies, J&W Scientific, USA). Samples (5 μl) were injected at 180° C.; after 6 min the oven temperature was raised at 3 C.°/min to 204° C.; and then 5 C.°/min to 240° C., where it was held for 25 min. Helium was used as the carrier gas at a flow rate of 1 mL/min. The injector and detector temperatures were 250° C. and 275° C., respectively.

The SAS software (version 9.1 by SAS Institute Inc., NC, USA) was used for all statistical analyses among biomass yields, lipid yields, and FAME oil compositions.

The effects of temperature on lipid production and glucose utilization were investigated (FIG. 1A). Maximum mycelial productions ($X_{max}$) were 6.52, 5.25, and 4.40 mg/mL at 14° C., 21° C., and 28° C., respectively. A least significant difference test (LSD) at the 95% level found all three $X_{max}$ values to be statistically different ($\Delta X_{max}$ greater than 0.299 mg/mL). Growth at 14° C. was the slowest of the three temperatures as $X_{max}$ was not reached until 7 days. The 28° C. and 21° C. fermentations achieved their respective $X_{max}$ value within 3 and 4 days. All fermentations demonstrated a death phase as noted by the slight decline in mycelial dry weight after $X_{max}$ was achieved.

Figure 1B:
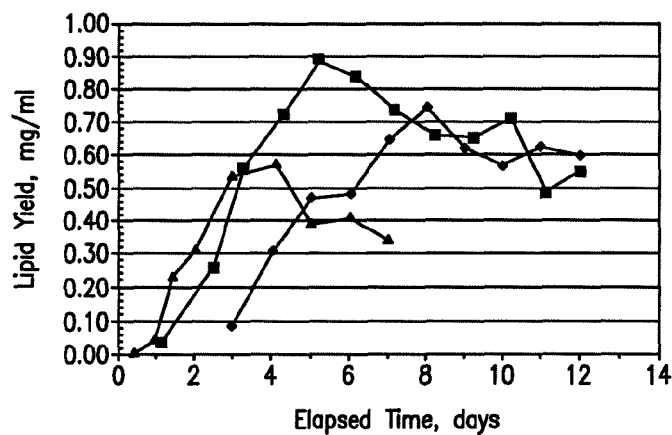

Even though the 14° C. treatment resulted in the largest $X_{max}$ value, a greater lipid production based on volume of media was realized at 21° C., 0.893 mg/mL (FIG. 1B). The remaining lipid production values were 0.744 and 0.572 mg/mL for 14 and 28° C., respectively. As with $X_{max}$, values, all three temperatures gave statistically different maximum lipid production values at the 95% confidence level.

The greatest percentage of oil in the biomass occurred when biomass cultured at 21° C. with 17.0% at the peak biomass production, 4 days. The oil content at the peak biomass production for 28° C. was 16.4%, which also occurred at 4 days. The maximum lipid yield at 14° C. and 8 days was only 12.0% of the biomass. Mycelial yield was considered the total weight of biomass and intracellular oils.

Figure 1C:
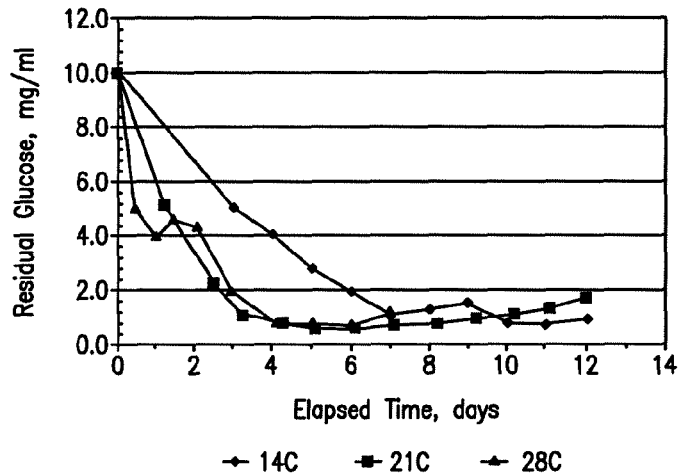

Glucose was assumed to be the main carbon source in the YM media. The residual medium glucose concentration at each sampling interval is included in FIG. 1C for each temperature tested. For all cases, the glucose concentration decreased to an average value of 0.93±0.31 mg/mL after maximum biomass was achieved.

Figure 2:
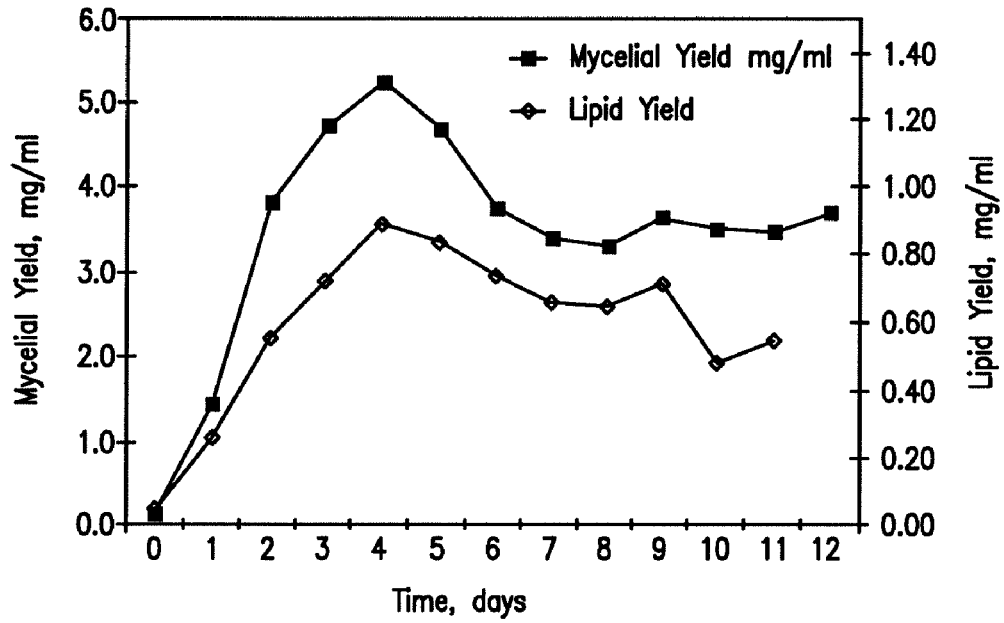
FIG. 2 illustrates the time course for mycelial and lipid yield for *P. irregulare* at 21° C. in submerged culture.

The elapsed time to achieve $X_{max}$ and maximum lipid production corresponded to within a day of each other. FIG. 2 combines the biomass growth curve and the lipid production profile for 21° C. Oil production can be considered mix-growth associated since accumulation was realized during both the exponential and stationary growth phases. There were appreciable decreases in oil concentration in early death phase possibly due to the consumption of this potential energy source over available glucose.

Figure 3:
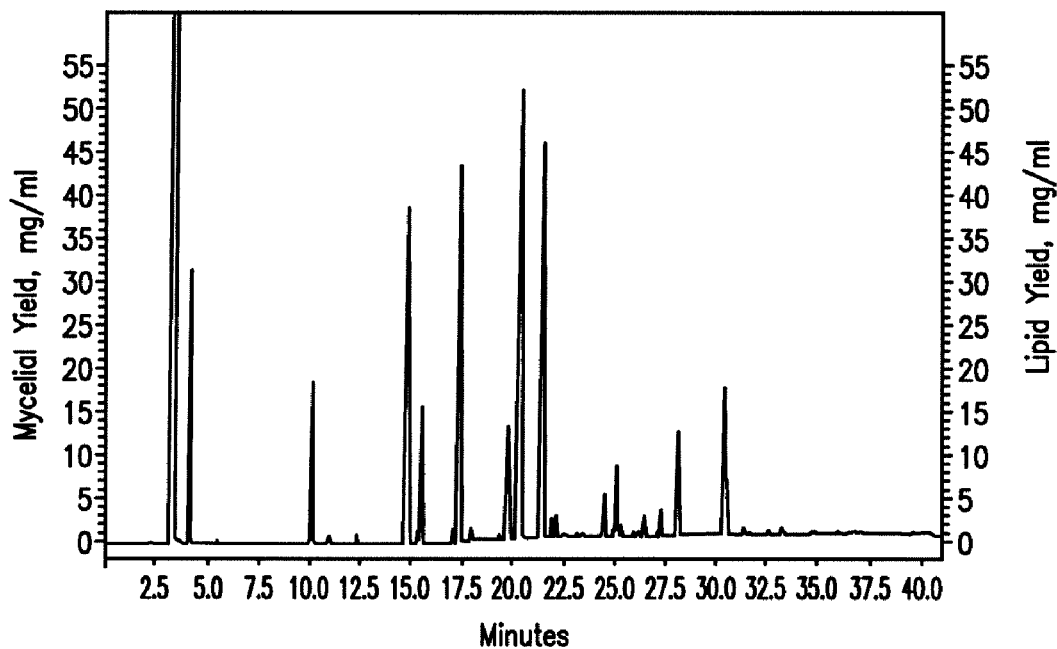
FIG. 3 is a gas chromatogram (GC) of fatty acid methyl esters (FAMEs) contained in *P. irregulare* oil extracted after 4 days growth as described in the example section, below.

Table 1, below, shows the composition of the individual and total fatty acid methyl ester (FAME) content of the lipid extract for maximum mycelial yield, $X_{max}$, while an example gas chromatogram is presented in FIG. 3. A least significance difference test (LSD) at the 95% level (a=0.05) was performed to test for differences in the FAME wt % between temperatures. The LSD values used for this comparison are listed in Table 1 along with indications for differences between temperatures.

The main components of all the oils tested were palmitic (C16:0) and oleic (C18:1) acids. The 28° C. oil had the only significant difference in wt % of these compounds: palmitic acid composition was greatest at 29.8 wt %. Other statistical significant differences were noted with mysteric (C14:0), γ-linoleic (C18:3), ARA and EPA. Fungal production of mysteric acid was maximized at 14° C., while growth at 28° C. promoted greater γ-linoleic acid.

EPA was the most abundant PUFA, comprising 3-11 wt % of the total FAMEs; maximum EPA composition was realized for *P. irregulare* growth at 14° C. and 8 days. The EPA content at 14 and 21° C. falls within in the range (6 to 12%) reported elsewhere for *P. irregulare* growth on various substrates. Growth at 28° C. yielded the significantly lowest EPA and ARA FAME content.

TABLE 1

| Fatty Acid Methyl Ester | $C_{q:r,\omega}$ | $LSD^{NB}$ (%) | Weight % 14° C. (8 days) | 21° C. (4 days) | 28° C. (3 days) |
|---|---|---|---|---|---|
| Myristic | $C_{14:0}$ | 1.40 | $11.1^{b,c}$ | 9.4 | 9.17 |
| Palmitic | $C_{16:0}$ | 2.25 | 23.8 | 25. | 29.8x' |
| Palmitoleic | $C_{16:1}$ | 2.45 | 6.73 | 5.7 | 6.61 |
| Stearic | $C_{18:0}$ | 0.26 | 5.11 | 5.1 | 4.94 |
| Oleic | $C_{18:1\omega9}$ | 4.32 | 22.5 | 21. | 23.7 |
| Linoleic | $C_{18:2\omega6}$ | 0.89 | 10.7 | 11. | 11.2 |
| γ-linoleic (GLA) | $C_{18:3\omega9}$ | 0.33 | $1.01^{b,c}$ | 0.5 | 362ab |
| Arachidic | $C_{20:0}$ | 1.08 | 0.71 | 1.0 | 0.96 |
| cis-1 l-eicosenoic | $C_{20:1\omega9}$ | 1.40 | 1.28 | 2.1 | 1.28 |
| arachidonic (ARA) | $C_{18:4\omega9}$ | 0.64 | 5.32 | 5.1 | $3.03^{a,b}$ |
| eicosapentaenoic | $C_{20:5\omega3}$ | 2.02 | $10.9^{b,c}$ | 8.8 | $3.47^{a,b}$ |
| Total | | | 98.5 | 96. | 97.8 |
| Unknown | | | 1.5 | 3.6 | 2.6 |
| 100 × ARA/EPA | | | 48.8 | 57. | 87.3 |

$C_{q:r,n}$: q is the number of carbons, r is the number of double bonds, ω is the position of the first double bond; NB = based on t = 2.7765, α = 0.05, error degrees of freedom = 4, r = 3; a = statistically different from 14° C. at a 95% level; b = statistically different from 21° C.; c = statistically different from 28° C. at a 95% level FIG. 3 illustrate the gas chromatogram of FAMEs contained in *Pythium irregulare* oil extracted after 4 days growth at 21° C. in a modified yeast-malt extract medium; 1=myristic acid, 2=palmitic acid, 3=palmitoleic, 4=internal standard (C17:0), 5=stearic acid, 6=oleic acid, 8=linoleic acid, 9=arachidic acid, 10=cis-11-eicosenoic, 12=arachidonic (ARA) acid, 13=eicosapentaenoic (EPA) acid.

Example 2

*Pythium irregulare* (ATCC 10951) was grown in submerged cultures in a YM media at 21° C. and 150 rpm. Fungal biomass was harvested after four days of fermentation, separated by filtration (Whatman No. 1 filter paper), and freeze dried (Labconco) at 0.15 bar vacuum and −50° C. Fermentation temperature and time were chosen after previous experimental results found maximum oil production occurring at these conditions. The freeze dried biomass was ground using a mortar and pestle to reach an average particle size of 200 μm. This solid particle size was determined using 24 and 48 mesh sieve trays, 250 pm and 150 pm, respectively.

The SFE apparatus schematically illustrated in FIG. 4 is a single-pass flow system utilized to integrate explosion and extraction processes. A four-way connection after the reactor allows for direct transition from explosion pretreatment to SFE. This example investigated the SFE portion of untreated fungal biomass. During this process, the explosion valve (7) remained closed.

Referring to FIG. 4, carbon dioxide from a cylinder (A) passed through an ice bath (K) and compressed to the operating pressure by a high-pressure syringe pump (B; Teledyne Isco, model 260-D, USA). The syringe pump operated in a constant pressure mode that maintains the high-pressure environment required for SFE. The compressed fluid passed through a coil (D), which was submerged in a constant-temperature water bath (C); the fluid continued to flow into the extractor vessel (E; Thar Technologies, USA) that was also immersed in the water bath (C). During extractions, the $CO_2$ passed through this reactor to a ⅛" three way-two stem valve (5; High Pressure Equipment Company, 15-15AF2, USA). One valve inlet (5a) controlled the $CO_2$ flow; the other inlet (5b) controlled gravity fed hexane. The $CO_2$ was allowed to expand at ambient pressure after this valve when the gas bubbles in a cold hexane trap (I) containing roughly 8 mL of hexane. The reduction in pressure caused the solubilized lipids to separate from the $CO_2$ and precipitate in the hexane trap. The depressurized $CO_2$ continued to flow through a digital flow meter (H; Omega Engineering, FMA 2300, USA) before being vented.

The water bath was equipped with a submersible electrical heater with PID control (Fisher Scientific, model Isotemp 2150, USA) to maintain a temperature ±0.2° C. The temperature of the flow control valve (5a) was maintained above the water bath temperature by wrapping heating tape (J) around this valve, the micrometering valve (6), and the remaining downstream tubing leading to the hexane trap. Keeping the downstream connections above the reactor temperature reduced chances of premature oil deposition in these connections. Prior to sampling, approximately 3 to 5 mL of hexane was gravity fed through these connections to remove any fungal oil that accumulated during the sampling interval. This hexane rinse was collected in the hexane trap.

The system pressure was monitored in two places: at the syringe pump and at the 4-way connection just downstream from the extraction vessel. The syringe pump (B) was equipped with an internal pressure sensor, while an Omega PX-305 pressure sensor (accuracy 0.25% BFSL) was installed for downstream monitoring. In-house software logged the pump pressure and pump $CO_2$ flow rate as well as the PX-305 pressure reading and Omega FMA-2300 volumetric flow rate readings during all extraction runs.

The extraction vessel was a 75 mL finger-tight reactor from Thar Technologies (Pittsburgh, Pa., USA) with measurements of 103 mm×30 mm i.d. Steel frits located at the inlet and outlet of the cylindrical shaft allowed for the biomass and glass beads described later to remain in the vessel. These frits also promote even distribution of the $CO_2$ flow.

The reactor bed was a mixture of *P. irregulare* (MC %<2.0) and equal amounts (g) of 3 mm and 5 mm glass beads. The extraction vessel was loaded with 1.754 (±0.002) g of sieved fungal biomass mixed with 5 mm and 3 mm glass beads (45.0±0.5 g each) to facilitate uniform distribution of $CO_2$ and prevent channeling. Once the vessel was loaded with sample, another 15.0=0.2 g of 5 mm beads were added on top to decrease dead space.

The real solid density ($\rho_s$) of the crushed *P. irregulare* was measured using a helium pycnometer (Micrometrics, model AccuPyc 1330, USA). The apparent bed density ($\rho_a$) was determined using the reactor volume and the mass of the total feed (*P. irregulare* and glass beads). The total porosity of the bed plus particles was determined using the true and apparent densities.

Before each SFE run, the $CO_2$ flow control valve (5a), micrometering valve (6), and tubing after the extraction vessel were flushed with hexane to remove any residual oil. Carbon dioxide was flushed through this tubing to evaporate remaining hexane. The extraction vessel and frits were cleaned with a cloth saturated with hexane and allowed to air dry.

Once the extraction vessel was incorporated into the SFE unit and at equilibrium with the water bath, the system was pressurized at the chosen operational conditions: Next, the flow control valve (5a) was opened to begin the extraction process. The operational conditions were a pressure of 20.6 MPa (3000 psig), temperature of 40° C., and an average solvent flow rate of $3.94 \times 10^{-6}$ kg/s.

For sampling the extractable material, the $CO_2$ flow was stopped temporarily, and the downstream connections were flushed with hexane to collect any prematurely precipitated lipid. The $CO_2$ flow was resumed, and the hexane trap was replaced with a new tube filled with 8 mL of hexane. Extract samples were collected after 5, 10, 15, 20, 30, 40, 50, 60, 75, 90, 105, 120, 150, 180, 210, and 240 minutes.

The weight of oil collected during a sampling interval was determined gravimetrically by evaporating the hexane under a gentle stream of nitrogen. The dried oil was resuspended in 2 mL of hexane and stored under nitrogen at 50° C. Cumulative oil extracted over time was used as a model parameter.

The residual oil remaining in the fungi as well as the oil in non-$CO_2$ treated fungal biomass was extracted using liquid solvents. The *P. irregulare* biomass was suspended in 30 mL of a 3:2 (v/v) hexane-isopropanol mixture (HiP), then masticated for one min. at high speed with a Kinematica Polytron homogenizer. This slurry was centrifuged at 3000 rpm for 10 min. The supernatant was decanted and saved. This extraction procedure was repeated twice for the residue while combining the three supernatants. The addition of 10 mL of 0.47 M sodium sulfate to the combined supernatants broke the emulsion and removed any extracted non-lipids. The upper hexane lipid-rich phase was filtered with Whatman No. 1 paper and transferred to another tube for complete hexane evaporation in a heating block at 50° C. under a steady supply of nitrogen. The dry lipid weight was the amount of residual oil in the treated *P. irregulare* biomass. The dried lipids were suspended in 2 mL of hexane and stored at −80° C. for future methyl ester analysis by gas chromatography.

The maximum amount of extractable material was determined to be the sum of the weight of SFE extracted material and HiP solvent extracted material.

The triglycerides present in the oil samples were converted to fatty acid methyl esters (FAMEs) using a rapid micro-scale procedure as described in Example 1.

The extract samples were analyzed using a GC-FID system (Shimadzu, model 17A, Japan) equipped with split-injector. This apparatus was fitted with a DB-Wax bonded-phase capillary column (60 m; 0.25 mm i.d.; 0.25 pun film thickness) (Agilent Technologies, J&W Scientific, USA). Helium was used as the carrier gas at a flow rate of 1 mL/min. Samples (5 µl) were injected at 180° C.; after 6 min the oven temperature was raised at 3 C.°/min to 204° C.; and then 5 C.°/min to 240° C., where it was held for 25 min. The injector and detector temperatures were both set to 250° C.

The physical properties of the fungal cells were measured. The apparent particle density was 676 kg/m$^3$, and the real solid density ($\rho_s$) was 1398±5.4 kg/m$^3$. The porosity of the cells was calculated to be $\epsilon_p = 1-(\rho_p/\rho_s) = 0.516$. The bed void fraction, c, was found to be 0.429., The maximum extractable oil averaged 0.168±0.02 g. Table 2, below shows these data and other information used in the mathematical modeling of the OEC.

TABLE 2

| Parameters | | | |
|---|---|---|---|
| Pressure | P | 20.7 | MPa |
| Temperature | T | 40 | ° C. |
| Bed Volume | $V_{bed}$ | $7.534 \times 10^{-5}$ | m$^3$ |
| Density of $CO_2$ | $\rho_{co2}$ | 850 | kg/m$^3$ |
| Mass Flow Rate of $CO_2$ | $Q_{co2}$ | $3.94 \times 10^{-6}$ | kg/s |
| Bed Porosity | $\epsilon$ | 0.429 | — |
| Real particle density | $\rho_s$ | 1398 | kg/m$^3$ |
| Mass of Feed | $m_f$ | $1.75 \times 10^{-3}$ | kg |
| Porosity of Particles | $\epsilon_p$ | 0.516 | |
| Initial solute mass ratio in the particle | $x_0$ | 0.096 | kg solute/kg feed |

Figure 5:
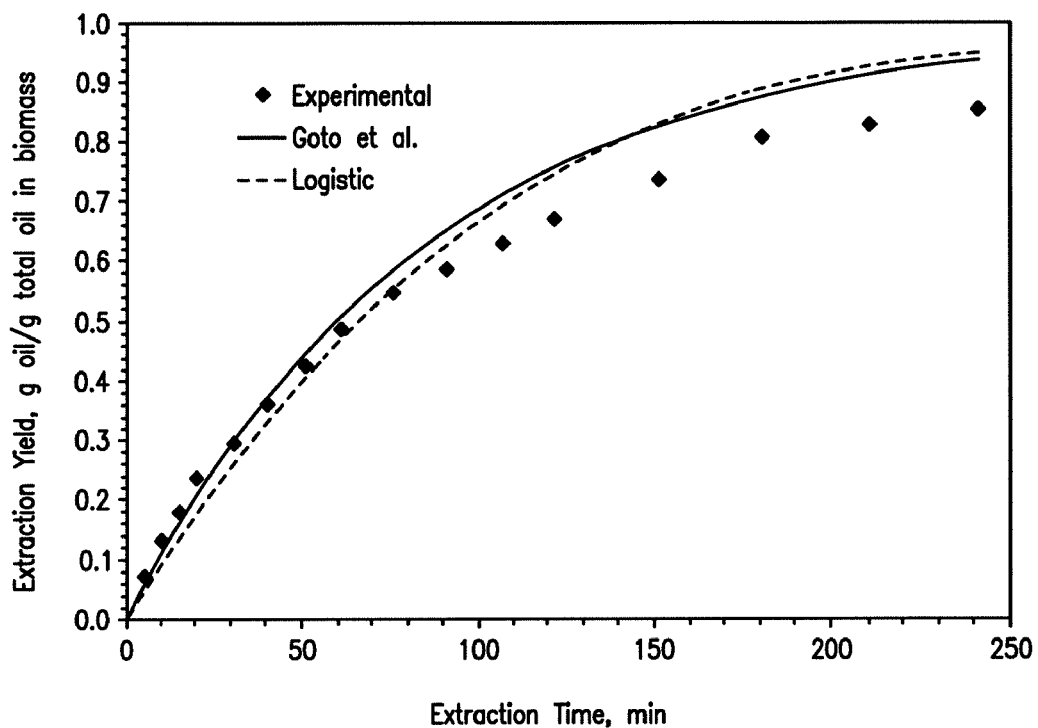
FIG. 5 compares the experimental and modeled overall extraction curves (OEC) for supercritical fluid extraction (SFE) processes of *P. irregulare* oisl as described herein.

FIG. 5 shows the overall extraction curve of *P. irregulare* oil including the curves obtained using the models of Goto et al. and Martinez et al. The OEC has a constant extraction rate (CER), falling extraction rate (FER), and diffusion controlled (DC) period. The CER period, defined by the linear equilibrium relationship between solute and solvent, occurs during the first 20 minutes until roughly 30% of the available lipids were removed. After this period, the extraction rate slowly began to decrease (FER period) and eventually entered a DC extraction period by 210 minutes when almost 80% of the oil had been extracted. The intracellular mass transfer of the oil through the fungal cells to the cellular surface is the extraction limiting phenomena during this period.

Figure 6:
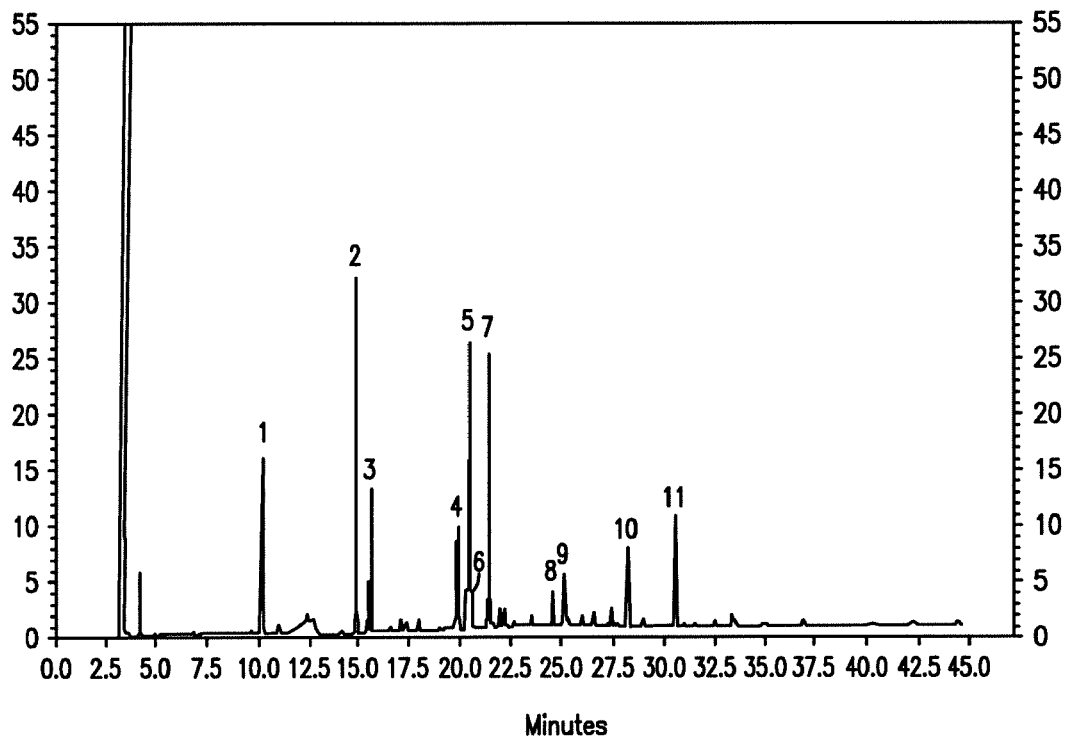
FIG. 6 is a GC of FAMEs contained in *P. irregulare* oil.

Extracted oil samples were methylated and analyzed for FAME content. The FAME composition of the $CO_2$ extracted oil is listed in Table 3 with peaks identified in a GC chromatogram in FIG. 6. EPA was the most abundant PUFA extracted, averaging 8.5% of the total weight of oil. ARA composed 4.8% of the total SFE oil. The time course of individual fatty acid extraction was determined by analyzing the oil sample at each time step. No FAME at any time step varied more than one standard deviation from the average.

The relative recoveries of the FAMEs initially quantified from HiP extractions are also provided in Table 3. The recovery was the ratio of mass of individual FAMEs in the SFE oil to the mass of individual FAMEs extracted from non-$CO_2$ SFE treated biomass using HiP. Consequently, there is a potential for more than 100% recovery of an individual FAME since the cumulative sum of SFE oil plus any residual oil in the biomass (0.168 g) is greater than the oil obtained from solely HiP extraction (0.135 g).

Over 100% recovery was accomplished for shorter chain, low-molecular weight compounds like palmitic and palmitoleic acids, which means that SFE with $CO_2$ is able to extract more of these compounds than liquid solvent extraction. As the structure of the fatty acid became more complex, the percent recovered decreased. This suggests the potential for SFE fractionation of fatty acids based on molecular weight. Treatment with supercritical $CO_2$ removed up to 81% of available EPA and ARA initially found in the *P. irregulare* oil extracted using HiP.

TABLE 3

| FAME | $C_{q:r,\omega}$ | Wt. (%) of SFE Oil | Relative Recovery |
|---|---|---|---|
| Myristic | $C_{14:0}$ | 9.70 | 101 |
| Palmitic | $C_{16:0}$ | 24.4 | 106 |
| Palmitoleic | $C_{16:1}$ | 7.60 | 106 |
| Stearic | $C_{18:0}$ | 5.47 | 104 |
| Oleic | $C_{18:1\omega9}$ | 19.1 | 77.6 |
| Linoleic | $C_{18:2\omega6}$ | 10.9 | 70.9 |
| -linoleic (GLA) | $C_{18:3\omega6}$ | 0.67 | 67.5 |
| Arachidic | $C_{20:0}$ | 0.75 | 51.9 |
| cis-11-eicosenoic | $C_{20:1\omega9}$ | 2.37 | 86.0 |
| arachidonic (ARA) | $C_{20:4\omega6}$ | 4.74 | 89.3 |
| eicosapentaenoic | $C_{20:5\omega3}$ | 8.24 | 73.2 |
| Total |  | 94.0 |  |
| Unknown |  | 6.0 |  |

$C_{q:r,\omega}$: q is the number of carbons, r is the number of double bonds, ω is the position of the first double bond; Recovered % = mg FAME in SFE oil/mg FAME HiP extracted oil; Total SFE oil is 168 mg, while HiP oil is 135 mg.

Hexane-isopropanol (HiP) extractions of oil from non-$CO_2$ treated *P. irregulare* biomass yielded an $x_0$-value of 0.077 kg oil/kg feed. From this ratio, supercritical $CO_2$ extractions would achieve a yield of 1.0 within 4 hours of extractions at the current experimental conditions. A side-by-side comparison of the FAME composition of the two oils is provided in Table 4. Both palmitic and oleic acids are main components in both types of extracted oils. Another significant contributor for both oils is linoleic acid. The two PUFAs of interest, EPA and ARA together comprise less than 16.1% of the HiP extracted oil and 12.9% of the $CO_2$ SFE oil.

A least significance difference test (LSD) at the 95% level (a=0.05) was performed to test for differences in the FAME wt % between extraction methods. The LSD values used for this comparison are listed in Table 3.4. There is a statistical difference between the weight percentages of palmitoleic acid. The SFE oil contained a greater percentage of palmitoleic acid than the HiP extracted oil. There were no differences detected between ARA and EPA wt %. This suggests that either method is applicable to the extraction of PUFAs.

TABLE 4

| FAME | $C_{q:r,n}$ | LSD (%) | Weight % HiP | Weight % $CO_2$-SFE |
|---|---|---|---|---|
| Myristic | $C_{14:0}$ | 3.07 | 9.47 | 9.70 |
| Palmitic | $C_{16:0}$ | 2.30 | 25.9 | 24.4 |
| Palmitoleic | $C_{16:1}$ | 1.83 | 5.75* | 7.60 |
| Stearic | $C_{18:0}$ | 1.01 | 5.14 | 5.47 |
| Oleic | $C_{18:1n9}$ | 4.93 | 21.5 | 19.1 |
| Linoleic | $C_{18:2n6}$ | 1.54 | 11.0 | 10.9 |
| γ-linoleic (GLA) | $C_{18:3n6}$ | 0.95 | 0.56 | 0.67 |
| Arachidic | $C_{20:0}$ | 1.54 | 1.06 | 0.75 |
| cis-11-eicosenoic | $C_{20:1n9}$ | 2.52 | 2.10 | 2.37 |
| arachidonic (ARA) | $C_{20:4n6}$ | 1.12 | 5.12 | 4.74 |
| eicosapentaenoic | $C_{20:5n3}$ | 2.36 | 8.84 | 8.24 |
| Total |  |  | 96.4 | 94.0 |
| Unknown |  |  | 3.6 | 6.0 |

Cq:r,n: q is the number of carbons, r is the number of double bonds. ion of the first double bond; NB = based on t = 2.7765, a = 0.05, error degrees of freedom = 4, r = 3; *significant different from SFE oil at 95% level.

The overall extraction curve for $CO_2$-*Pythium irregulare* system shows the typical constant extraction rate, falling extraction rate, and diffusion-controlled periods. The Goto et al. model provided a best fit to the constant extraction rate period; however, this model did not adequately represent the diffusion controlled regime where intracellular mass transfer of the oil through the fungal cell controls the extraction process. The Martinez et al. model captured the shape of the OEC, but slightly over-predicted the experimental values at the later stages of extraction.

The major PUFAs present if the SFE oil was EPA and ARA; however, these represented less than 13% of the total oil weight. Within 90 minutes supercritical $CO_2$ removed approximately 81% of the initial PUFAs. SFE extraction was compared to HiP extraction and the only component difference accounted by the HiP extraction was found in palmitoleic acid. SFE with $CO_2$ within four hours can remove the same amount of oil from *P. irregulare* biomass as well as produce an oil with statistically similar amounts of PUFAs as HiP extraction.

Example 3

*Pythium irregulare* (ATCC 10951) was grown in submerged culture in a YM media at 21° C. and 150 rpm. Fungal biomass was harvested after four days of fermentation, separated by filtration, and freeze dried (Labconco) at 0.15 bar vacuum and −50° C. This freeze dried biomass (MC %<2) was ground using a mortar and pestle to reach an average particle size of 200 μm. This solid particle size was determined using sieve trays with 24 and 48 mesh (250 μm and 150 pm). Previous testing found the real particle density to be 1398±5.4 kg/m³.

Supercritical $CO_2$-explosion pretreatments of the fungal biomass were performed using the same apparatus used for SFE of oil from fungal biomass (FIG. 4). A four-way connection after the vessel allows for direct transition from explosion pretreatment to SFE. The explosion valve depicted in FIG. 4 was used to rapidly decrease the vessel pressure. The closed ¼ inch pneumatically actuated ball-valve (Swagelok, SS-83KS4-31C, USA) was opened by supplying nitrogen to the actuator.

Before each run, the $CO_2$-flow control valve and tubing downstream of the extraction vessel were flushed with hexane to remove any residual oil from previous runs. $CO_2$ was flushed through this tubing to evaporate remaining hexane. The extraction vessel and fits were cleaned with a cloth saturated with hexane and allowed to air dry. The extraction vessel was loaded with 1.754(±0.002) g of sieved fungal biomass mixed with 5 mm and 3 mm glass beads (45.0±0.5 g each) to facilitate uniform distribution of $CO_2$ and prevent channeling. Once the vessel was loaded with sample, another 15.0±0.2 g of 5 mm beads were added on top to decrease dead space. The extraction vessel was assembled and placed into a water bath maintained at a constant temperature.

Once all tubing connections were secured and outlet valves were closed, the vessel was pressurized with $CO_2$ from a syringe pump (Teledyne Isco, model 270D, USA) until the experimental soaking pressure was achieved, this pressure was monitored using a pressure transducer (Omega Engineering, PX-305, USA) located immediately downstream from the vessel. The fungal sample was subjected to the high pressure $CO_2$ for a controlled length of time to allow the $CO_2$ molecules to penetrate the cellular structure. Carbon dioxide was not allowed to flow through the vessel during this soaking phase. At the end of the soaking time, a rapid pressure release from soaking pressure to atmospheric pressure was imposed by opening the explosion valve downstream from the vessel.

The decrease in vessel pressure was recorded. The sampling frequency of the PX-305 pressure transducer ranged from 5000 to 100,000 Hz. These data were used to observe how quickly the pressure decreased within the vessel.

The SFE portion of an experimental run was performed at 20.6 MPa (3000 psi) and 40° C.; these conditions remained constant regardless of the explosion pretreatment conditions tested. The flow rate was maintained at an average $CO_2$ volumetric flow rate of 150 ml/min at the flow meter conditions, which corresponds to 3.94×10-6 kg/s. The average volumetric flow rate was constantly monitored. Extract samples were collected from the cold-hexane trap after 5, 10, 15, 20, 30, 40, 50, 60, 75, and 90 minutes. The weight of the lipid was determined gravimetrically by evaporating the hexane under a gentle stream of nitrogen at 50° C. After SFE, the fungal biomass was separated from the beads and further extracted with a hexane-isopropanol (HiP) mixture (3:2 v/v). The extracts resulting from both operations, i.e. the SFE oil and the HiP oil, were then tested for their fatty acid methyl ester (FAME) composition.

Explosion pretreatments were carried out at two different soaking pressures, 10.3 and 27.6 MPa (1500 and 4000 psi), and two different soaking times, 20 and 60 min. The temperature of the water bath was held at a constant 40° C.). (±0.2 C.°. At these conditions, the $CO_2$ density ranged from 658 to 905 $kg/m^{-3}$. Explosion pretreatment with SFE of the fungal cells were performed in duplicate at each set of explosion conditions. In addition, runs were performed that solely looked at the effects of explosion pretreatment on the residual fungal oil, i.e. no SFE of the fungal biomass.

The extraction yield of oil was determined to be the ratio between the weight of cumulative extracted oil and the weight of total oil available in the fungal biomass. In order to normalize all treatments, a common denominator was necessary for the extraction yield. SFE of non-$CO_2$ exploded fungal cells at 20.7 MPa and 40° C. had been investigated previously. The total extractable oil from supercritical $CO_2$ followed by HiP solvent extraction of the residues was 0.168 g (±0.019 g). This value was used when calculating all oil extraction yields.

All extracted samples underwent a rapid micro-scale transmethylation procedure to convert the fatty acids to their fatty acid methyl ester, FAME, equivalent. Each sample's FAME composition was determined using a gas chromatograph (GC-FID; Shimadzu, model 17A, Kyoto, Japan) equipped with a DB-Wax bonded phase capillary column (60 m×0.25 mm×0.25 μm; Agilent Technologies, J&W Scientific, USA). The carrier gas was helium at a flow rate of 1 mL/min. The temperatures of both the injector and the detector were set to 250° C. The column was heated to 180° C. for 6 min and programmed at 3 C.°/min to 204° C. then at 5 C.°/min to 240° C., where it was held constant for 25 min. Five microliter of sample was injected. Quantification of individual FAMEs was accomplished using the internal standard method with 30 μl of 1-mg/mL heptadecanoic acid methyl ester (Sigma Chemical; C17:0) added to each methylated sample.

Freeze-dried *P. irregulare* biomass (avg. Dp=200 pm, MC %<2) was subjected to a supercritical $CO_2$-explosion pretreatment to determine if this process would enhance the supercritical $CO_2$ extraction of intracellular PUFA-rich oils. This fungal biomass was in contact with high pressure $CO_2$ (10.3 MPa or 27.6 MPa) for a designated time (20 or 60 min). After this soaking phase, a rapid pressure release took place, and the oil was extracted via SFE with $CO_2$ over 90 min at 20.7 MPa and 40° C. ($\rho_{CO2}$=850 kg/m³) with a $CO_2$ flow rate of 3.94×10.6 kg/s. The extraction yield was calculated as the ratio of cumulative oil weight to total extractable oil from non-explosion pretreated fungal biomass (0.168 g).

Figure 7:
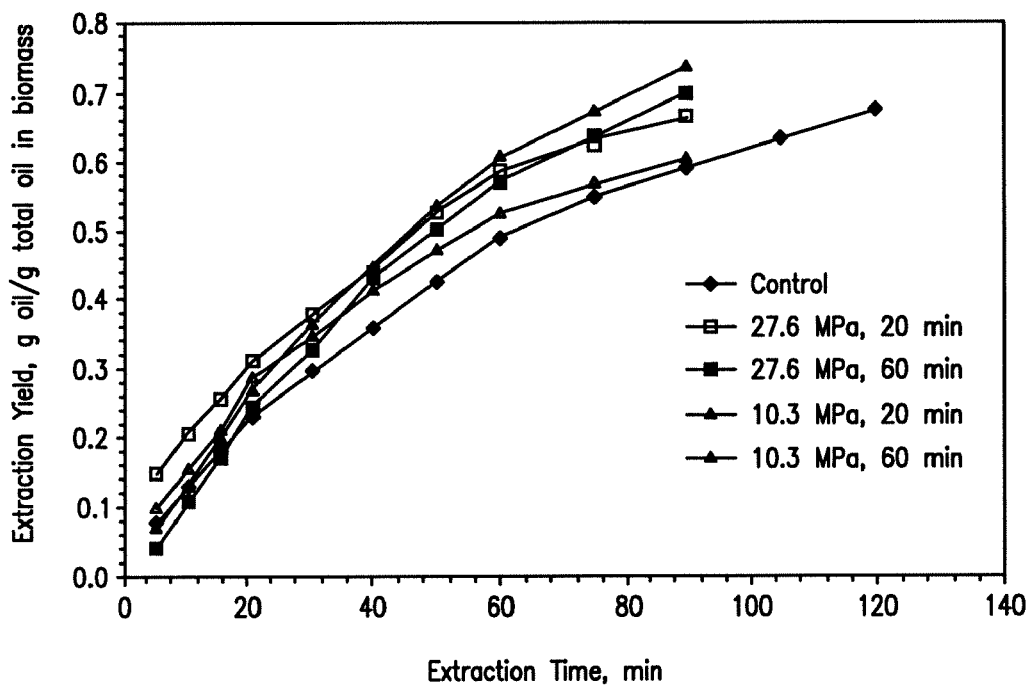
FIG. 7 illustrates the effect of $CO_2$ explosion pretreatment of SFE of PUFA-rich oil from *P. irregulare;*

The overall extraction curves (OEC) for each $CO_2$-explosion pretreatment condition and for non-explosion treated biomass are displayed in FIG. 7. All the OECs have the constant extraction rate period; however, the rates vary for time between 5 and 20 minutes. The (26.7 MPa, 60-min) treatment had the fastest extraction rate with 2.35 mg/min; the slowest extraction rate, 1.79 mg/min, occurred with the (27.6 MPa, 20-min) treatment. After 20 min of extraction, the 20-min runs exhibit a definite change in slope indicating the beginning of the falling extraction period. Both of these treatments started to approach diffusion controlled extraction after 60 minutes, which is sooner than the control and 60-min runs. Both 60-min treatments appear to run parallel to each other with no considerable change in extraction rate or flattening of the curve, which suggests these treatments stayed in the constant extraction period over the 90 minutes.

A 2×2 factorial ANOVA was performed on the extraction yields at 5, 20, 40, 60, and 90 minutes. The factors were soaking pressure and soaking time. A least significant difference test (LSD) at the 90% level was performed to test for differences between soaking pressures and times. The LSD values used for comparison of extraction yields are listed in Table 5 along with F-values. The F-values listed are the overall F-value ($F_{overall}$), the F-value associated with the soaking pressure ($F_{Psoak}$), and the F-value corresponding to the soaking time ($F_{Tsoak}$).

TABLE 5

| Extraction Time (min) | $LSD^{NB}$ (%) $\alpha = 0.10$ | $F_{overall}$ | $F_{Psoak}$ | $F_{Tsoak}$ |
|---|---|---|---|---|
| 5 | 0.0427 | 3.36* | 0.78 | 8.54* |
| 20 | 0.0512 | 2.09* | 2.41* | 1.44* |
| 40 | 0.0617 | 2.30* | 3.37* | 0.17* |
| 60 | 0.0953 | 0.58 | 0.73 | 0.27 |
| 90 | 0.0456 | 9.04* | 6.73* | 13.65* |

NB = based on t = 1.943, a = 0.10, error degrees of freedom = 6, r = 4; *contains a significant difference at a 90% level.

The overall F-values were significant at the 90% level for extraction yields at each time except for the 60-minute mark. A significant overall F-value meant that at least one soaking pressure or soaking time's extraction yield was different from the rest. The extraction yields for all treatments at 60 minutes were not statistically different from one another.

By the end of 90 minutes, the extraction yields covered a range of values from 0.593 to 0.743 (Table 6). Pretreatment with a 60-min soaking time did result in a statistically significant increase in extraction yield over the control and the 20-min treatments (p<0.010). The explosion pretreatment at (10.3 MPa, 60-min) provided the highest oil extraction yield of the four treatments, while the (10.3 MPa, 20-min) treatment showed no statistical enhancement of SFE over the control. The longer soaking time allowed for more $CO_2$ to penetrate the fungal biomass and rupture the cells when the vessel pressure rapidly decreased to atmospheric conditions.

TABLE 6

| Soaking Pressure (MPa) | Soaking Time (min) | Cumulative Oil (g) | Extraction Yield* |
|---|---|---|---|
| 27.6 | 20 | 0.112 | 0.665 |
| 27.6 | 60 | 0.118 | 0.701 |
| 10.3 | 20 | 0.102 | 0.610 |
| 10.3 | 60 | 0.125 | 0.743 |
| Control | — | 0.100 | 0.593 |

*significant differences at the 95% level are those greater than 0.0456. Yield based on 0.168 g total available oil in non-explosion treated biomass (Control).

For the 60-min treatments, a decrease in density produced a higher extract yield. Applying Brunner's diffusion generalization for this study, the diffusivity increased with the drop in density; therefore, more $CO_2$ was incorporated into the cellular structure and increased the number of broken cells during the explosion process. Consequently, more surface oil is available for extraction leading to a higher yield.

Despite the numerical increase in yield with the less dense $CO_2$, the difference between treatments at 60-min was not statistically significant at the 90% level (p-value <0.212).

There are notable differences in the extraction yields between treatment pressures for the 20-min soaking time. A significantly greater yield was calculated for treatment at 27.6 MPa over both the control and 10.3 MPa experiments (p-value <0.0117). The increase in yield can be attributed to the volatile nature of this physical process. The fungal biomass breaks apart because $CO_2$ escapes the cells in chaotic manner. Even though a lower pressure promotes better diffusion of the $CO_2$ molecules, the time allotted was not enough to allow sufficient $CO_2$ to penetrate the biomass. Consequently, the damage to the cells caused by the $CO_2$, at the higher pressure was greater than the damage at the lower pressure. As discussed later, the biomass realizes a greater drop in pressure over the same time frame for the 26.7 MPa explosions than the 10.3 MPa explosion treatments.

Figure 8:
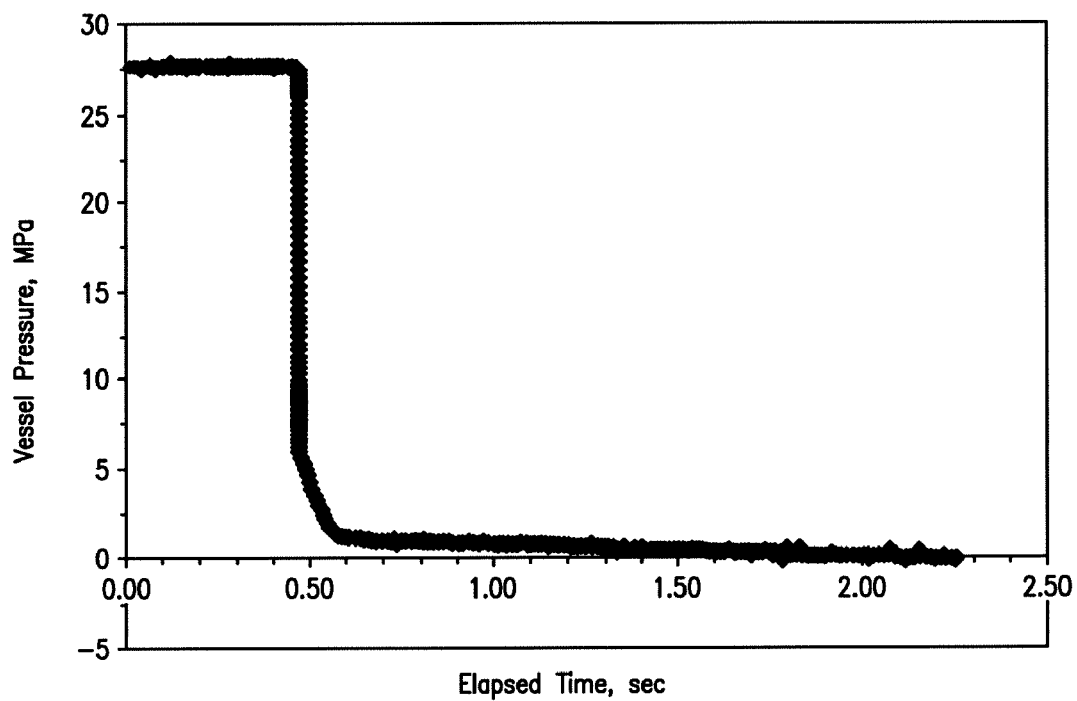
FIG. 8 illustrates the vessel pressure change during a $CO_2$ explosion process as described herein.
Figure 9:
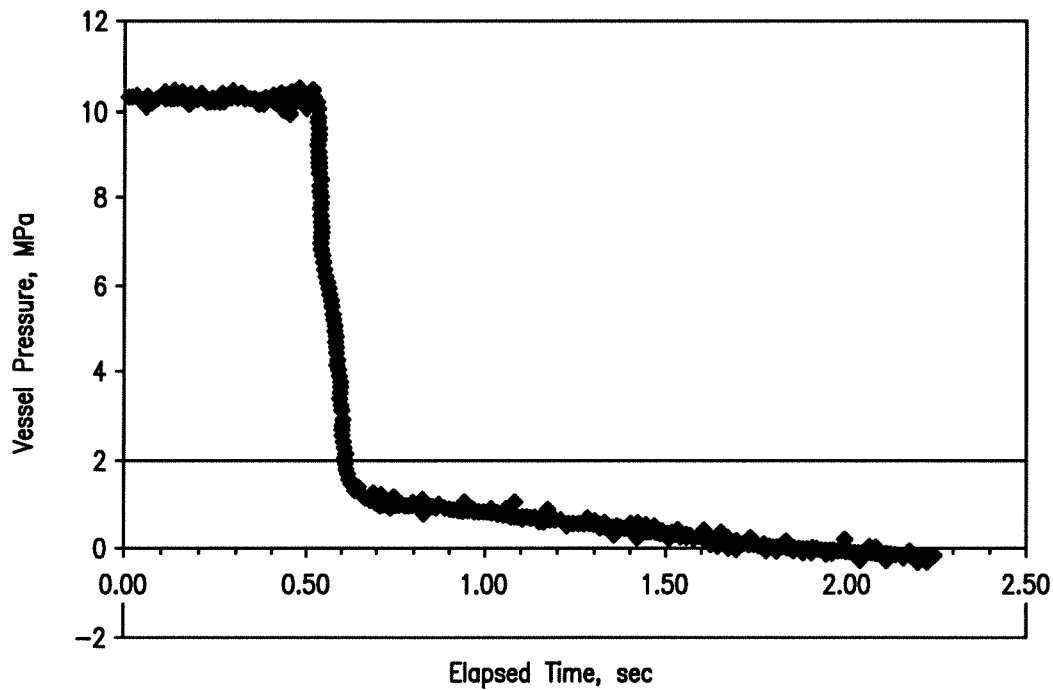
FIG. 9 illustrates the vessel pressure change during a $CO_2$ explosion process as described herein.
Figure 10:
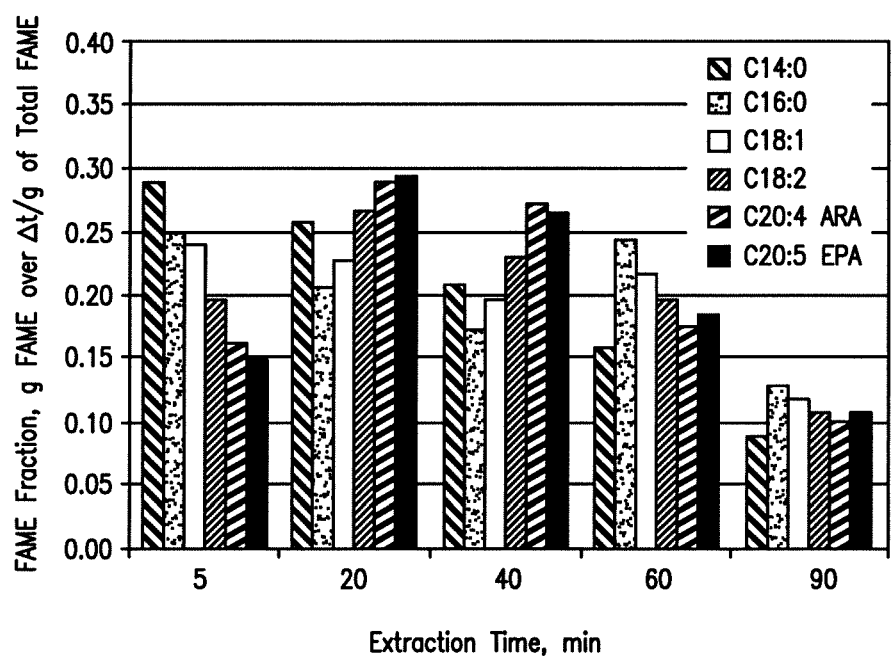
FIG. 10 illustrates the FAME distribution of SFE extracted *P. irregulare* oil obtained from a $CO_2$ explosion process as described herein.
Figure 11:
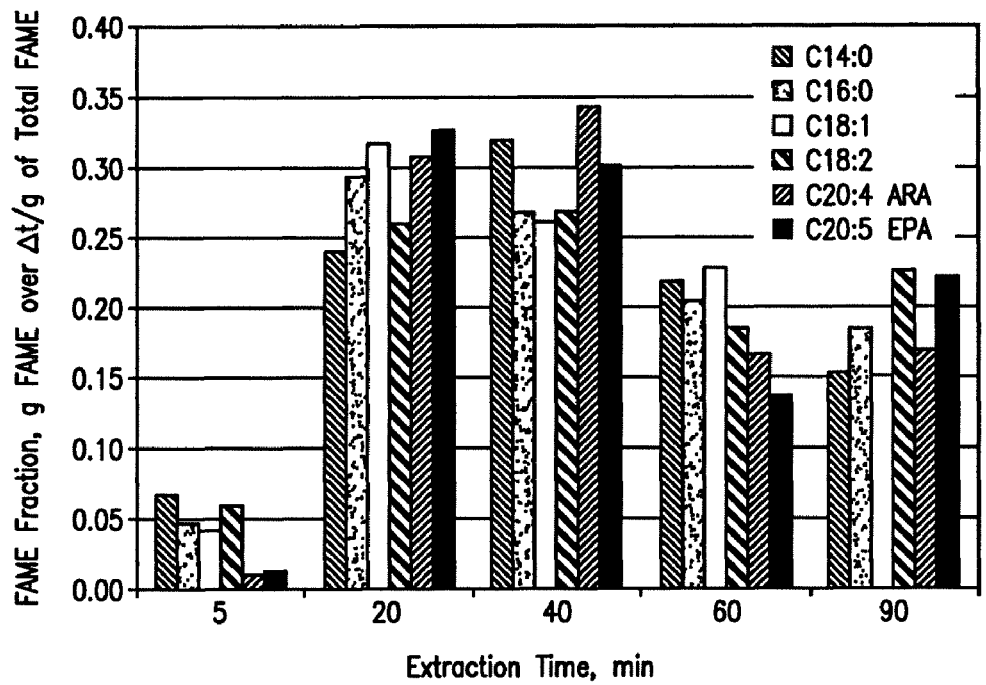
FIG. 11 illustrates the FAME distribution of SFE extracted *P. irregulare* oil obtained from another $CO_2$ explosion process as described herein.
Figure 12:
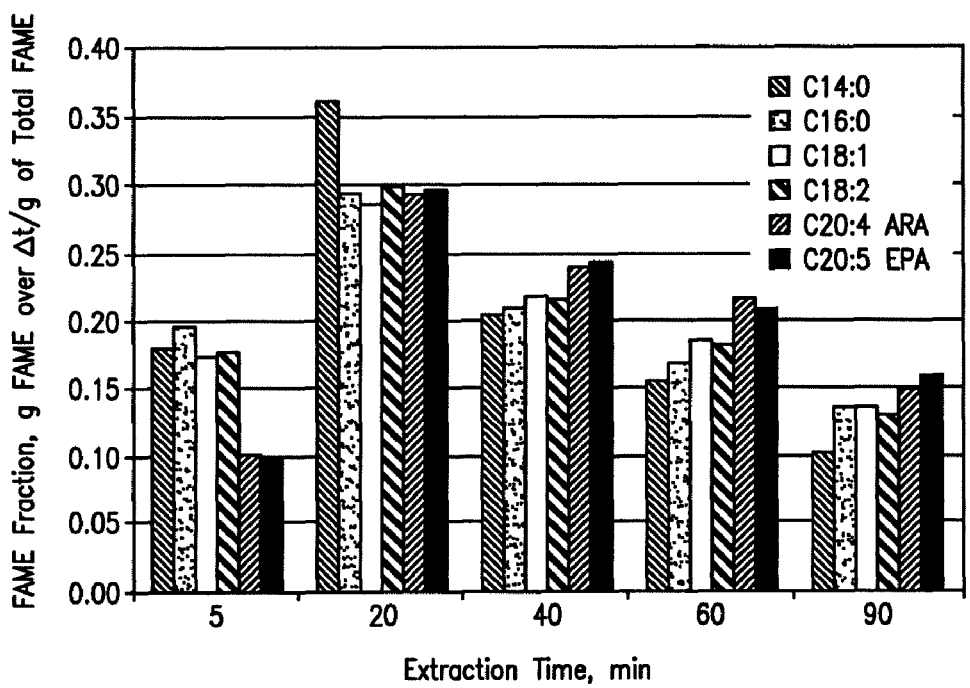
FIG. 12 illustrates the FAME distribution of SFE extracted *P. irregulare* oil obtained from another $CO_2$ explosion process as described herein.
Figure 13:
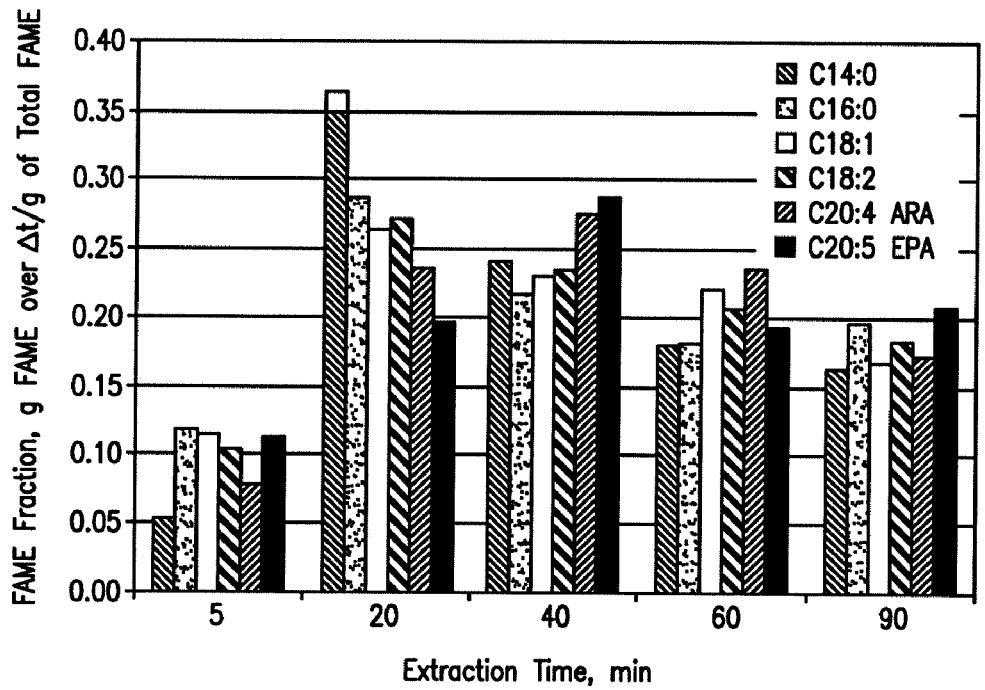
FIG. 13 illustrates the FAME distribution of SFE extracted *P. irregulare* oil obtained from another $CO_2$ explosion process as described herein.
Figure 14:
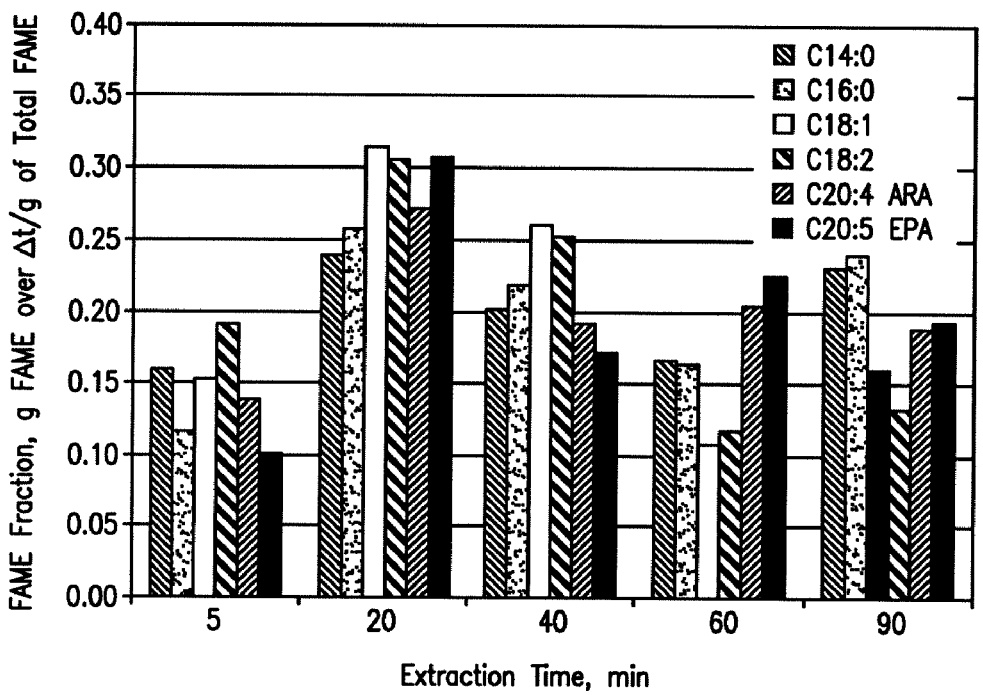
FIG. 14 illustrates the FAME distribution of SFE extracted *P. irregulare* oil obtained from another $CO_2$ explosion process as described herein.

The actual $CO_2$-explosion process is a very rapid, volatile phenomenon. The pressure reduction during the explosion process was recorded using data-logging software capable of handling a frequency up to 10,000 Hz. The pressure drops for 26.7 MPa and 10.3 MPa are presented in FIGS. 8 and 9, respectively. Within 0.10 sec, the pressure reduced 93% from 26.7 MPa to 1.85 MPa; a 72.8% reduction in pressure is seen for initial pressures of 10.3 MPa within the same time frame. Both scenarios had a vessel pressure of roughly 1.0 MPa after 0.20 seconds and decreased to atmospheric conditions after 2 seconds.

The FAME fractionations for select compounds at each explosion condition as well as the control (SFE only) are shown in FIGS. 10-14. The fractionation at 5, 20, 40, 60, and 90 minutes were determined from GC quantification via the internal standard method for the following compounds: myristic (C14:0), palmitic (C16:0), oleic (C18:1), and linoleic (C18:2) acids along with ARA (C20:4) and EPA (C20:5). The fractionation at each time interval was calculated as the ratio of the amount of FAME quantified within a time step to the total amount of the quantified FAME over 90 minutes.

Figure 15:
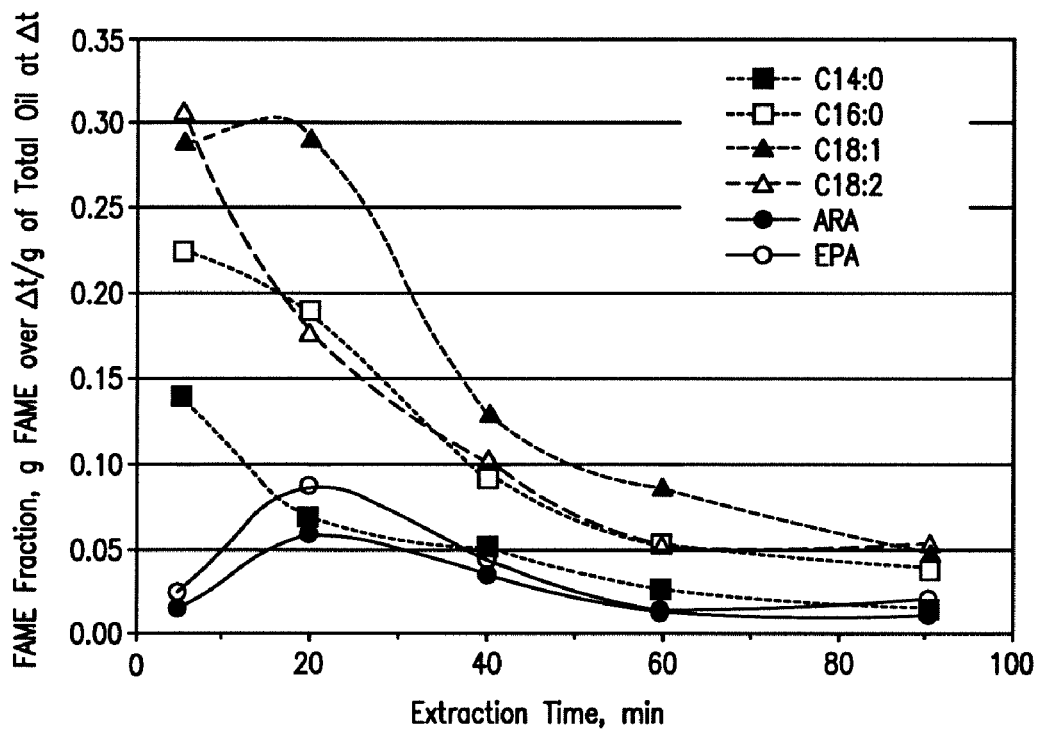
FIG. 15 illustrates individual FAME contribution to cumulative total oil during the SFE of oil from $CO_2$-explosion pretreated *P. irregulare* biomass.

For all cases of explosion pretreatment, SFE somewhat fractionated the lower molecular weight, saturated compounds from the higher molecular weight and more unsaturated FAMEs like EPA and ARA. The lower-molecular weight compounds were extracted during the beginning of the process and nearly depleted toward the end of the extraction run, whereas the PUFA fractions, EPA and ARA, appeared to increase toward the end of the process. This increase is important when considering that downstream recovery and purification processing of PUFAs and other microbial products can account for 70-80% of total production costs. Collecting the oil after 40 minutes can reduce the amount of lower-molecular weight compounds to be removed for PUFA purification. This idea is better illustrated as the contribution of individual FAME at each time step to the cumulative total oil up to that time (FIG. 15).

At the beginning extraction for the (26.7 MPa, 60-min) pretreated biomass, the difference between fractions for EPA and ARA versus the other compounds is the greatest. As extraction continues, the contributing amount of individual FAMEs to the total oil begins to decrease; however, the most drastic drop is seen for the saturated and lower-unsaturated components.

Figure 16:
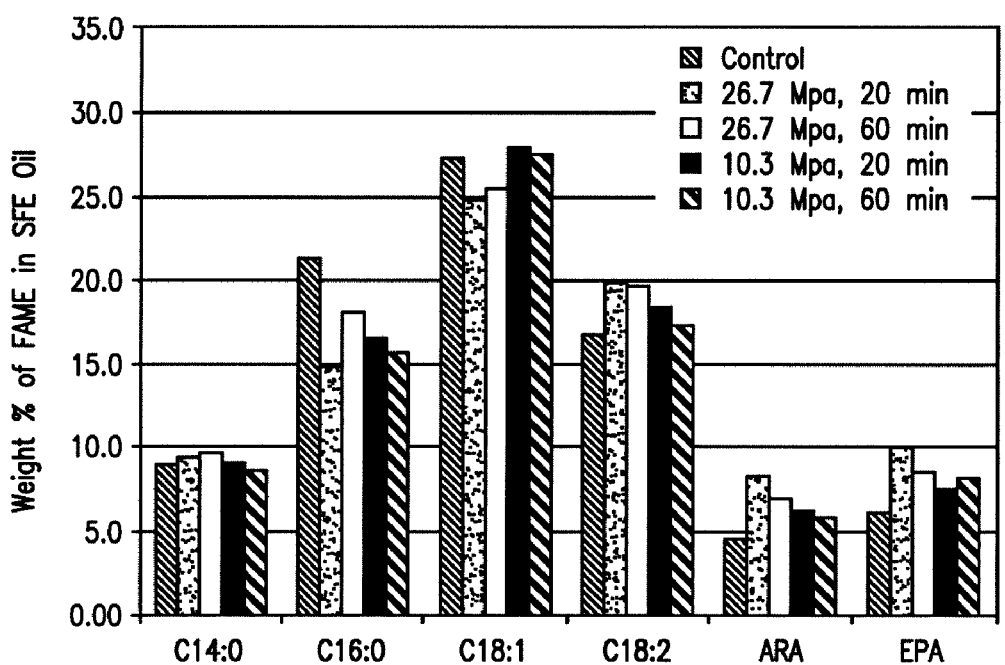
FIG. 16 compares FAME composition (wt %) obtained from extraction processes including $CO_2$-explosion and non-explosion pretreated biomass.

The oil collected over time was methylated and analyzed using gas chromatography to observe any changes in the oil's FAME composition between $CO_2$-explosion pretreatments and no explosion (SFE only). Quantification for the weight percent of individual compounds was done using the internal standard method. The FAME composition for a few select compounds, representative of the bulk composition, is shown in FIG. 16 for oil collected within 20 to 40 min.

In looking at 26.7 MPa treatments, FAME composition for the saturated and monounsaturated compounds did not appear to vary between soaking times. The (26.7 MPa, 20-min) treatment had a higher concentration of EPA and ARA compared to the (26.7 MPa, 60-min) treatment. Both of these treatments did seem to improve the concentration of the more unsaturated compounds, EPA, ARA, and linoleic acid (C18:2), over the control as well as the 10.3 MPa treatments. An increase of EPA and ARA wt % over the control is seen for the 10.3 MPa soaking pressure runs; however, the increase is not as large as the 26.7 MPa treatments. The (10.3 MPa, 60-min) and control runs had comparable wt % of the lower-molecular weight components, except for the saturated palmitic acid, which was the greatest of all runs tested at 21.3%.

The increase in PUFA composition with $CO_2$-explosion pretreatment can be attributed to the cellular storage of these highly unsaturated compounds. PUFAs are structural lipids found in the cellular wall to help maintain membrane fluidity; subsequently, they are produced at a higher rate by an organism when cultured at low temperatures. During the explosion process, the cellular walls are disrupted and the PUFAs are readily available for extraction. In addition, PUFAs like EPA may have a lower diffusivity through the cell walls when compared to the lower molecular weight compounds. With cellular disruption, the EPA is subjected to convective mass transfer, which is advantageous for obtaining more amount of EPA earlier in the extraction process.

Figure 17:
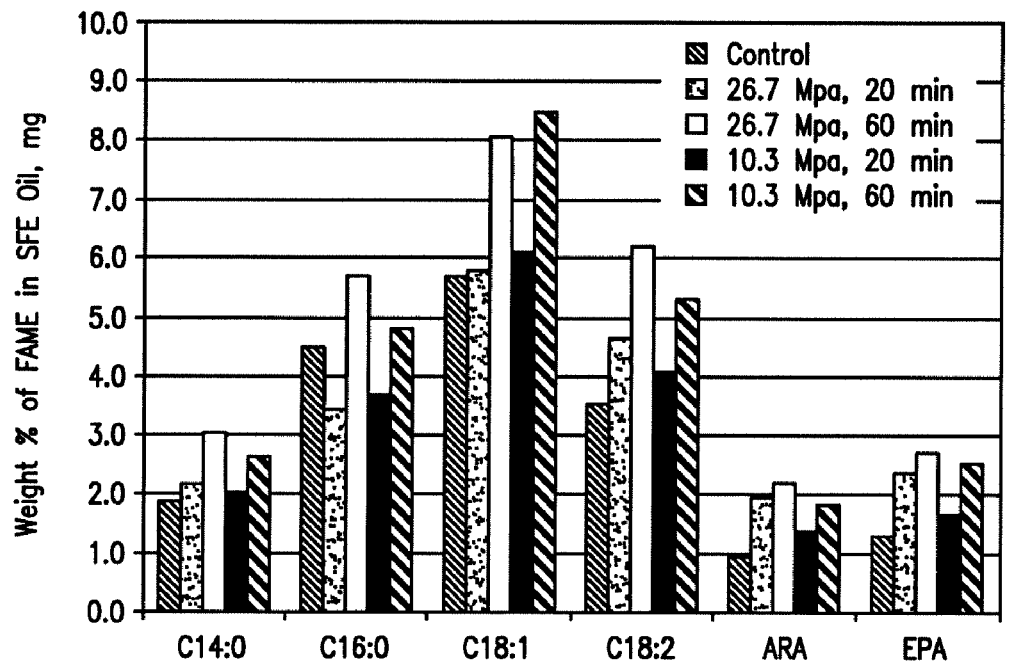
FIG. 17 compares weight of FAME (mg) obtained from extraction processes including $CO_2$-explosion and non-explosion pretreated biomass.

Even though large differences in the FAME composition of the oil were not observed between the extracted oils, large differences in the actual weight of FAMEs extracted during 20 to 40 min can be seen (FIG. 17). The actual weight of FAME takes into account the increase in yield seen in OECs (FIG. 7); therefore, both 60-min treatments would produce greater amounts of various components than the non-explosion treated biomass. The (26.7 MPa, 60-min) treatment more than doubled the original amount of EPA and ARA, 112 and 131% increase, respectively. The (10.3, 60-min) treatment increased EPA by 96% and ARA 89% over the control. An average 55% increase was seen for the C18 compounds for the 60-min treatments. The (10.3 MPa, 20 min) treatment had similar oil extraction yields as the control, and the only weight increases were noted for EPA and ARA. All other components had an actual decrease in the weight when compared to the control, The (26.7 MPa, 20-min) run yielded 83% more EPA and 105% more ARA when compared to the control runs.

Experiments were conducted to look at differences in HiP extracted oil from *P. irregulare* biomass that was only subjected to $CO_2$-explosion treatment. The $CO_2$ explosion process did increase the total extractable oil from the fungal biomass compared to the non-explosion treatment, which had a total oil weight of 135 mg. As seen in Table 7, the 20-min treatments did not improve total extractable oil as much as the 60-min treatments (p-value <0.033). The 20-min explosion treatments enhanced the total oil between 3 and 4%. The 60-min treatments improved the total extractable HiP oil between 10 and 17% compared to the non-explosion treatment. The (10.3 MPa, 60 min) explosion resulted in the largest enhancement with a 17% increase.

TABLE 7

| Soaking Pressure (MPa) | Soaking Time (min) | HiP Extractable Oil | Enhancement* (%) |
|---|---|---|---|
| 27.6 | 20 | 0.139 | 2.96 |
| 27.6 | 60 | 0.149 | 10.4 |
| 10.3 | 20 | 0.140 | 3.70 |
| 10.3 | 60 | 0.158 | 17.0 |

*=Enhancement is percentage increase from 0.135 mg of total oil extracted from non-$CO_2$-explosion treated biomass.

Figure 18:
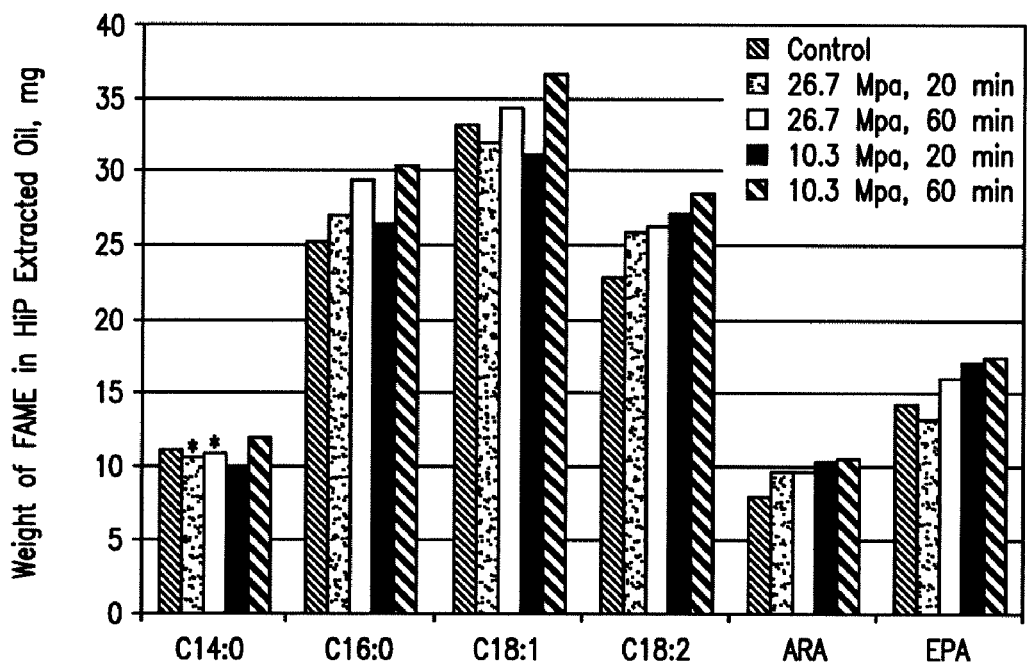
FIG. 18 illustrated the weight of FAME (mg) in hexane isopropanol (HiP) extracted *P. irregulare* oil obtained from $CO_2$-explosion only pretreated biomass.

Naturally, with an increase in total oil weight, one should see an increase in amount of individual FAMEs extracted. FIG. 18 shows the actual weight of six individual FAMEs. For all compounds except myristic acid (C14:0), $CO_2$-explosion pretreatment offered a statistically greater amount of FAME than the control (a-level=0.05). For the case of myristic acid (C14:0), a soaking pressure of 26.7 MPa offered no weight difference from the control. The amount of ARA extracted improved an average 28%, while improvements in EPA ranged between 13 to 22%.

Figure 19:
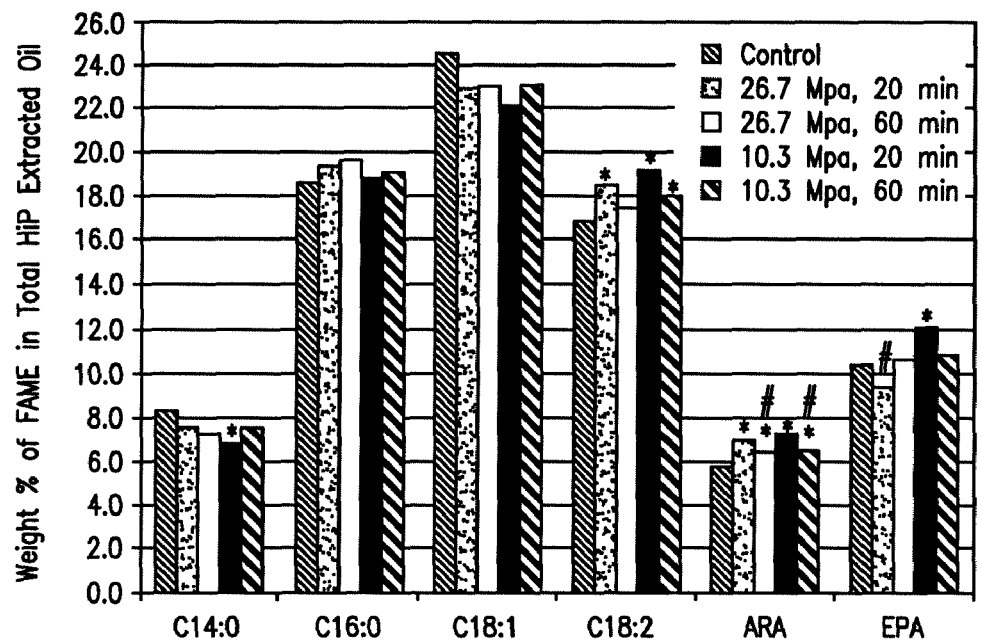
FIG. 19 illustrated FAME composition (wt %) of HiP extracted *P. irregulare* oil obtained from $CO_2$-explosion only treated biomass.

Even though the FAME weight was typically greater following pretreatment, few statistical differences were seen for the composition of the oils (FIG. 19). For the two saturated lower-weight FAMEs, the only significant difference existed for the (10.3 MPa, 20 min) treatment, which had a statistically lower composition of myristic acid compared to the control. No wt % differences were determined between treatments for oleic acid. As the degree of unsaturation increased, more differences were calculated between treatments and the control. Linoleic acid wt % for both 10.3 MPa and (27.6 MPa, 60-min) treatments were greater than the control but not different among explosion treatments. and within treatments (p-value <0.014). All $CO_2$-explosion pretreatments did statistically increase the ARA composition of the HiP oil from 5.76 wt % for the control up to 7.24 wt % for the (10.3 MPa, 20-min) pretreatment. Differences within treatments are seen when comparing (10.3 MPa, 20-min) to both 60-min treatments. The explosion process at (10.3 MPa, 20-min) did improve the EPA wt % of residual oil, 12.1 wt % compared to 10.4 wt %. The (26.7 MPa, 60-min) treatment had a lower EPA composition compared to the (10.3 MPa, 20-min) treatment.

Compared to SFE of non-explosion treated fungal biomass, $CO_2$-explosion pretreated biomass can provide a significant increase in extraction yield; for example, up to 22% more oil was obtained within 90 minutes of SFE. Longer soaking times prior to explosion can have a greater effect on SFE yield. $CO_2$-explosion techniques allowed for the constant extraction rate period to last longer than untreated biomass at the longer soaking times. Furthermore, decreasing the supercritical $CO_2$ density can improve the overall extraction yield by changing the diffusivity of the solvent.

Disclosed methods can be utilized to increase the overall SFE extraction yield of a PUFA-rich oil. Explosion pretreatment can double the amount of EPA and ARA extracted via SFE from the ruptured cells. $CO_2$-explosion as a pretreatment to organic solvent extractions can realize between a 20 to 30% increase in the amount of EPA and ARA.

Example 4

In this example, the change of pressure and phase within a high-pressure vessel during the $CO_2$ explosion process were investigated. Initial temperature and pressure conditions were chosen to encompass initial liquid, supercritical and gas phases. Canola flake was investigated as a biological model system for the effect on extractability of canola oil using supercritical carbon dioxide after the explosion pretreatment.

Figure 20:
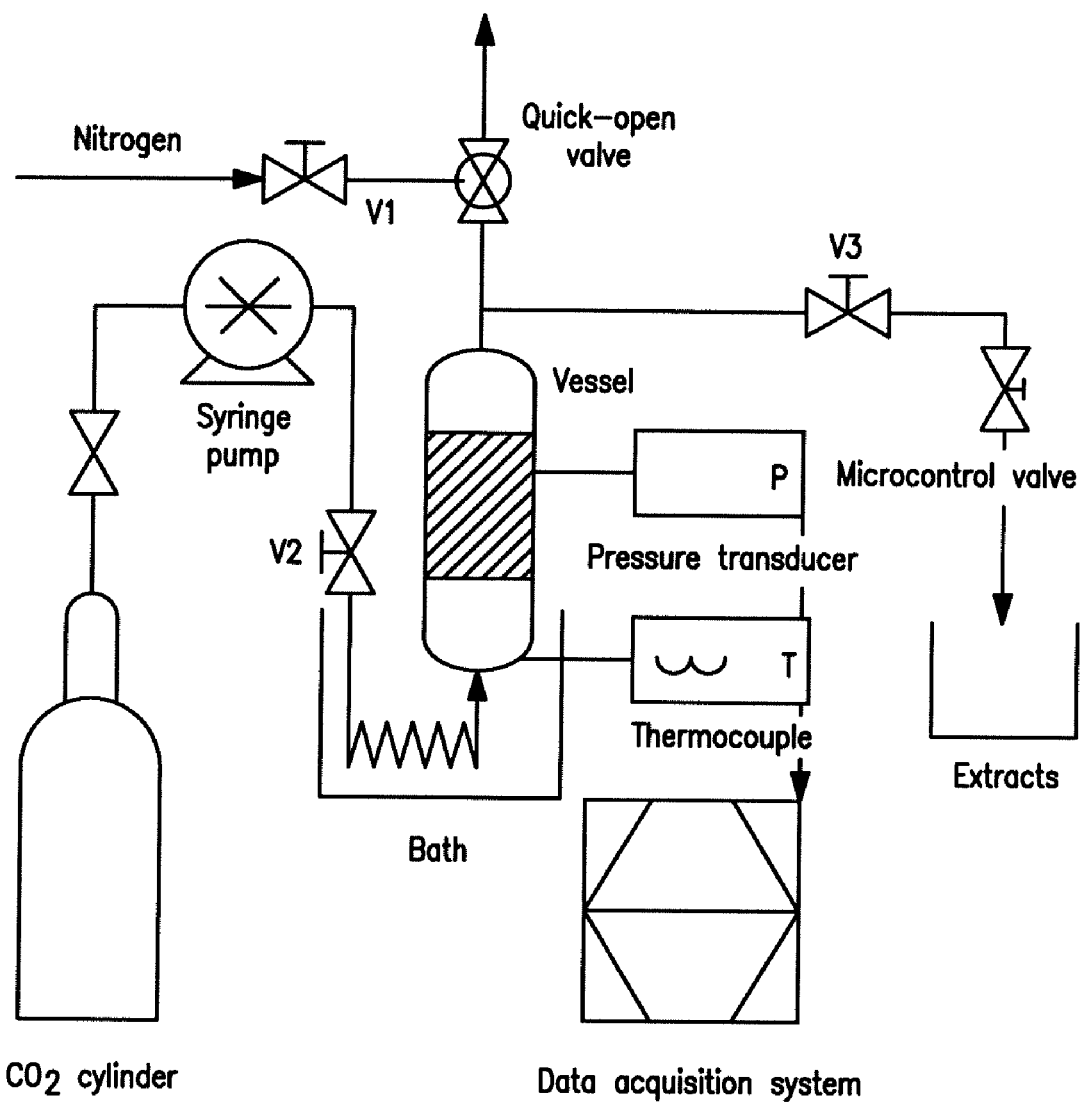
FIG. 20 is a schematic diagram of an explosion and extraction apparatus utilized in Example 4.

FIG. 20 illustrates the explosion apparatus, which consisted of five major components: syringe pump (ISCO, USA), high-pressure vessel (Thar Design, USA), quick-open ball-valve (Swagelok, SS-83KS4-31C, USA), temperature controlled water bath and data acquisition system. Omega flow meter (FMA-2305) was used to measure flow rate of effluent $CO_2$ gas at atmosphere conditions. This apparatus could be used for explosion, extraction or extraction following explosion. The system was set for explosion if keeping valve V3 closed and for extraction if kept open. The quick-open valve pneumatically actuated by 100 psi nitrogen gas was mounted to rapidly release the pressure inside the vessel.

Once all tubing connections were secured and the pneumatically actuated ball-valve was closed, the vessel was pressurized with $CO_2$ from the syringe pump until the experimental set pressure was achieved. Pressure was held for 30 min to allow $CO_2$ and sample (if for treatment of sample) to reach the set experimental temperature. The valve between the vessel and pump was then closed preventing gas exchange during the depressurization process. The data sampling frequency and duration were set with software. A rapid pressure release from saturation pressure to atmospheric pressure was imposed by opening the valve to activate the pneumatically actuated ball-valve using 100 psi nitrogen. Data were acquired at a sampling frequency of 500 Hz and duration of 10 seconds to characterize how the pressure decreased within the vessel.

A 75 mL vessel was coupled at both ends to evenly distribute the fluid and to prevent treated sample from exiting the vessel. Explosions were compared, with or without frit and with or without canola flake sample. The canola flake was donated from Archer Daniels Midland Company (ADM, USA). Canola flake was the product of raw canola seed after the processing of preheating, flaking and cooking in the crushing plant. 10 g of canola flake were loaded in the vessel for each run. Three tests were conducted, without frit and canola sample (Case A), with frit and without canola sample (Case B) and with frit and canola sample (Case C).

Explosions were carried out in each test, under 5 different initial temperatures, 25, 35, 45, 55, and 65° C., at the same initial pressure of 1500 psi. Explosions were also temperature of 35° C. The exploded canola flakes in Case C were stored at −5° C. for use of later supercritical $CO_2$ extraction.

Exploded canola flake for Case C was loaded into the vessel. The vessel was pressurized to 5000 psi, and the bath temperature was set to 50° C. After 30 min equilibration time, valve V3 and the micro-control valve were opened to produce a flow rate of approximately 700 mL/min for a total extraction of 7 hours. Unexploded canola flake was extracted under the same condition as the control. The extracted oil was trapped by glass beads in a 50 mL tarred centrifuge tube and weighed after each time interval.

For modified extraction, 10 g canola flake was extracted for 3 hours under the same extraction condition as above, then valve V3 was closed, and the flake was exploded by activating the quick-open valve under the same conditions as in Case C. After the quick-open valve was closed, the same extraction pressure of 5000 psi, temperature of 50° C. and flow rate of 7000 mL/min were then set for another 3 h extraction.

Extracted oil was converted to fatty acid methyl esters (FAMEs) using a base-catalyzed transmethylation procedure as described above. Fatty acids were quantified by incorporating a known amount of internal standard, heptadecanoic acid methyl ester (C17:0) (Nu-check prep Inc, USA) into each sample after methylation. Fisher Chemicals provided all reagents in this work unless otherwise noted.

Figure 21A:
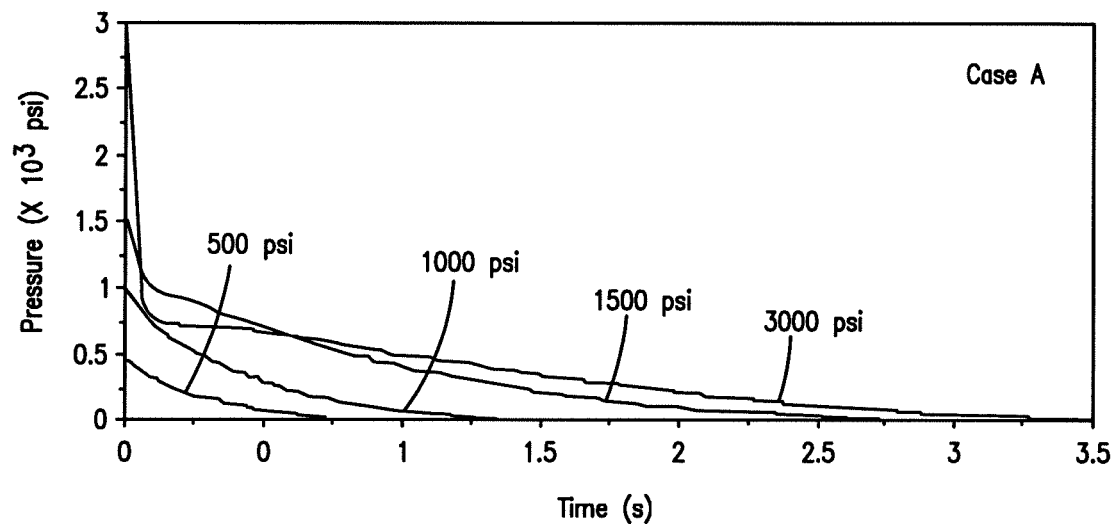
FIG. 21 illustrates a pressure/time trace of $CO_2$ subjected to different pressures for different example cases; without frit in place and with canola sample (Case A, FIG. 21A), with frit in place and without canola sample (Case B, FIG. 21B), with frit in place and with canola sample (Case C, FIG. 21C)
Figure 21B:
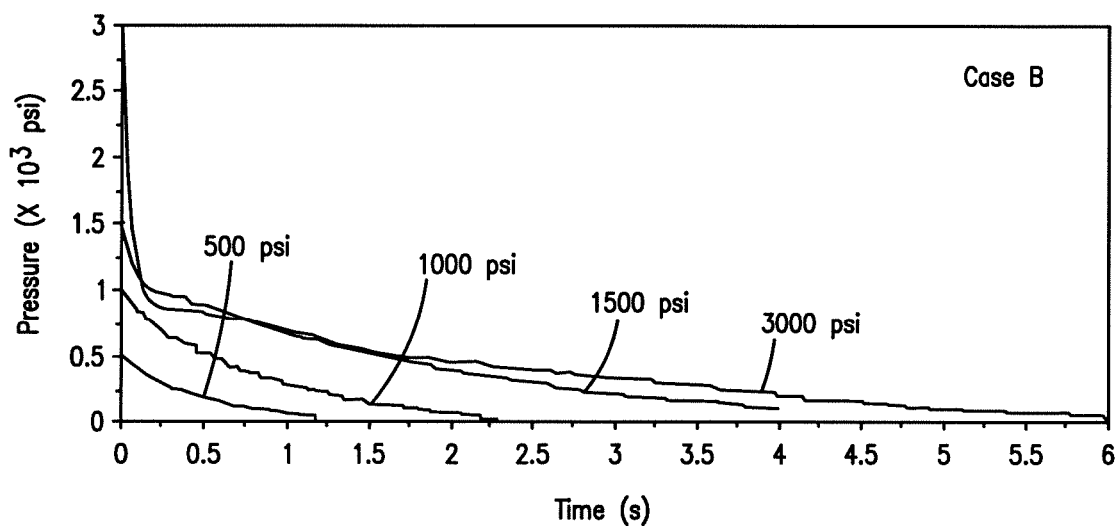
Figure 21C:
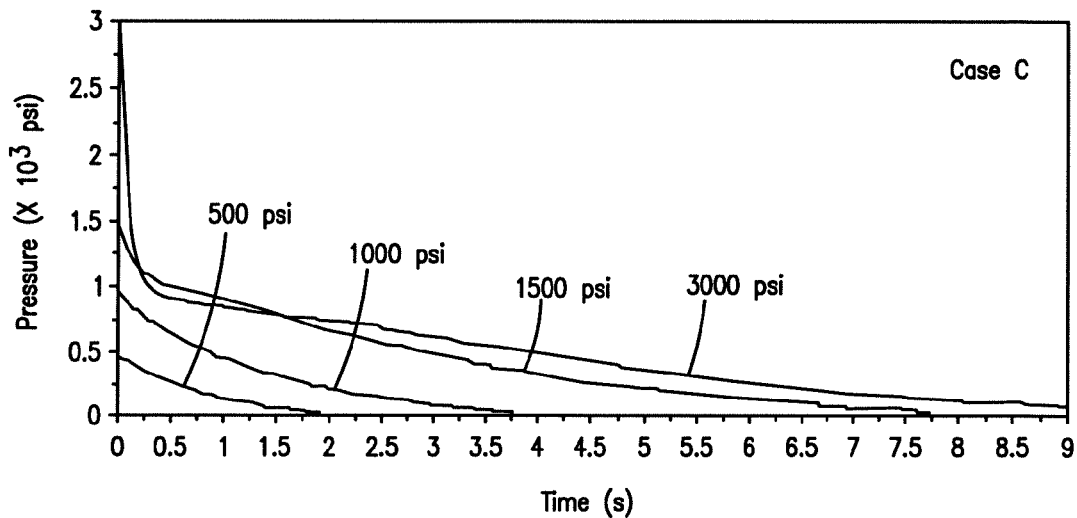

The pressure-time curves for different initial pressures at 35° C. are shown in FIGS. 21A-21C. Similar trends for cases A, B and C were observed. At initial pressures of 500 and 1000 psi, the $CO_2$ was gaseous in the sub-critical phase. The depressurization curves are smooth, where the pressure decreased gradually within a short time of several seconds. At initial pressures of 1500 and 3000 psi, the $CO_2$ was in super-critical phase.

The depressurization curves have two obvious sections, where pressure decreased quickly in the first section and less so in the later section. The point of rapid transition or abrupt break in the curve was determined by the inflection point or maximum rate of change of depressurization rate. The data of total depressurization time, the pressure and time corresponding to the point of abrupt break are shown in Table 8, below. The fit increased the depressurization time for Case B compared to Case A. For Case C, 10 g canola flake samples filled 25 mL of the total 75 mL vessel, and decreased the depressurization time due to reduced $CO_2$ volume. On the other hand, canola flake sample elongated the depressurization time due to its resistance. As a result, Case C had the longest pressure release time compared to Case A and Case B. The longest time was 9.620 s for case C at 3000 psi and the shortest total depressurization time was 0.728 s for case A at 500 psi.

TABLE 8

| Initial Pressure (psi) | Total Time (sec) | | | Phase change time (sec) | | | Phase change pressure (psi) | | |
|---|---|---|---|---|---|---|---|---|---|
| | A | B | C | A | B | C | A | B | C |
| 500 | 0.728 | 1.182 | 1.908 | No abrupt change | | | No abrupt change | | |
| 1000 | 1.328 | 2.203 | 3.748 | | | | | | |
| 1500 | 2.728 | 4.078 | 7.730 | 0.150 | 0.247 | 0.476 | 949 | 969 | 1000 |
| 3000 | 3.502 | 5.999 | 9.620 | 0.090 | 0.184 | 0.361 | 818 | 909 | 970 |

Figure 22A:
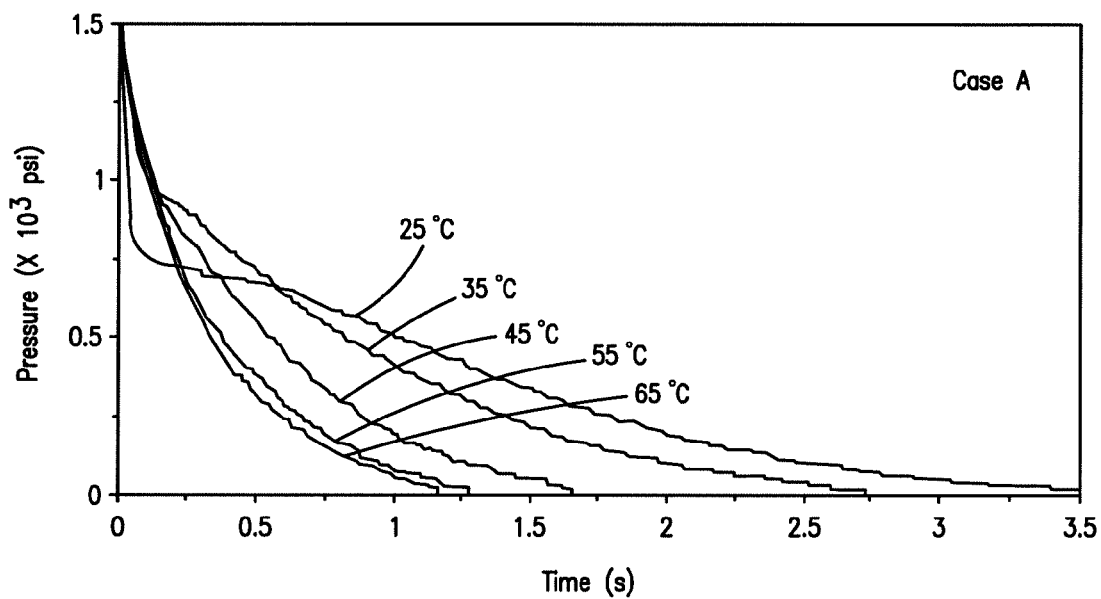
FIG. 22 illustrates a pressure/time trace of $CO_2$ subjected to different temperatures for different example cases; without frit in place and with canola sample (Case A, FIG. 22A), with frit in place and without canola sample (Case B, FIG. 22B), with frit in place and with canola sample (Case C, FIG. 22C)
Figure 22B:
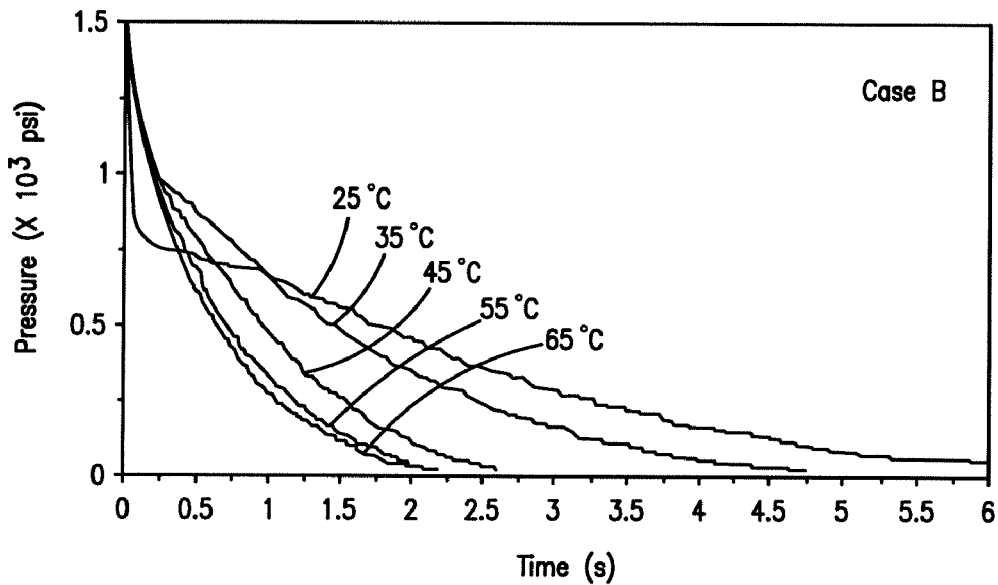
Figure 22C:
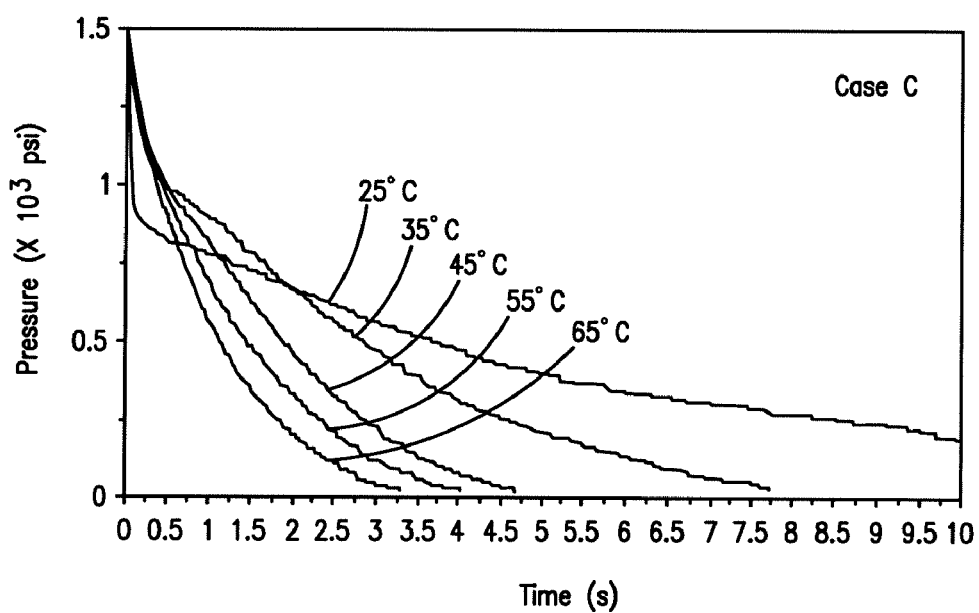

The pressure-time curves under different temperatures at 1500 psi of initial pressure are shown in FIGS. 22A-22C. Similar trends for cases A, B and C were also observed. At initial temperatures of 55° C. and 65° C., the depressurization curve was smooth. At initial temperatures of 25° C. and 35° C., the depressurization curves again contained two distinctive sections. At an initial temperature of 45° C., the depressurization curve transitioned without a distinctive break. The data of total depressurization time, the pressure and time corresponding to the point of abrupt break are shown in Table 9. The total depressurization time decreased with an increase of initial temperature in each case. This result was consistent with the viscosity behavior of supercritical fluids, which decreased with increasing temperature at the same pressure. Therefore, the fluids with lower viscosity depressurized more quickly. The frit and canola flake filling showed a similar effect on total depressurization time for each initial temperature. The longest depressurization time was >10 sec for Case C at 25° C. and the shortest time was 1.168 sec for Case A at 65° C.

TABLE 9

| Initial Temperature (° C.) | Total Time (sec) | | | Phase change time (sec) | | | Phase change pressure (psi) | | |
|---|---|---|---|---|---|---|---|---|---|
| | A | B | C | A | B | C | A | B | C |
| 25 | 3.506 | 6.932 | <10 | 0.074 | 0.082 | 0.206 | 797 | 838 | 878 |
| 35 | 2.728 | 4.078 | 7.730 | 0.150 | 0.247 | 0.456 | 949 | 969 | 1000 |
| 45 | 1.658 | 2.610 | 4.608 | 0.182 | 0.318 | 0.536 | 909 | 919 | 980 |
| 55 | 1.282 | 2.226 | 4.018 | No abrupt change | | | No abrupt change | | |
| 65 | 1.168 | 2.122 | 3.300 | | | | | | |

The rate of depressurization, $\Delta P/\Delta t$, computed by corresponding data in Tables 8 and 9, is shown in Tables 10 and 11, respectively. The rate of depressurization increased with the increase of initial pressure or temperature within each case. At each initial condition, the rate of depressurization decreases following Cases A, B and C. Again worthy of interest was the situation in which two-stage depressurization occurred. The total rate of depressurization was reduced at lower initial temperature in each case. The rates of depressurizations had two stages for the rapid and lag depressurization, compared to the smooth decompression. For example, for Case C in Table 10, the depressurization rate of rapid depressurization section of the curve was 5,577 psi/s and 104 psi/s for lag section at 3,000 psi initial pressure, compared to 267 psi/s of total depressurization rate for the initial pressure of 1,000 psi. This two-stage depressurization may affect the exploded sample differently depending on its variety and physical properties.

TABLE 10

| Initial Pressure | Rate of Depressurization (psi/s) | | |
|---|---|---|---|
| (psi) | A | B | C |
| 500 | 687 | 423 | 262 |
| 1000 | 753 | 454 | 267 |
| 1500 | 550 | 368 | 194 |
|  | [3693] | [2150] | [1050] |
|  | (368) | (252) | (137) |
| 3000 | 857 | 500 | 312 |
|  | [24244] | [11364] | [5577] |
|  | (240) | (156) | (104) |

TABLE 11

| Initial Temperature | Rate of Depressurization (psi/s) | | |
|---|---|---|---|
| (° C.) | A | B | C |
| 25 | 482 | 216 | <150 |
|  | [9500] | [8073] | [3019] |
|  | (232) | (122) | (<90) |
| 35 | 550 | 368 | 194 |
|  | [3673] | [2150] | [1096] |
|  | (368) | (253) | (137) |
| 45 | 905 | 575 | 326 |
|  | [3247] | [1827] | [970] |
|  | (615) | (401) | (241) |
| 55 | 1170 | 674 | 373 |
| 65 | 1284 | 707 | 455 |

Figure 23A:
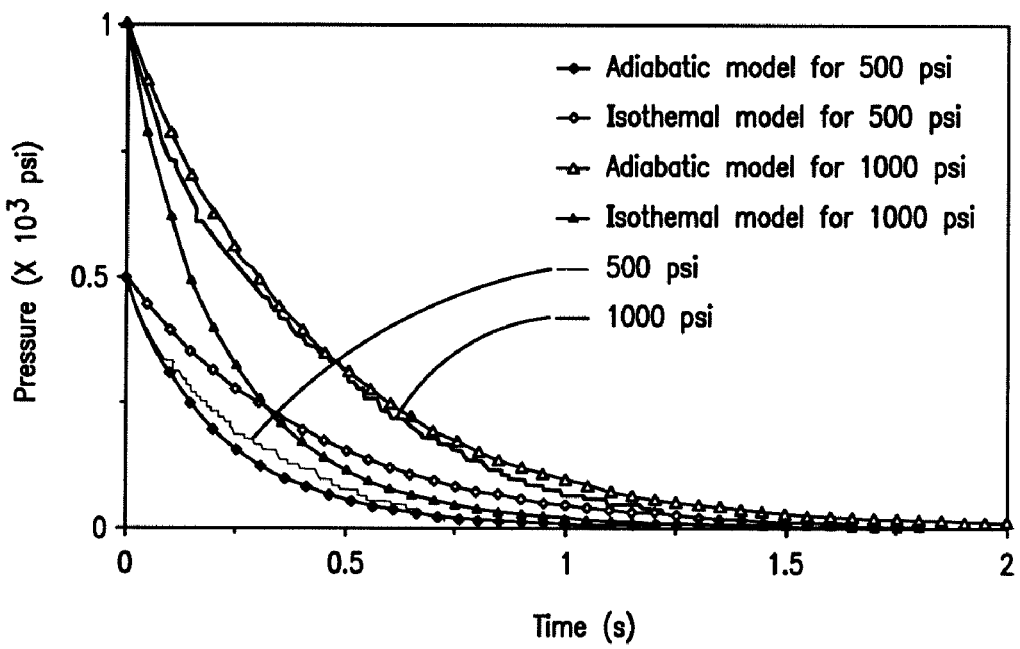
FIG. 23A compares the theoretical and experimental curves of an explosion process with frit in place and without canola flake.
Figure 23B:
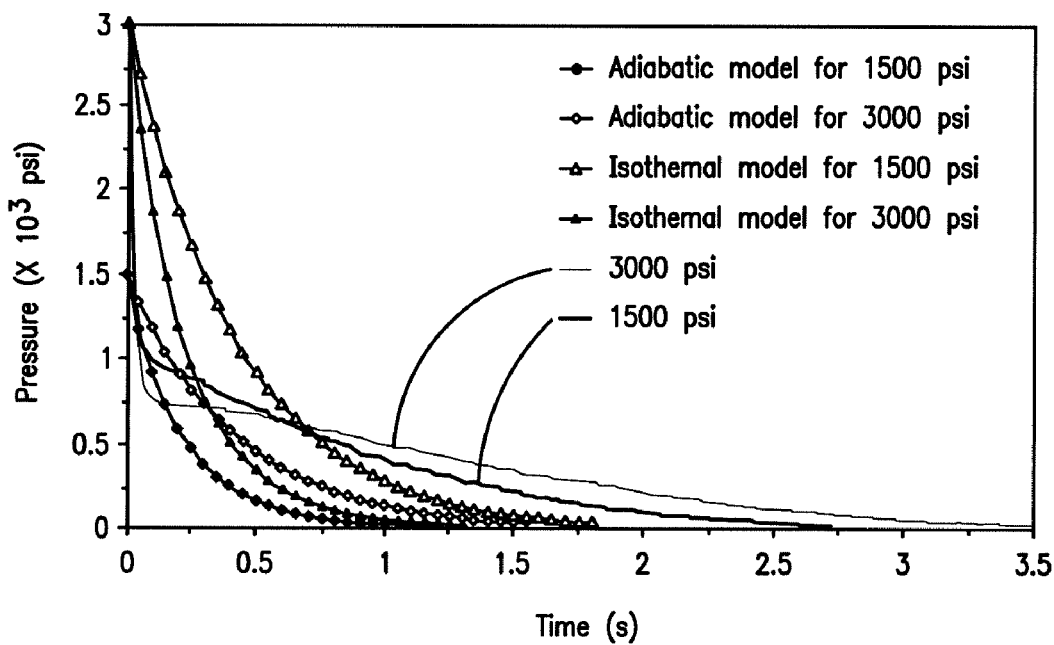
FIG. 23B compares the theoretical and experimental curves of an explosion process.

The experimental results were found to be between the adiabatic and isothermal theoretical results (see FIG. 23A). For 500 psi initial pressure, the data fit well with the adiabatic theoretical results. Significant heat transfer does not occur during the 1 sec of discharge. For 1,000 psi initial pressure, the data is better represented by the isothermal assumption. Heat transfer is more significant during the 2 sec of discharge. For the 1,500 and 3,000 psi initial pressures, the experimental results are not between the theoretical results of adiabatic and isothermal models (see FIG. 23B). At these initial conditions $CO_2$ exhibits both gas and liquid behavior, and the theoretical models based on ideal gas assumption are no longer suitable. In addition, the experimental results have obviously two-stage decompression crossing the region of liquid/gas saturation curve.

Figure 24:
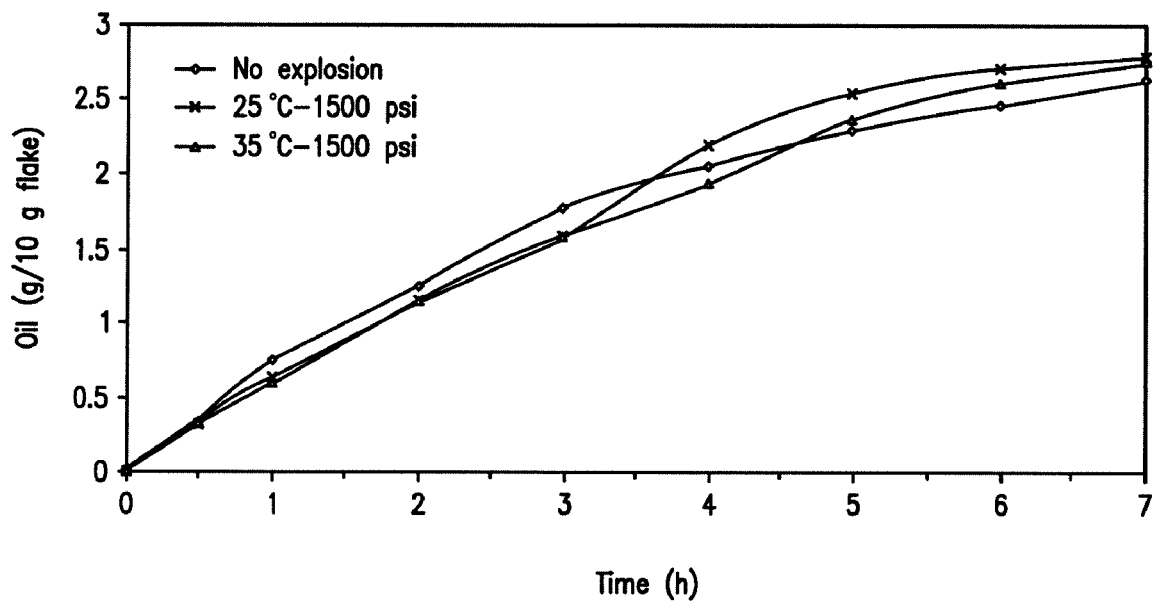
FIG. 24 illustrates the cumulative extraction curve following an explosion process as described herein.

The total oil obtained from 10 g canola flake was 4.17 g determined by overnight Soxhlet extraction using hexane. The cumulative curve of supercritical $CO_2$ extraction had convective-controlled, transition, and diffusion-controlled extraction rate periods (FIG. 24). For the unexploded canola flake, the constant extraction rate period, defined by the linear equilibrium relationship between solute and solvent, occurred during the first 3 h until about 43% of the available oil was removed. After this period, the extraction rate slowly decreased and eventually entered into a diffusion-controlled period after 7 h when almost 63% of the oil was extracted.

For the exploded canola flake, the extraction curve was lower than that of unexploded canola flake during the first 3 h extraction, but the extraction curve for the exploded canola flake was higher than that of unexploded canola flake during the later 4 h extraction. The explosion process extended the constant extraction rate period and improved diffusive extraction of oil, resulting in more extracted oil. The canola flake from a commercial crushing plant was processed with preheating, flaking and cooking. To some extent, the cell wall of canola seed may have been disrupted and the minute lipid particles coalesced to form large oil droplets, partially moving onto the surface. The ruptured oil was easily extracted during the constant extraction rate period. However, the explosion process may have affected this coalesced oil in this experiment, which may explain the phenomena of the lower oil extraction during the first 3 h after explosion treatment. One possibility was due to the effect of oil loss in the explosion process. The oil dissolved in $CO_2$ at different initial explosion conditions was released with the high-pressure $CO_2$. For example, at 35° C. and 1,500 psi, the oil solubility of canola oil was about 0.5 mg/g $CO_2$ and the density of $CO_2$ was 0.65 g/cm$^3$. An estimated 16 mg oil can be released during the explosion process in this experiment. Another possibility is that the explosion process broke the coalesced oil droplets and disrupted the mixture of oil and substrate, making this normally easily extracted oil more difficult to extract if oil was first absorbed back into the substrate. The reduced oil extraction rate in the first 3 h may result in more oil extracted in the following 4 h, which could hide both of positive or negative effect of explosion on extractability.

Figure 25:
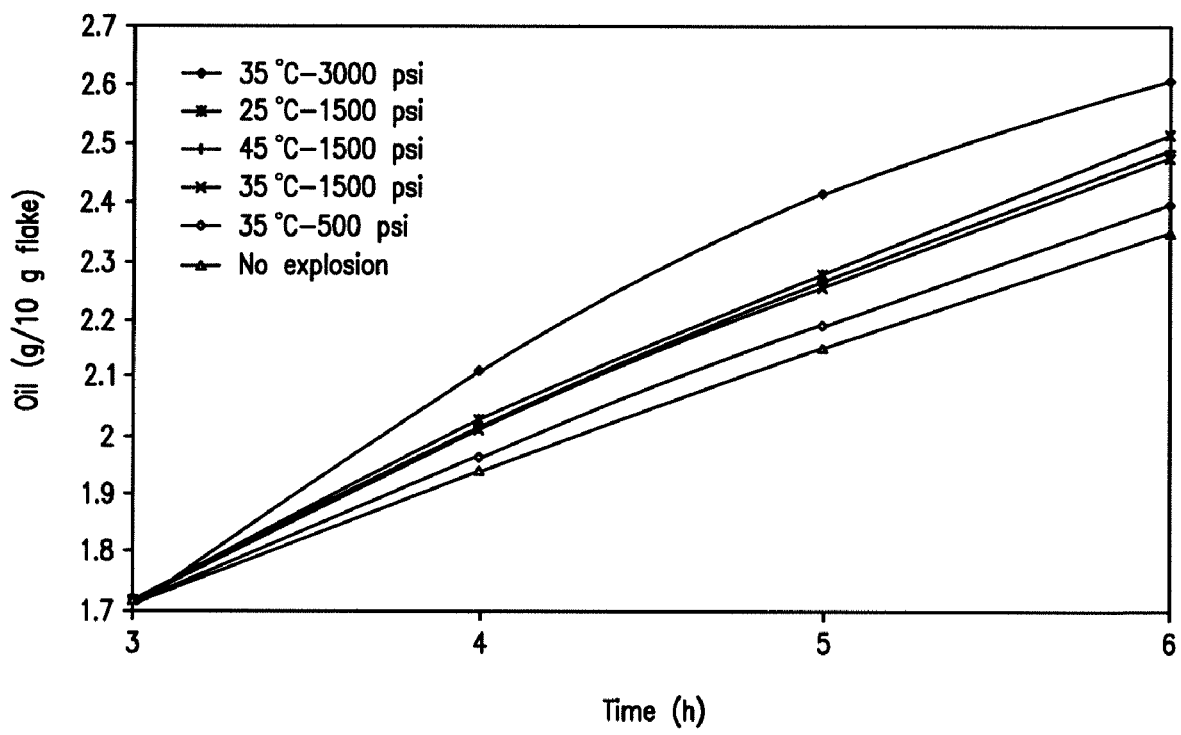
FIG. 25 illustrates a cumulative extraction curve following an extraction and explosion process.

To minimize the effect of oil loss and the disruption of the coalesced oil from explosion, the process was integrated after the surface oil was extracted in the first 3 h and followed another 3 h of extraction. The explosion process was expected to improve diffusive-controlled extraction. The cumulative extraction curve for the later 3 h is shown in FIG. 25. The least significant difference test (LSD) of multiple comparisons was done at the 95% level for each initial explosion process (SAS Ver. 9.1, SAS Institute Inc., Cary, N.C.). The results showed that all explosion processes improved the oil extractability with higher yields during the later 3 h extraction, except for the 500 psi initial pressure at 35° C. condition, most likely due to low initial pressure. At a pressure of 1,500 psi, extraction at temperatures of 25, 35 and 45° C. did not result in significantly different yields. However, a higher yield was observed at 25° C. compared to 35 and 45° C. This interesting result might show the cryogenic effect was more pronounced than a penetration-improved effect of higher temperature of 45° C. At the temperature of 35° C., increasing pressures of 500, 1,500 and 3,000 psi resulted in the significantly higher oil yields. The highest yield was achieved at initial condition of 35° C. and 3,000 psi.

Figure 26:
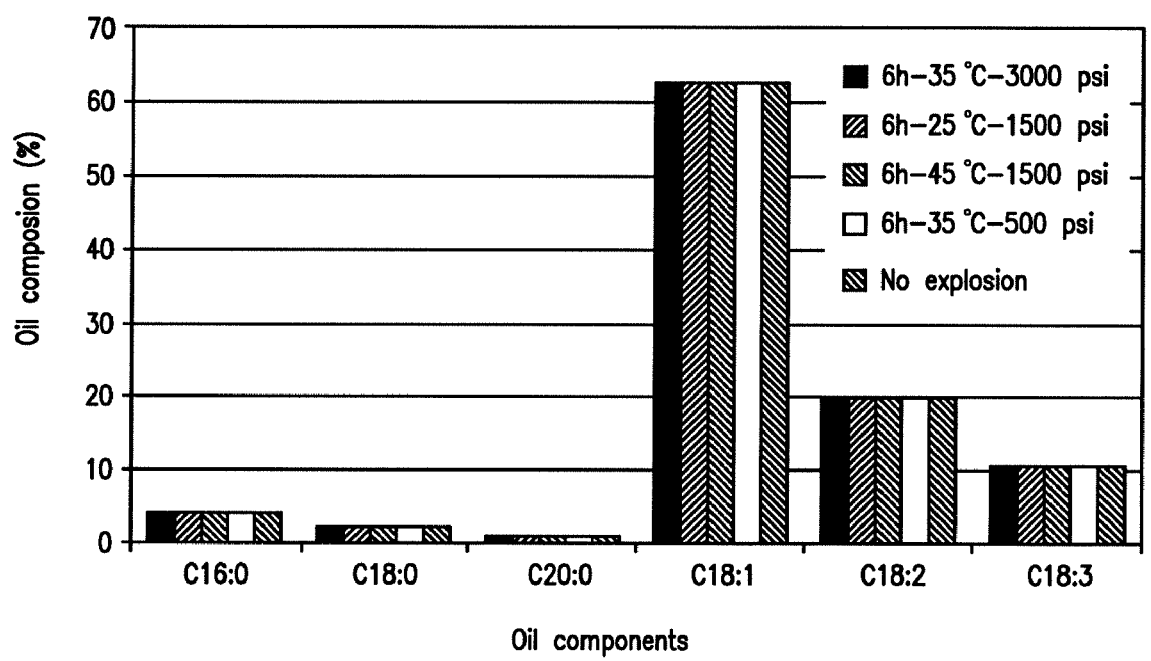
FIG. 26 illustrates the oil composition extracted over three hours following explosion processes at various conditions.

The results for the effect of temperature and pressure might be interpreted from other multiple factors. The canola flake is a very oily material and should have its own explosion characteristics compared to other non- or low-oil materials. The oil composition for the percentages of the main components, C16:0, C18:0, C20:0, C18:1, C18:2 and C18:3 is shown in FIG. 26. The statistics results of Dunnett's test at 95% confidence by SAS showed no significant difference compared to oil extracted from unexploded flake.

Example 5

1.5 g of canola flake and 1.5 g of canola cake were each separately used as a substrate for a culture of *M. alpina* to examine the accumulation of plant PUFAs in the fungal culture following fermentation. The canola materials were utilized as both the carbon and nitrogen sources for the culture.

*M. alpina* (ATCC32222) was maintained on potato dextrose agar (PDA) plates and transferred every three weeks.

Canola materials were donated by Archer Daniels Midland Company (ADM, USA). The canola flake had an oil content of 41% (w/w) and the canola cake had an oil content of 16% (w/w).

Submerged culture was conducted in 250 mL flasks in a refrigerated incubator shaker (New Brunswick Scientific, USA). The inoculation preparation included inoculating 1 cm2 of culture grown on PDA plate to 50 mL media including 1.5 g glucose and 0.25 g yeast extract, and shaking at 25° C. and 150 rpm for two days. A two-day cultivated pellet was homogenized with a Polytron homogenizer (PT 1200 model, KINEMATICA, Switzerland) for 10 s at the highest rpm setting, and then 2.5 mL (5% v/v) mycelial suspension was inoculated to 47.5 mL media and incubated at 20° C. and 150 rpm for 7 days. The media pH was about 6.3 without adjustment before autoclaving at 121° C. and 15 min. As control, a culture using the media was used.

Following culture period, fungal cells together with substrate residuals were harvested by suction filtration and washed with distilled water. The wet biomass was dried in a 70° C. oven overnight. The dried biomass was extracted in a 50 mL centrifuge tube using 20 mL hexane, homogenized with a Polytron homogenizer (PT 1200 model, KINEMATICA, Switzerland) for 5 min, kept in a water bath at 55° C. for 10 min and centrifuged at 3,000 rpm for 10 min. Supernatant was transferred to another tarred centrifuge tube. The extraction was repeated twice using 5 mL hexane, and supernatants were combined and evaporated using a vacuum centrifugal evaporator (Savant instruments Inc., USA). The dried biomass and evaporated lipids were measured by analytical balance.

Extracted lipids were converted to fatty acid methyl esters (FAMEs) using a rapid transmethylation procedure.

Figure 27A:
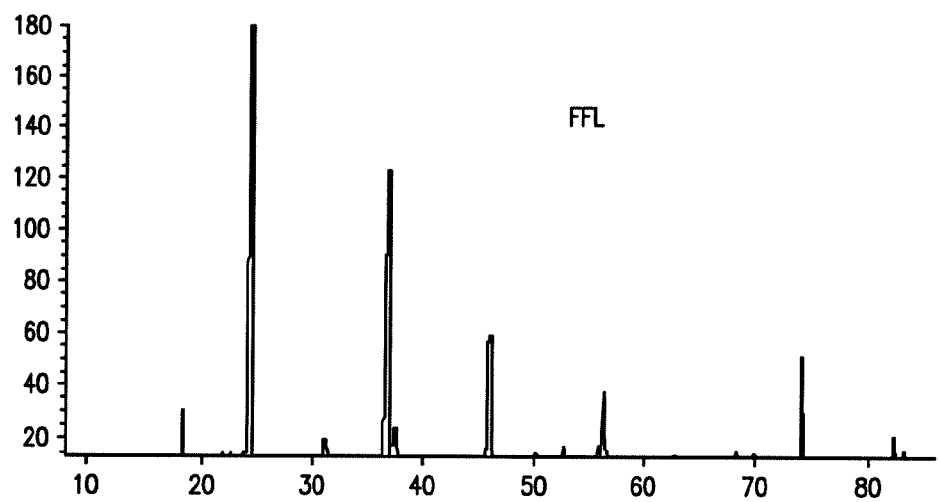
FIG. 27A illustrates lipid profile produced in a fungal culture using canola flake substrate.
Figure 27B:
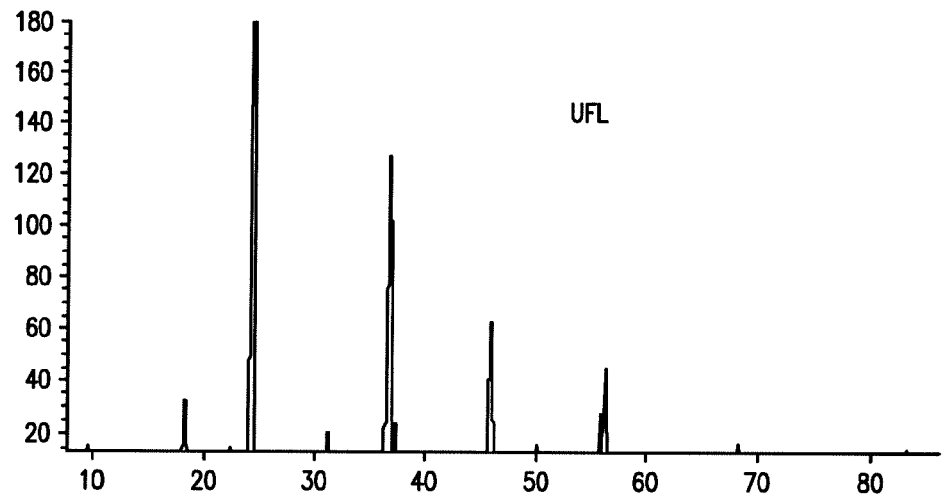
FIG. 27B illustrates the lipid profile of unfermented canola flake.
Figure 27C:
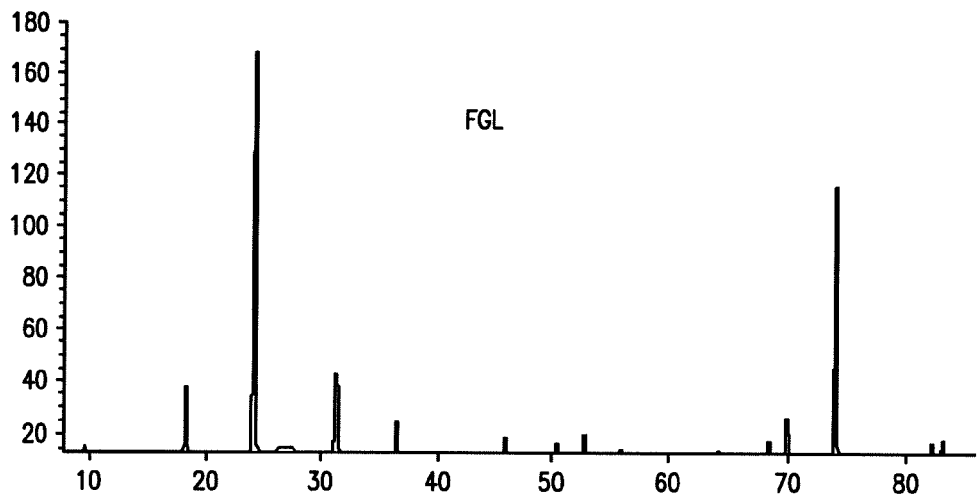
FIG. 27C illustrates the lipid profile produced in a fungal culture using glucose and yeast extract substrate.

The separation of the fungal biomass from the residual substrate was not feasible, so the extracted lipids consisted of the residual lipids in the substrates and those produced by fungi. At the detectable level of >1 µg/mL in the present method, the profiles of the lipids produced by fermentation using different substrates are shown in FIG. 27 (FFL-lipids produced by fermentation using canola flake; FCL-lipids produced by fermentation using canola cake; FGL-lipids produced by fermentation using glucose and yeast extracts; and UFL-lipids extracted from the unfermented (raw) canola flake). The components of FFL and FCL were nearly identical (the profile of FCL is not shown). The results showed that four components were new in the profile of FFL compared to UFL. These four components consisted of trans C16:1, γ18:3n6, C20:4 (ARA) and C20:5 (EPA).

Figure 28:
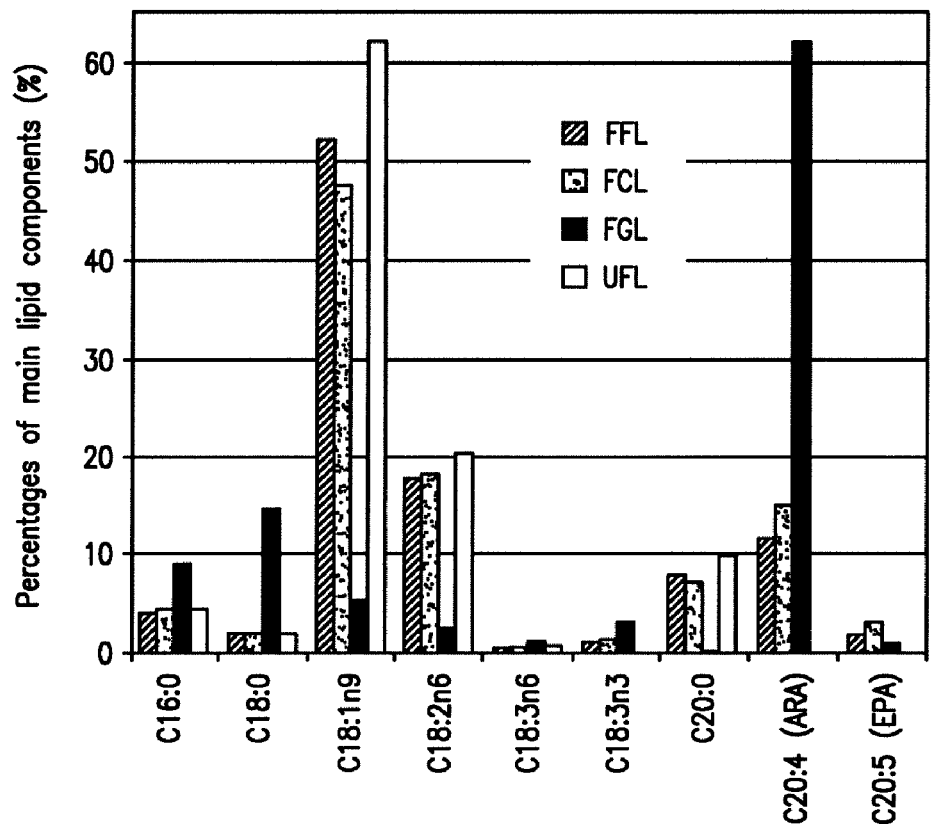
FIG. 28 illustrates the lipid compositions obtained in fungal cultures developed on different substrates including canola flake, canola cake, glucose and yeast extract, and the lipids extracted from unfermented canola flake.

One new component, trans C16:1, emerged in FFL, which neither FGL nor UFL contained. Overall, three new PUFAs, γ18:3n6, C20:4 (ARA) and C20:5 (EPA), were added through fungal culture. FIG. 28 shows the percentages of main components of each lipid. The profile of FFL was extended to the fatty acids with longer chain and higher polyunsaturation compared to the UFL. The ratio of polyunsaturated to saturated fatty acid (P/S) increased from 4.0 for UFL to 6.2 for FFL. The FGL had the highest ARA percentage of 63%, compared to 12% of FFL. However the P/S was as low as 2.8 due to the high saturated fatty acid content of 25% of total lipids. FFL had slightly lower saturated fatty acid content of 6.6% compared to 7.5% of UFL. The FCL had a similar profile to the FFL, with 6.3 of P/S ratio and ARA of 15.1%.

The FFL exhibited complete and balanced lipid constitutes, with a low level of saturated fatty acids, a relatively high level of monounsaturated fatty acids, and PUFAs.

Example 6

A mixed culture was conducted by *Mortierella alpina* co-cultivated with *Pythium irregulare* using the same substrate and methods as in Experiment 5. Each of 1.25 ml mycelial suspension was inoculated, making a total of 2.5 ml (5% v/v) for inoculation. The separate culture was conducted with 2.5 ml (5% v/v) inoculation of single strain, *Mortierella alpina* and *Pythium irregulare* using the same substrates as for mixed culture.

Separately, the fungus *Pythium irregulare* produces more EPA than ARA, and *Mortierella alpina* produced higher ARA than EPA. Table 12, below, shows the results of production of PUFAs and lipid compositions (%). Values are the means of duplicate methods.

TABLE 12

| PUFA | Symbol | Canola | | Soybean | Corn | Olive |
| | | SFE | Hexane | | | |
| --- | --- | --- | --- | --- | --- | --- |
| Myristic | C14:0 | 0.1 | 0.1 | 0.4 | 0.3 | 0.2 |
| Palmitic | C16:0 | 4.3 | 4.8 | 10.7 | 10.5 | 11.1 |
| Stearic | C18:0 | 2.2 | 2.1 | 4.8 | 2.0 | 3.7 |
| Oleic | C18:1n9 | 62.5 | 61.5 | 23.0 | 28.9 | 77.7 |
| Linoleic | C18:2n6 | 20.5 | 21.1 | 53.6 | 56.8 | 6.2 |
| Arachidic | C20:0 | 0.8 | 0.7 | 0.4 | 0.4 | 0.4 |
| γ-Linolenic | C18:3n6 | 0 | 0 | 0.3 | 0 | 0 |
| α-Linolenic | C18:3n3 | 9.7 | 9.7 | 6.9 | 1.1 | 0.7 |

SFE - super critical fluid extraction;
Hexane - hexane extraction

The results indicated that *Pythium irregulare* had lower ability than *Mortierella alpina* to produce PUFAs using canola substrate at present culture conditions. When canola flake was used as substrate, single culture of *Mortierella alpina* produced equal ARA and higher EPA production compared to using glucose as substrate. Single culture of *Pythium irregulare* yielded lower ARA and EPA compared to using glucose as substrate, so the lipid profile was not significantly modified compared to the initial canola oil, with only a small addition of PUFAs, 0.6% of ARA and 1.0% of EPA. When canola cake was used as substrate, *Mortierella alpina* also produced higher PUFAs than *Pythium irregulare*. Interestingly, the mixed culture produced higher lipids than pure culture. The ARA production in mixed culture was greater than the sum of two single cultures. This indicated that *Pythium irregulare* possibly promoted the growth of *Mortierella alpina* with higher ARA and EPA yields.

The lipid profiles from the separate cultures of two strains were quite different. However, the profile from the mixed culture was much like the lipid profile of *Mortierella alpina* compared to *Pythium irregulare*. The ARA yield increased 88% from 20 mg/g glucose for *Mortierella alpina* culture to 38 mg/g glucose in mixed culture. When canola flake and cake were used, the ARA yield increased 30% and 83%, respectively, and the EPA yield increased 30% and 37%, respectively. As a result, the mixed culture achieved the highest ARA yield of 26 mg/g flake, 23 mg/g cake and 38 mg/g glucose, and had favorable lipid profile with P/S of 6.5 and 8.7 for flake and cake, respectively. The yield of ARA using glucose was higher than using flake and cake, while the EPA yield was lower.

According to previous studies, the maximum ARA production of *Mortierella alpina* was obtained at 20° C., while maximum EPA production of *Pythium irregulare* was obtained at a lower temperature of 12° C. The optimal culture time for maximum PUFA production is known to be different between these two strains. In this experiment, the cultures were conducted based on the optimal conditions for culture of *Mortierella alpina*. Unfavorable culture conditions is believed to explain the lower production of EPA from *Pythium irregulare*, either in single or mixed culture.

Example 7

On the basis of 40% oil content of 1.5 g canola flake, 0.6 g of soybean, corn (Southern Home®) and olive oil (Sempre Extra Virgin®) oil were combined with 0.9 g canola meal (<1% w/w oil content) and were used as substrate for the culture of *Mortierella alpina*. The culture of 0.9 g oil-freed flake and 0.6 g canola oil as substrate was conducted for comparison. Oil-freed flake was prepared after overnight soxhlet extraction of oily flake.

Among the oils, canola oil has higher level of oleic acid and mid-range level of linoleic acid; soybean and corn oil have similar profiles with a higher level of linoleic acid and a midrange level of oleic acid; while olive oil contains the highest oleic acid level. Only soybean oil contained γ-linolenic acid (0.3%). Table 13, below, shows the results of modified lipid compositions and the production of PUFAs. Values obtained are the means of duplicate runs.

TABLE 13

|  | Flake | Oil-freed flake + canola oil | Meal + canola oil | Meal + soybean oil | Meal + corn oil | Meal + olive oil |
|---|---|---|---|---|---|---|
| Dry Biomass (mg) | 1156 | 1212 | 1133 | 1156 | 1165 | 1153 |
| Total lipids (mg) | 437.4 | 405.6 | 371.2 | 404.6 | 385.6 | 402.9 |
| C20:4 (ARA) | 25.9 | 33.2 | 41.7 | 39.7 | 47.3 | 48.9 |
| C20:5 (EPA) | 3.9 | 4.9 | 5.7 | 3.4 | 1.1 | 1.2 |
| ARA/EPA | 6.6 | 6.8 | 7.3 | 11.7 | 43.0 | 40.8 |

The results show that canola meal plus canola oil yielded the highest ARA and EPA; freed flake plus canola oil produced the second highest yields; and the yields when directly using oily flake as substrate were the lowest. These results are believed to indicate that: (a) the freed oil was more accessible compared to that contained in the flake matrix; (b) the meal was more digestible than flake after being extruded and distilled during oil processing; and (c) the oil-free flake was more digestible as the nitrogen source than oily flake because of its porous structure after the oil was extracted.

For the different oils and canola meal used as substrate, corn and olive oil yielded higher ARA, and lower EPA than canola and soybean oil. Olive oil contained the highest ARA of 48.9 mg/g substrate, and canola oil yielded the highest EPA of 5.7 mg/g substrate. From the viewpoint of the ARA/EPA ratio, canola had a low value of 7.3, followed by 11.7 for soybean oil. Corn and olive oils had much higher ratios of 43.0 and 40.8, respectively, due to high ARA and low EPA.

Example 8

A supercritical $CO_2$ explosion process was investigated to improve the canola digestibility for fungal fermentation. Canola cake and meal as described above were exploded and utilized for fungal digestion both in submerged and solid-state culture. Different canola materials were tested under different explosion conditions and utilized both in submerged and solid-state culture. The effect of the explosion process on the yield of ARA and EPA was evaluated.

*Mortierella alpine* (ATCC 32222) was maintained on potato dextrose agar (PDA) plates and transferred every three weeks. Inoculum preparation was the same as that described above in Example 5.

Canola cake and meal as described previously were stored at $-20°$ C. in a sealed plastic bag. Prior to being used, canola cakes were stored for 6 months and canola meal for 9 months. For uniformity, the cake was screened within the range of 0.5-1.0 mm. The screened canola cake had 15% oil content and 3.5% moisture. Canola meal was utilized originally with less than 1% oil content and the moisture was 2.8%. The particle size of canola meal was less than 0.5 mm.

A submerged culture was developed using exploded canola cake as substrate. The different explosion conditions examined included temperature (35° C. and 65° C.), pressure (3,000 psi and 6,000 psi) and saturation time (10 min and 30 min). Explosion equipment and operation procedure was similar to that described above. Canola cake (10 g) was exploded and stored at $-20°$ C. after explosion treatment. Each treatment had two replicates. Before being used for fungal culture the exploded cake was stored 3 months. The exploded cake (1.5 g) was taken from each explosion replicate for each submerged culture. Raw (non-exploded) canola cakes were used as control. The culture method was the same as that described above in Example 5.

Different explosion factors had different effects on the lipid yields as shown in Table 14, below, in which the F statistic (also known as the F-ratio) is equivalent to $MSR/MSE=(SSR/1)/(s^2_e)$, in which MSR is the predicted mean-squared-anomaly and MSE is the mean-squared-error, according to standard statistical modeling, and $Pr<0.05$ is considered statistically significant.

TABLE 14

| | Pr (>F) | | |
|---|---|---|---|
| Effect | Total lipids | ARA | EPA |
| Temperature (T) | 0.0010 | 0.0019 | 0.0025 |
| Pressure (P) | 0.1038 | 0.7655 | 0.8483 |
| Time (t) | 0.3091 | 0.5700 | 0.6419 |
| T * P | 0.4543 | 0.0359 | 0.0244 |
| P * T | 0.2033 | 0.5129 | 0.4282 |
| T * t | 0.1038 | 0.7016 | 0.5980 |
| T * P * t | 0.3765 | 0.4421 | 0.5152 |

Figure 29:
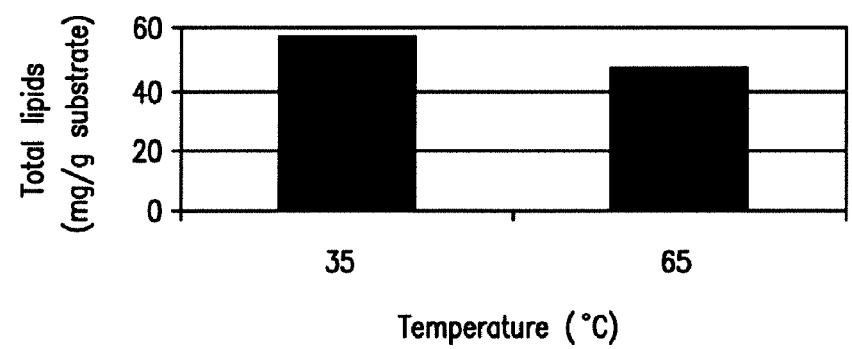
FIG. 29 illustrates the effect of temperature during substrate explosion on total lipids formed following development of a culture on the exploded substrate.
Figure 30:
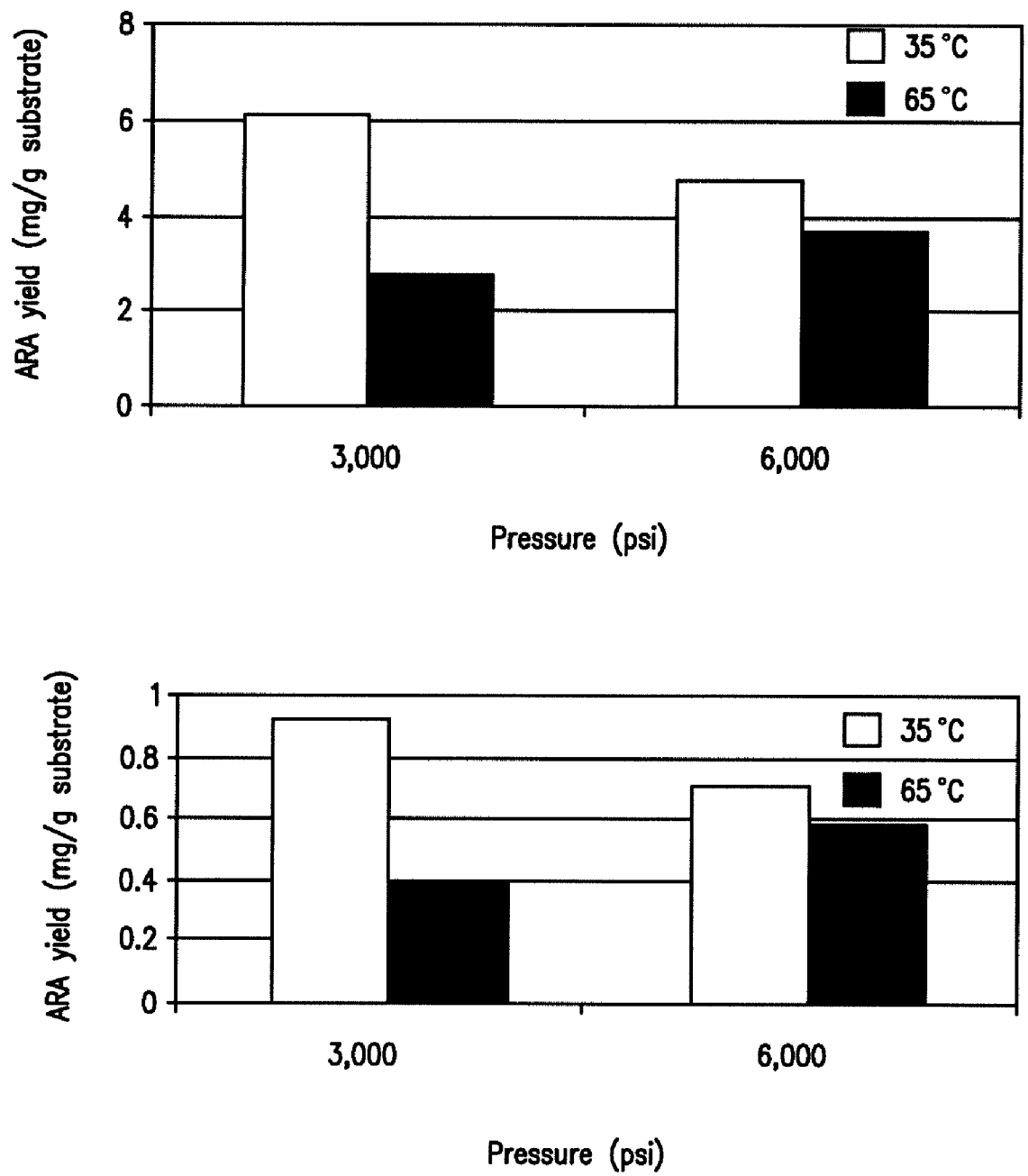
FIG. 30 illustrates the interaction effects of substrate explosion temperature and pressure on ARA (FIG. 30 top) and EPA (FIG. 30 bottom) obtained according to a process as described herein.

Temperature had significant effect on the yields of total lipids, ARA and EPA, and temperature and pressure had an interaction effect on the ARA and EPA yield. For total lipids, lower temperature resulted in higher yields as shown in FIG. 29. As shown in FIG. 30, lower temperature resulted in higher yield at the lower pressure. However, higher temperature had higher yield at the higher pressure for ARA. For EPA yields, treatments had similar effects as to ARA yields. Saturation time had no significant effect on the yields of total lipids, ARA and EPA. Table 15, below, shows the yields of total lipids, ARA and EPA for each explosion treatment by LSD analysis. All treatments were not significantly different from the control, though there existed differences between treatments.

TABLE 15

| Treatment | Total Lipids mg/g substrate | ARA mg/g substrate | EPA mg/g substrate |
|---|---|---|---|
| 35° C. - 3000 psi - 10 min | 54.33 | 6.33 | 0.96 |
| 35° C. - 3000 psi - 30 min | 57.00 | 5.80 | 0.89 |
| 35° C. - 6000 psi - 10 min | 57.66 | 4.94 | 0.75 |
| 35° C. - 6000 psi - 30 min | 58.33 | 4.53 | 0.66 |
| 65° C. - 6000 psi - 10 min | 54.33 | 4.19 | 0.64 |
| 65° C. - 6000 psi - 30 min | 43.66 | 3.39 | 0.53 |
| 65° C. - 3000 psi - 10 min | 43.33 | 2.45 | 0.33 |

TABLE 15-continued

| Treatment | Total Lipids mg/g substrate | ARA mg/g substrate | EPA mg/g substrate |
|---|---|---|---|
| 65° C. - 3000 psi - 30 min | 42.00 | 3.06 | 0.45 |
| Control | 49.00 | 4.36 | 0.66 |

Example 9

Canola cakes exploded as described above in Experiment 8 were used for solid-state cultures in 250 ml flasks. Non-exploded canola cakes were used as control. Exploded cakes (1.5 g) taken from each explosion replicate were adjusted to about 70% moisture by adding 875 µL tap water. After autoclaving with 121° C. and 15 min, 2.5 ml inoculums (preparation method was the same as described above) was inoculated and incubated at the same conditions as that for submerged culture, 20° C. and 150 rpm for 7 days. Another experiment was also conducted by directly inoculating fungi without autoclaving, to avoid the potential co-effect of autoclaving with explosion process on the culture. Sterilized tap water was used for moisture adjustment to 70% based on wet weight.

When cultured with autoclaving, different explosion factors had different effects on the each yields of total lipids, ARA and EPA as shown in Table 16, below.

TABLE 16

| | Pr > F | | |
|---|---|---|---|
| Effect | Total lipids | ARA | EPA |
| Temperature (T) | 0.0154 | 0.1330 | 0.8202 |
| Pressure (P) | 0.0003 | 0.3335 | 0.1280 |
| Time (t) | 0.2509 | 0.0151 | 0.0128 |
| T * P | 0.9689 | 0.3928 | 0.7260 |
| P * T | 0.4857 | 0.0315 | 0.0047 |
| T * t | 0.8283 | 0.1978 | 0.5397 |
| T * P * t | 0.2949 | 0.8746 | 0.1904 |

Figure 31:
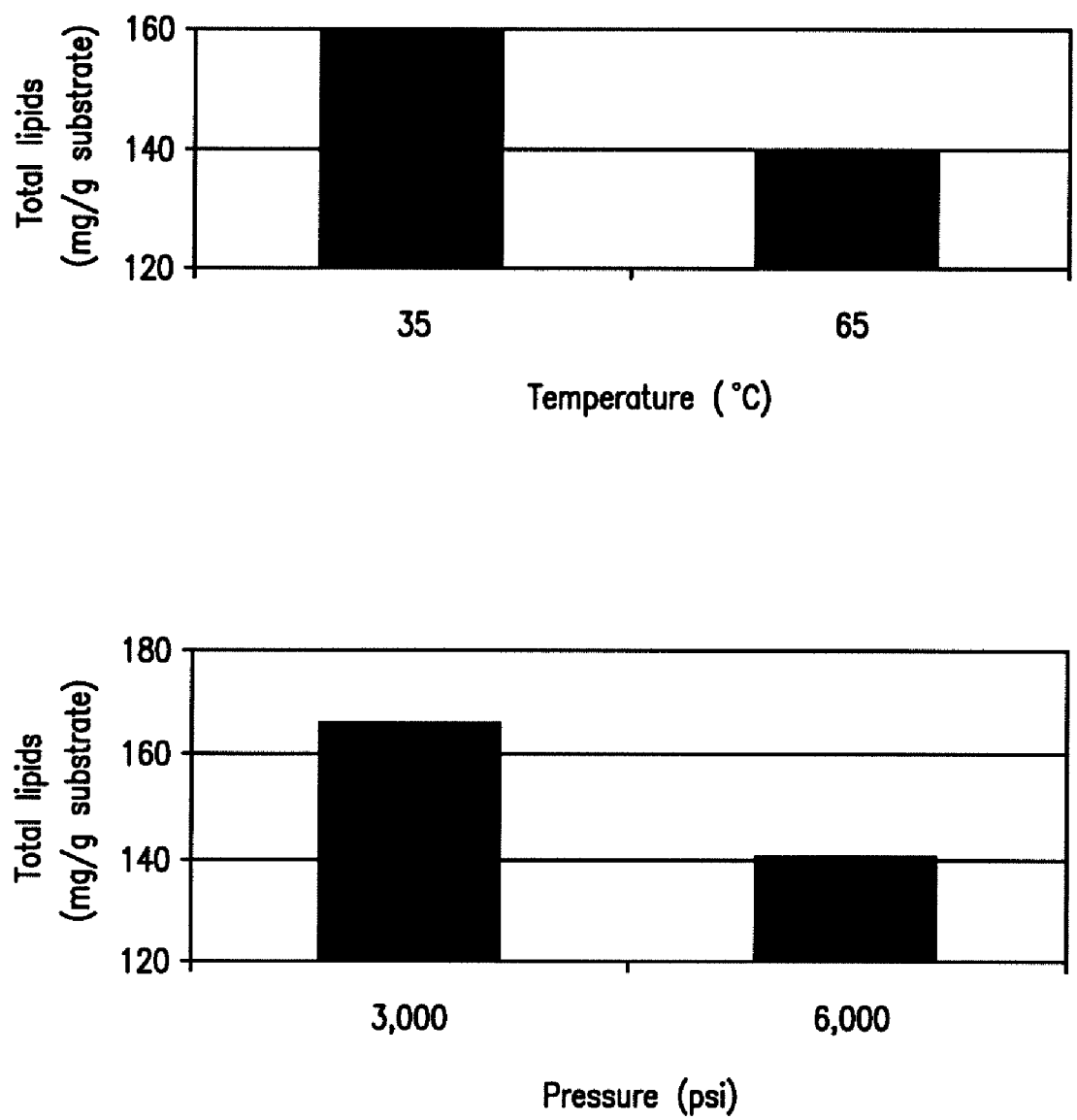
FIG. 31 illustrates the effect of substrate explosion temperature (FIG. 31, top) and pressure (FIG. 31, bottom) on total lipids formed.
Figure 32:
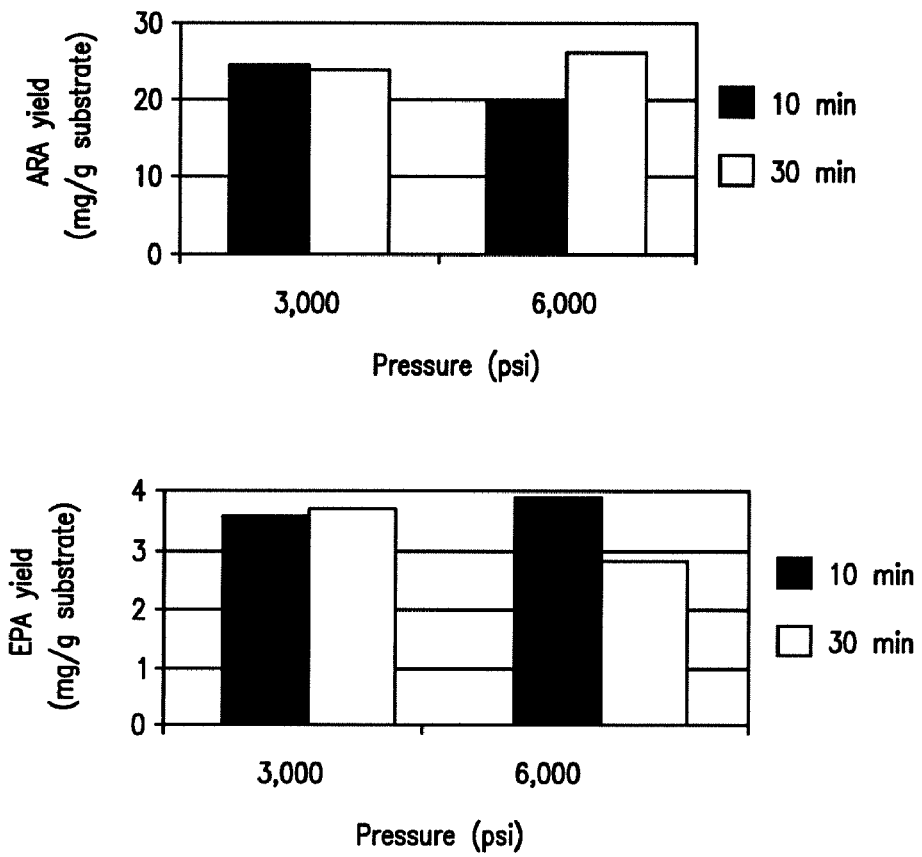
FIG. 32 illustrates the interaction effects of substrate explosion pressure and time on ARA (FIG. 32, top) and EPA (FIG. 32, bottom) yields.

As can be seen, both temperature and pressure had a significant effect on the yield of total lipids, but there was no interaction between temperature and pressure. The lower temperature had higher yield of total lipids, and lower pressure resulted in higher total lipid yield (FIG. 31). As shown in FIG. 32, saturation time had a significant effect on the ARA and EPA yields, and saturation time and pressure showed significant interaction. For ARA, shorter time resulted in higher yield at lower pressure; however, longer time resulted in higher yield at the higher pressure. For EPA, shorter time resulted in higher yield at the higher pressure; however, longer time resulted in higher yield at the lower pressure. Table 17, below, shows the yields of total lipids, ARA and EPA for each explosion treatment. Treatment 4 and 6 were significantly different from the control including all the yields of total lipids, ARA and EPA.

TABLE 17

| Treatment | Total Lipids mg/g substrate | ARA mg/g substrate | EPA mg/g substrate |
|---|---|---|---|
| 35° C. - 3000 psi - 10 min | 179.00 | 23.61 | 3.37 |
| 35° C. - 3000 psi - 30 min | 173.00 | 24.48 | 3.80 |
| 35° C. - 6000 psi - 10 min | 143.66 | 24.19 | 3.99 |
| 35° C. - 6000 psi - 30 min | 141.00 | 19.45 | 2.76 |
| 65° C. - 6000 psi - 10 min | 144.33 | 28.96 | 3.84 |

TABLE 17-continued

| Treatment | Total Lipids mg/g substrate | ARA mg/g substrate | EPA mg/g substrate |
|---|---|---|---|
| 65° C. - 6000 psi - 30 min | 130.16 | 20.61 | 2.86 |
| 65° C. - 3000 psi - 10 min | 154.00 | 25.92 | 3.78 |
| 65° C. - 3000 psi - 30 min | 155.66 | 23.94 | 3.57 |
| Control | 183.33 | 29.82 | 3.99 |

When cultured without autoclave, temperature had significant effect on the yield of total lipids, and the interaction between temperature and pressure was observed. However, all factors including temperature, pressure and saturation time had no significant effect on the yields of ARA and EPA, as shown in Table 18. Table 19 shows the yields of total lipids, ARA and EPA for each explosion treatment when culturing was carried out without autoclaving. All treatments were not significantly different from the control.

TABLE 18

| | Pr > F | | |
|---|---|---|---|
| Effect | Total lipids | ARA | EPA |
| Temperature (T) | 0.0014 | 0.3148 | 0.6920 |
| Pressure (P) | 0.9680 | 0.6423 | 0.1378 |
| Time (t) | 0.2253 | 0.8330 | 0.6442 |
| T * P | 0.0023 | 0.4469 | 0.1573 |
| P * T | 0.3633 | 0.6526 | 0.5026 |
| T * t | 0.0208 | 0.1302 | 0.1421 |
| T * P * t | 0.0339 | 0.6999 | 0.9268 |

TABLE 19

| Treatment | Total Lipids mg/g substrate | ARA mg/g substrate | EPA mg/g substrate |
|---|---|---|---|
| 35° C. - 3000 psi - 10 min | 141.11 | 16.78 | 2.64 |
| 35° C. - 3000 psi - 30 min | 157.77 | 21.01 | 3.24 |
| 35° C. - 6000 psi - 10 min | 156.66 | 18.45 | 2.75 |
| 35° C. - 6000 psi - 30 min | 192.22 | 20.20 | 3.05 |
| 65° C. - 6000 psi - 10 min | 138.88 | 21.05 | 2.87 |
| 65° C. - 6000 psi - 30 min | 107.77 | 18.69 | 2.53 |
| 65° C. - 3000 psi - 10 min | 141.11 | 23.01 | 3.43 |
| 65° C. - 3000 psi - 30 min | 154.44 | 20.49 | 3.30 |
| Control | 163.33 | 19.43 | 3.27 |

Example 10

A culture was developed using exploded canola meal substrate. Canola meal (10 g) was exploded each time using the same method for canola cake as in Example 8. The explosion conditions were 65° C., 3,000 psi and 30 min. The treatments of explosion were done in three replicates. The solid-state cultures were conducted using each exploded meal with autoclave (EX-A), exploded meal without autoclave (EX-NA), compared to raw meal with autoclave (R-A), and the raw meal without autoclave, but the meal was treated by supercritical $CO_2$ in the same condition as for explosion, 65° C., 3,000 psi and 30 min, and then very slow release of the $CO_2$ to atmosphere (UEX-NA). In each culture, 0.9 g meal was used and 0.6 g canola oil was added to reach the weight of 1.5 g substrate.

To adjust moisture to about 70%, 875 µL water was supplemented (sterilized water was added for the cultures without autoclaving). The cultures were also conducted for the comparison of EX-A and R-A in submerged cultures with autoclave using 0.9 g meal and 0.6 g canola oil.

Figure 33:
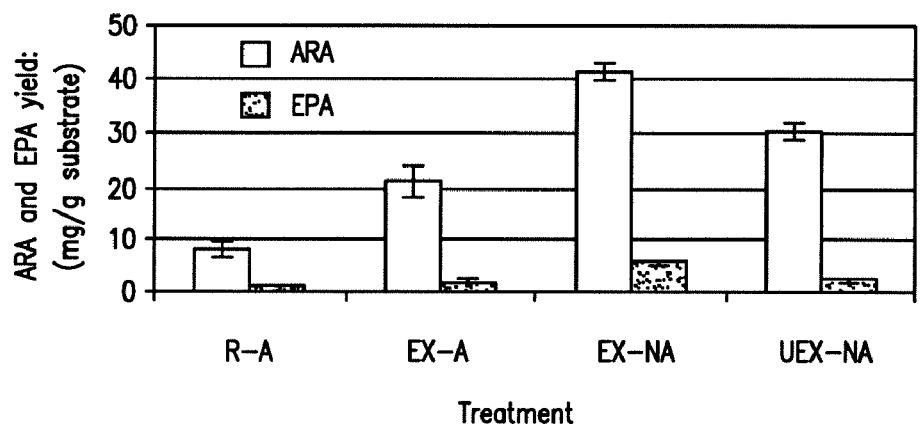
FIG. 33 illustrates the yields of ARA and EPA for a solid state culture on various different substrates as described in Example 10.

In the solid-state culture, the fungi could grow using exploded meal without autoclaving or non-exploded meal with autoclaving. Growth was better without autoclaving than with autoclaving. FIG. 33 shows the yields of ARA and EPA for each culture. The analysis of LSD showed that all treatments were not statistically different for total oil yields, but showed the differences for both ARA and EPA yields. The exploded meal without autoclave (EX-NA) achieved the highest yields of ARA, 40.9 mg/g substrate and EPA, 5.1 mg/g substrate. The raw meal with autoclave (R-A) produced the lowest yields of ARA, 8.3 mg/g substrate and EPA, 0.8 mg/g substrate. Linear contrast of explosion to non-explosion process (EX vs R and UEX) showed that the explosion process improved the yields of ARA and EPA.

Figure 34:
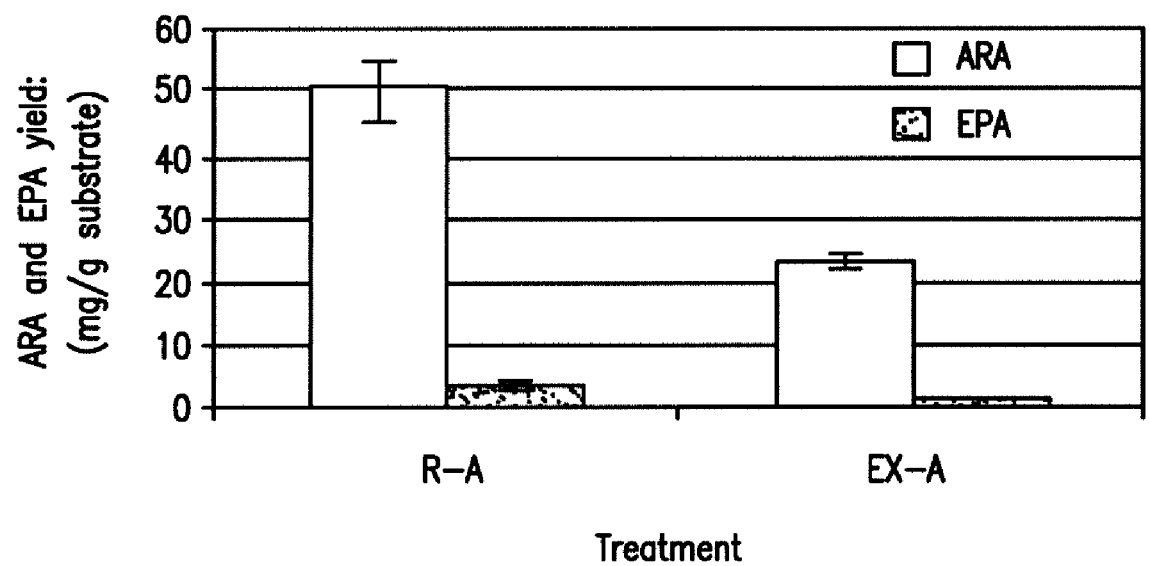
FIG. 34 illustrates the yields of ARA and EPA for submerged culture on two different substrates as described in Example 10.

Linear contrast between with autoclave and without autoclave (A vs NA) showed that the autoclave process decreased the yields of ARA and EPA. In the submerged culture, the larger fungal pellets using exploded meal were observed compared to using raw meal. FIG. 34 shows the yields of ARA and EPA for each culture. The LSD analysis showed that two cultures were not statistically different for total oil yields, but resulted in the differences of both ARA and EPA yields. The explosion process decreased the yields of ARA and EPA.

It will be appreciated that the foregoing examples, given for purposes of illustration, are not to be construed as limiting the scope of this disclosure. Although only a few exemplary embodiments have been described in detail above, those skilled in the art will readily appreciate that many modifications are possible in the exemplary embodiments without materially departing from the novel teachings and advantages of this disclosure. Accordingly, all such modifications are intended to be included within the scope of this disclosure which is herein defined and all equivalents thereto. Further, it is recognized that many embodiments may be conceived that do not achieve all of the advantages of some embodiments, yet the absence of a particular advantage shall not be construed to necessarily mean that such an embodiment is outside the scope of the present disclosure.

What is claimed is:

1. A method for recovering lipids from a biomass comprising:
    developing a biomass on a high polyunsaturated fatty acid content plant feedstock, the plant feedstock including saturated fatty acids, the substrate providing at least one of carbon and nitrogen to the developing biomass, the developing biomass bioconverting lipids of the substrate such that following the bioconversion, the biomass exhibits an alteration in the lipid profile of the biomass; and
    extracting lipids comprising polyunsaturated fatty acids from the developed biomass; wherein
    the ratio of polyunsaturated fatty acids to saturated fatty acids of the lipids extracted from developed biomass is greater than the ratio of polyunsaturated fatty acids to saturated fatty acids of the plant feedstock.

2. The method according to claim 1, wherein the biomass is a microorganism-based biomass.

3. The method according to claim 2, wherein the microorganism-based biomass is an algal biomass.

4. The method according to claim 3, wherein the algal biomass comprises *Chlorella* sp.

5. The method according to claim 2, wherein the microorganism-based biomass is a fungal biomass.

6. The method according to claim 5, wherein the fungal biomass comprises fungi of the species *Pythium* or *Mortierella*.

7. The method according to claim 1, the method further comprising disrupting the cellular structure of the substrate prior to developing the biomass on the substrate.

8. The method according to claim 7, wherein the cellular structure is disrupted according to a carbon dioxide explosion process.

9. The method according to claim 1, wherein the lipids are extracted according to a supercritical fluid extraction process.

10. The method according to claim 9, wherein the supercritical extraction process utilizes supercritical carbon dioxide as solvent.

11. The method according to claim 9, wherein the supercritical extraction processes utilizes supercritical water as solvent.

12. The method according to claim 9, further comprising addition of a co-solvent in conjunction with the supercritical fluid.

13. A method for recovering lipids from a microorganism-based biomass comprising:
    disrupting the cellular structure of a plant-based feedstock substrate, a plant of the plant-based feedstock substrate being an oleaginous plant that includes both polyunsaturated fatty acids and saturated fatty acids;
    developing the microorganism-based biomass on the disrupted feedstock substrate, wherein upon development of the microorganism-based biomass, the microorganisms bioconvert the lipids of the feedstock substrate and thereby alter the lipid profile of the microorganisms in the developed biomass such that the ratio of polyunsaturated fatty acids to saturated fatty acids of the developed biomass is greater than the ratio of polyunsaturated fatty acids to saturated fatty acids of the plant feedstock and wherein the developed biomass includes a polyunsaturated fatty acid that was not present in the feedstock or in the biomass prior to the development;
    disrupting the cellular structure of the microorganisms; and
    extracting lipids of the microorganism-based biomass following disruption of the cellular structure of the microorganisms, the extracted lipids comprising polyunsaturated fatty acids.

14. The method according to claim 13, wherein the plant of the plant-based feedstock substrate comprises a high content of polyunsaturated fatty acids.

15. The method according to claim 14, wherein the plant is canola.

16. The method according to claim 13, wherein the plant of the plant-based feedstock substrate comprises a high content of long chain mono and unsaturated fatty acids.

17. The method according to claim 13, further comprising extracting lipids from the microorganism-based biomass prior to disruption of the cellular structure of the microorganisms.

18. The method according to claim 17, wherein the lipid extraction prior to the cellular disruption of the microorganisms is a carbon dioxide explosion process.

19. The method according to claim 17, wherein the disruption of the cellular structure of the plant-based feedstock substrate is a carbon dioxide explosion process.

20. The method according to claim 13, wherein the disruption of the cellular structure of the microorganisms is a carbon dioxide explosion process.

21. The method according to claim 13, wherein the lipids of the microorganism-based biomass are extracted according to a supercritical fluid extraction process.

22. The method according to claim 21, wherein the supercritical fluid extraction process utilizes carbon dioxide as solvent.

23. The method according to claim 13, wherein the disruption of the cellular structure of the microorganisms is a carbon dioxide explosion process and the lipids of the microorganism-based biomass are extracted according to a carbon dioxide supercritical fluid extraction process.

24. The method according to claim 23, further comprising recycling the carbon dioxide.

25. The method according to claim 23, wherein both the disruption of the cellular structure of the microorganisms and the lipids extraction process are carried out in a single reaction vessel.

26. The method according to claim 13, wherein the microorganism-based biomass is a fungal biomass.

27. The method according to claim 13, wherein the microorganism-based biomass is an algal biomass.

28. The method according to claim 1, wherein the developed biomass includes a polyunsaturated fatty acid that was not present in the feedstock or in the biomass prior to the development.

29. The method according to claim 28, wherein the new polyunsaturated fatty acid is one or more of $\gamma 18:3n6$, $C20:4$, and $C20:5$.

30. The method according to claim 1, wherein the feedstock is canola.

31. The method according to claim 1, further comprising separating the lipids extracted from the developed biomass to form a first oil stream and a second oil stream, the first oil stream comprising the polyunsaturated fatty acids.

32. The method according to claim 31, the second oil stream comprising medium and long chain monounsaturated fatty acids.

33. The method according to claim 32, further comprising forming biodiesel from the second oil stream.

34. The method according to claim 13, wherein the new polyunsaturated fatty acid is one or more of $\gamma 18:3n6$, $C20:4$, and $C20:5$.

35. The method according to claim 13, further comprising separating the extracted lipids to form a first oil stream and a second oil stream, the first oil stream comprising the polyunsaturated fatty acids.

36. The method according to claim 35, the second oil stream comprising medium and long chain monounsaturated fatty acids.

37. The method according to claim 36, further comprising forming biodiesel from the second oil stream.

* * * * *